US009605254B2

(12) United States Patent
Voldman et al.

(10) Patent No.: US 9,605,254 B2
(45) Date of Patent: *Mar. 28, 2017

(54) ELECTROKINETIC CONFINEMENT OF NEURITE GROWTH FOR DYNAMICALLY CONFIGURABLE NEURAL NETWORKS

(71) Applicant: Centre National de la Recherche Scientifique, Paris (FR)

(72) Inventors: Joel Voldman, Belmont, MA (US); Thibault Honegger, Boston, MA (US); David Peyrade, Moirans (FR)

(73) Assignees: MASSACHUSETTS INSTITUTE OF TECHNOLOGY, Cambridge, MA (US); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/154,823

(22) Filed: Jan. 14, 2014

(65) Prior Publication Data
US 2014/0199746 A1    Jul. 17, 2014

Related U.S. Application Data

(60) Provisional application No. 61/752,183, filed on Jan. 14, 2013.

(51) Int. Cl.
| | |
|---|---|
| C12N 13/00 | (2006.01) |
| A61N 1/20 | (2006.01) |
| A61N 1/32 | (2006.01) |
| B03C 5/00 | (2006.01) |
| C12M 3/00 | (2006.01) |
| C12M 1/00 | (2006.01) |
| C12M 1/42 | (2006.01) |
| C12N 5/0793 | (2010.01) |
| B03C 5/02 | (2006.01) |
| B01L 3/00 | (2006.01) |

(52) U.S. Cl.
CPC ............ *C12N 13/00* (2013.01); *A61N 1/205* (2013.01); *A61N 1/326* (2013.01); *B03C 5/005* (2013.01); *B03C 5/026* (2013.01); *C12M 21/08* (2013.01); *C12M 23/34* (2013.01); *C12M 35/02* (2013.01); *C12M 35/04* (2013.01); *C12N 5/0619* (2013.01); *B01L 3/5027* (2013.01); *B03C 2201/26* (2013.01); *C12N 2529/00* (2013.01); *C12N 2533/54* (2013.01); *C12N 2535/00* (2013.01)

(58) Field of Classification Search
None
See application file for complete search history.

(56) References Cited

U.S. PATENT DOCUMENTS

2011/0079513 A1   4/2011   Stelzle et al.
2014/0199745 A1   7/2014   Voldman et al.

OTHER PUBLICATIONS

Peyrin et al., Lab Chip, 2011, 11, 3663.*
Bozhurt et al., "In vitro assessment of axonal growth using dorsal root ganglia explants in a novel three-dimensional collagen matrix." *Tissue engineering*, 13(12):2971-2979, 2007.
Carnegie et al., "Guided neuronal growth using optical line traps." *Opt. Express*, 16(14):10507-10517, 2008.
Castellanos et al., "Electrohydrodynamics and dielectrophoresis in microsystems: Scaling laws." *J. Phys. D: Appl. Phys.*, 36(1):2584-2597, 2003.
Castellarnau et al. "Dielectrophoresis as a tool to characterize and differentiate isogenic mutants of *Escherichia coli.*" *Biophys. J.*, 91(10):3937-3945, Nov. 2006.
Clark et al., "Growth cone guidance and neuron morphology on micropatterned laminin surfaces." *J. Cell Sci.*, 105(1):203-212, 1993.
Corey et al., "Aligned electrospun nanofibers specify the direction of dorsal root ganglia neurite growth." *Journal of Biomedical Materials Research*, 83A(3):636-645, 2007.
Dent and Gertler, "Cytoskeletal dynamics and transport in growth cone motility and axon guidance." *Neuron*, 40(2):209-227, Oct. 2003.
Dent et al., "The growth cone cytoskeleton in axon outgrowth and guidance." *Cold Spring Harbor Perspectives in Biology*, 3(3), 2011.
Desai et al., "Cell-based sensors for quantifying the physiological impact of microsystems." *Integr. Biol.*, 3(1):48-56, 2011.
Desai et al., "Plastic masters—rigid templates for soft lithography." *Lab. Chip*, 9(11):1631-1637, 2009.
Deumens et al., "Repairing injured peripheral nerves: Bridging the gap." *Prog. Neurobiol.*, 92(3):245-276, Nov. 2010.
Doyle et al., "One-dimensional topography underlies three-dimensional fibrillar cell migration." *The Journal of cell biology*, 184(4):481-490, 2009.
Feinerman et al., "Reliable neuronal logic devices from patterned hippocampal cultures." *Nat Phys*, 4(12):967-973, Dec. 2008.
Fendyur et al., "Formation of essential ultrastructural interface between cultured hippocampal cells and gold mushroom-shaped mea- towards ?in-cell? recordings from vertebrate neurons." *Frontiers in Neuroengineering*, 4, 2011.
Fischer et al., "Robust micromechanical neurite elicitation in synapse-competent neurons via magnetic bead force application." *Ann. Biomed. Eng.*, 33(9):1229-1237, 2005.

(Continued)

Primary Examiner — Kimberly A. Ballard
Assistant Examiner — Stacey N. MacFarlane
(74) Attorney, Agent, or Firm — Brinks Gilson Lione; G. Peter Nichols

(57) ABSTRACT

Systems and methods for altering neurite growth are generally described. In some embodiments, a system may include a neuron comprising a neurite and electrodes able to generate a physical guidance cue. The physical guidance cue may be used to alter the growth of the neurite and may be temporally and spatially dynamic, such that neurite growth may be altered in a spatial and/or temporal manner. Dynamic control of neurite growth may be used to form directional neural connections, intersections, and/or overlaps.

13 Claims, 31 Drawing Sheets

(56) References Cited

OTHER PUBLICATIONS

Franzew and Guck, "The biophysics of neuronal growth." *Reports on Progress in Physics*, 73(9):094601, 2010.
Gielen et al., "High-resolution local imaging of temperature in dielectrophoretic platforms." *Anal. Chem.*, 82(17):7509-7514, Aug. 2010.
Gomez and Letourneau "Filopodia initiate choices made by sensory neuron growth cones at laminin/fibronectin borders in vitro." *The Journal of Neuroscience*, 14(10):5959-5972, 1994.
Graves et al., "Electrically Mediated Neuronal Guidance with Applied Alternating Current Electric Fields" *Annals of Biomed. Eng.* 39(6) Jun. 2011 1759-1767.
Green and Jones, "Numerical determination of the effective moments of non-spherical particles." *Journal of Physics D: Applied Physics*, 40(1):78, 2007.
Green et al., "Fluid flow induced by nonuniform ac electric fields in electrolytes on microelectrodes. iii. observation of streamlines and numerical simulation." *Phys. Rev. E*, 66(2):026305, Aug. 2002.
Hardelauf et al., "High fidelity neuronal networks formed by plasma masking with a bilayer membrane: analysis of neurodegenerative and neuroprotective processes." *Lab. Chip*, 11(16):2763-2771, 2011.
Heida et al., "Dielectrophoretic trapping of dissociated fetal cortical rat neurons." *Biomedical Engineering*, IEEE Transactions on, 48(8):921-930, Aug. 2001.
Heida et al., "Understanding dielectrophoretic trapping of neuronal cells: modelling electric field, electrode-liquid interface and fluid flow." *J. Phys. D: Appl. Phys.*, 35(13): 1592—, 2002.
Heida et al., "Viability of dielectrophoretically trapped neural cortical cells in culture." *J. Neurosci. Methods*, 110(1-2):37-44, Sep. 2001.
Hisanaga et al., "Apoptotic cell death of a temperature-sensitive central neuronal cell line." *Brain Research*, 684(1):79-86, Jun. 1995.
Honegger et al., "Design and realization of a microfluidic system for dielectrophoretic colloidal handling." *Microelectronic Engineering*, 86(4-6):1401-1403, 2009.
Honegger et al., "Determination of clausius-mossotti factors and surface capacitances for colloidal particles." *Appl. Phys. Lett.*, 98(18):181906, 2011.
Honegger et al., "Electrokinetic confinement of axonal growth for dynamically configurable neural networks." *Lab on a Chip*, 13(4):589-598, 2013.
Honegger et al., "Rotation speed control of janus particles by dielectrophoresis in a microfluidic channel." *J. Vac. Sci. Technol.* B, 28(6):C6I14-C6I19, 2010.
Hsiao et al., "Unfolding collapsed polyelectrolytes in alternating-cm-rent electric fields." *Soft Matter*, 7 (3): 1207-1213, 2011.
Jaber et al., "Action potential recording from dielectrophoretically positioned neurons inside micro-wells of a planar microelectrode array." *J. Neurosci. Methods*, 182(2):225-235, Sep. 2009.
Kaehr et al., "Guiding neuronal development with in situ microfabrication." *Proc. Natl. Acad. Sci. U. S. A.*, 101(46):16104-16108, 2004.
Kunze et al., "Micropatterning neural cell cultures in 3d with a multi-layered scaffold." *Biomaterials*, 32(8):2088-2098, 2011.
Lee et al., "Advances in 3d nano/microfabrication using two-photon initiated polymerization." *Prog. Polym. Sci.*, 33(6):631-681, 2008.
Lee et al., "Microfluidic alignment of collagen fibers for in vitro cell culture." *Biomedical microdevices*, 8(1):35-41, 2006.
Lee et al., "Topographical guidance of mouse neuronal cell on sio2 microtracks." *Sens. Actuators*, B, 128(1):252-257, 2007.
Loverde et al., "Axon stretch growth: The mechanotransduction of neuronal growth." *J Vis Exp*, (54):e2753—, Aug. 2011.
Lowery and Van Vactor, "The trip of the tip understanding the growth cone machinery." *Nat. Rev. Mol. Cell Biol.*, 10(5):332-343, May 2009.
Lynch et al., Nanoscale dielectrophoretic spectroscopy of individual immobilized mammalian blood cells, Oct. 2006.
Mai et al., "Axon initiation and growth cone turning on bound protein gradients." *The Journal of Neuroscience*, 29(23):7450-7458, 2009.
Moore et al., "Traction on immobilized netrin-1 is sufficient to reorient axons." *Science*, 325(5937):166, 2009.
Morgan et al., "Separation of submicron bioparticles by dielectrophoresis." *Biophys. J.*, 77(1):516-525, 1999.
Nakagawa et al., "Regulation of neurogenesis in adult mouse hippocampus by camp and the camp response element-binding protein." *J. Neurosci.*, 22(9):3673-3682, 2002.
Park et al., "Microfluidic culture platform for neuroscience research" *Nature Protocols* 2006 1(4): 2128-2136.
Patel and Poo, "Orientation of neurite growth by extracellular electric fields." *J. Neurosci.*, 2(4):483-496, 1982.
Pethig, "Review article-dielectrophoresis: Status of the theory, technology, and applications." *Biomicrofluidics*, 4(2):022811, 2010.
Peyrin et al., "Axon diodes for the reconstruction of oriented neuronal networks in microfluidic chambers." *Lab. Chip*, 11(21):3663-3673, 2011.
Prasad et al., "Electric field assisted patterning of neuronal networks for the study of brain functions." *Biomed. Microdevices*, 14:127, 2003.
Preibisch et al. "Globally optimal stitching of tiled 3d microscopic image acquisitions." *Bioinformatics*, 25(11):1463-1465, 2009.
Prieto et al., "Frequency discretization in dielectrophoretic assisted cell sorting arrays to isolate neural cells." *Lab. Chip*, 12(12):2182-2189, 2012.
Ramos et al., "Ac electrokinetics: A review of forces in microelectrode structures." *J. Phys. D: Appl. Phys.*, 31:2338-2353, 1998.
Robinson and Cormie, "Electric field effects on human spinal injury: Is there a basis in the in vitro studies?" *Devel Neurobio*, 68(2):274-280, 2008.
Sbalzarini and Koumoutsakos, "Feature point tracking and trajectory analysis for video imaging in cell biology." *Journal of Structural Biology*, 151(2):182-195, 2005.
Schnelle et al., "The influence of higher moments on particle behaviour in dielectrophoretic field cages." *Journal of Electrostatics*, 46(1):13-28, Mar. 1999.
Scott, "Ultra-Rapid 2-D and 3-D Laser Microprinting of Proteins." PhD thesis, Massachusetts Institute of Technology, 2013.
Stevenson et al., "Optically guided neuronal growth at near infrared wavelengths." *Opt. Express*, 14(21):-, 2006.
Sung et al., "Control of 3-dimensional collagen matrix polymerization for reproducible human mammary fibroblast cell culture in microfluidic devices." *Biomaterials*, 30(27):4833-4841, 2009.
Taylor et al., "A microfluidic culture platform for cns axonal injury, regeneration and transport." *Nat Meth*, 2(8):599-605, Aug. 2005.
Taylor et al., "Microfluidic local perfusion chambers for the visualization and manipulation of synapses." *Neuron*, 66(1):57-68, Apr. 2010.
Tsai and Miller, "Glial cell migration directed by axon guidance cues." *Trends in neurosciences*, 25(4):173-175, 2002.
Vahey and Voldman, "High-throughput cell and particle characterization using isodielectric separation." *Anal. Chem.*, 81(7):2446-2455, 2009.
Voldman, "Electrical forces for microscale cell manipulation." *Annu. Rev. Biomed. Eng.*, 8:425-454, 2006.
Wilson et al., "Surface organization and nanopatterning of collagen by dip-pen nanolithography." *Proceedings of the National Academy of Sciences*, 98(24):13660-13664, 2001.
Wissner-Gross et al., "Large-scale analysis of neurite growth dynamics on micropatterned substrates." *Integr. Biol.*, 3(1):65-74, 2011.
Wu et al., "A photon-driven micromotor can direct nerve fibre growth" *Nature Photonics* Jun. 2012 6: 62-67.
Yu et al., "Dynamic regulation of axon guidance." *Nat. Neurosci.*, pages—, Oct. 2001.
Yu et al., "Negative dielectrophoretic force assisted construction of ordered neuronal networks on cell positioning bioelectronic chips." *Biomed. Microdevices*, 6(4):311-324, 2004.

(56) References Cited

OTHER PUBLICATIONS

Zhang and Zhu, "Directed assembly of janus particles under high frequency ac-electric fields: Effects of medium conductivity and colloidal surface chemistry." *Langmuir*, 28(37):13201-13207, Aug. 2012.

International Search and Written Opinion mailed May 8, 2014 for Application No. PCT.US2014/011444.

Fan et al., Single neuron capture and axonal development in three-dimensional microscale hydrogels. Lab Chip. Nov. 21, 2012;12(22):4724-31. doi: 10.1039/c2lc40312a.

Honegger et al., 4-D dielectrophoretic handling of Janus particles in a microfluidic chip. Micro Engin. May-Aug. 2010; 87(5-8): 756-9. doi: 10.1016/j.mee.2009.11.145.

Honegger, Électronicinétique tridimensionnelle de particules colloïales en géométrie microfluidique et application à la manipulation de cellules. Thesis submitted to Université de Grenoble, Nov. 17, 2011. 242 pages. Retrieved from the Internet via http://tel.archives-ouvertes.fr/docs/00/66/82/80/PDF/23060_HONEGGER_2011)diffusion1.pdf on Apr. 15, 2014. See English abstract on p. 242.

Honegger et al., Transparent multilevel aligned electrode microfluidic chip for dielectrophoretic colloidal handling. Micro Nanosysms. 2010; 2(4): 239-48. doi: 10.2174/1876402911002040239.

U.S. Appl. No. 14/154,797, filed Jan. 14, 2014, Voldman et al.

\* cited by examiner

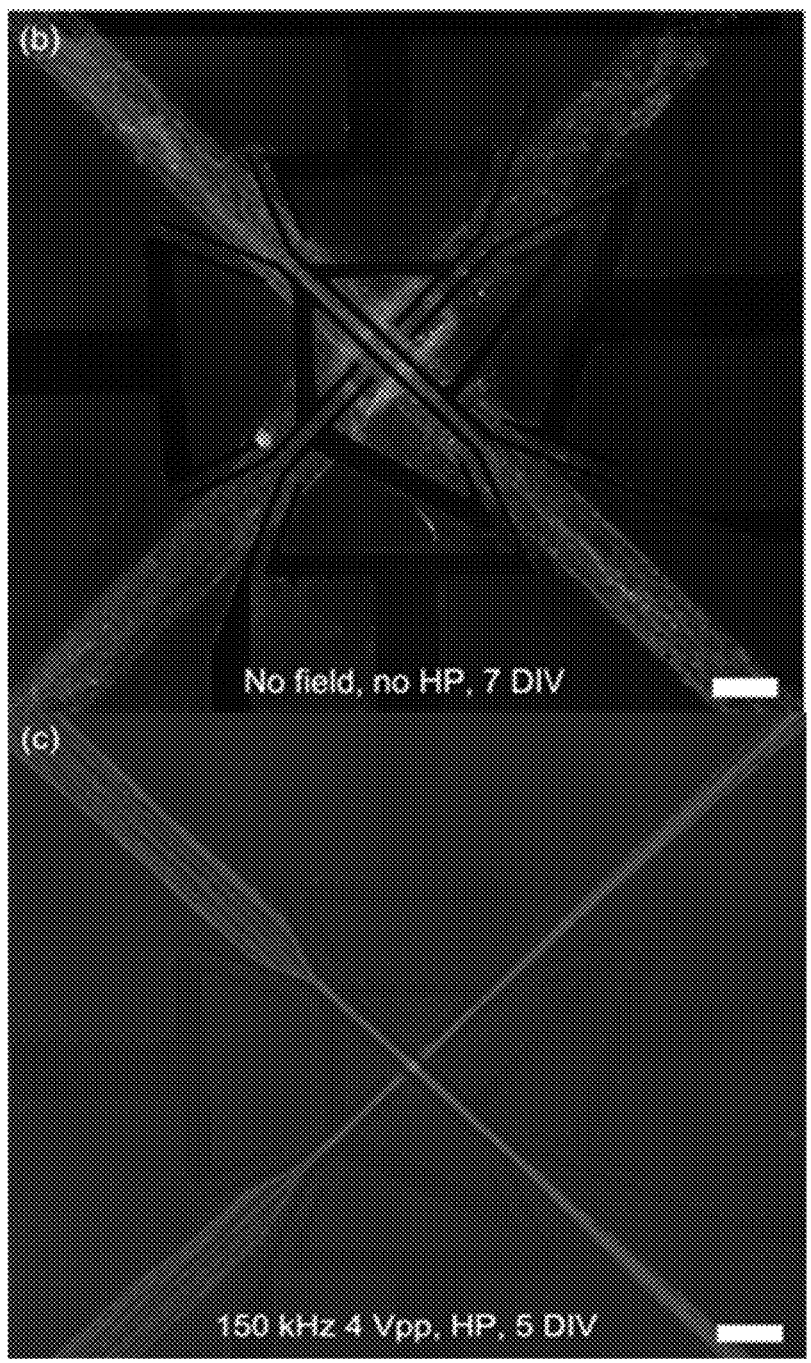
FIG. 21B-C

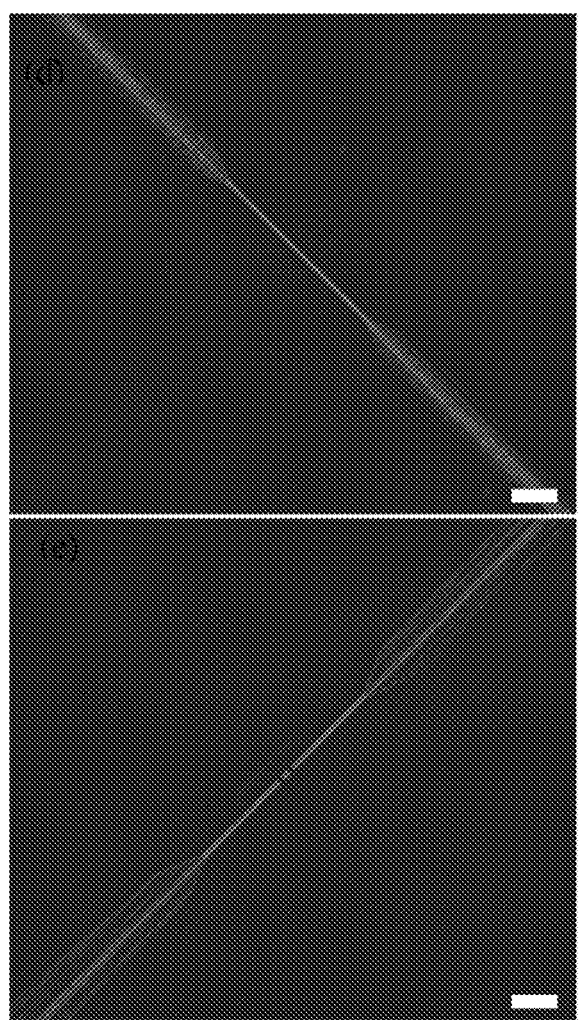
FIG. 21D-E

ELECTROKINETIC CONFINEMENT OF NEURITE GROWTH FOR DYNAMICALLY CONFIGURABLE NEURAL NETWORKS

RELATED APPLICATIONS

This application claims priority to U.S. Provisional Patent Application Ser. No. 61/752,183, filed Jan. 14, 2013, and entitled "Electrokinetic Confinement of Neurite Growth for Dynamically Configurable Neural Networks," which is incorporated herein by reference in its entirety for all purposes.

GOVERNMENT SPONSORSHIP

This invention was made with Government support under Grant No. DBI-0852654 awarded by the National Science Foundation and Grant No. RO1-NS066352, awarded by the National Institutes of Health. The Government has certain rights in this invention.

TECHNICAL FIELD

Systems and methods for altering neurite growth are provided.

BACKGROUND

Developing neurites in vivo are subject to guidance cues that vary both spatially and temporally. These guidance cues enable neurons to form functional neural networks. For example, early neurites from retinal ganglion cells in *Xenopus* larvae decussate at the optic chiasm to form contralateral connections, but some later neurites are repelled from the midline due to heightened ephrin-B expression and do not cross. Studying and manipulating such processes requires methods and systems that can provide both temporal and spatial control over neurite development. In addition, scalable methods and systems able to form small neural networks including a few neurites spread over short distances and large neural networks including a large number of neurites spread over long distances are also needed. Existing methods are unable to dynamically alter neurite development and/or are not readily scalable. Accordingly, improved methods and systems are needed.

SUMMARY

Systems and methods for altering neurite growth are provided. The subject matter of the present invention involves, in some cases, interrelated products, alternative solutions to a particular problem, and/or a plurality of different uses of one or more systems and/or articles.

In one set of embodiments, a series of methods is provided. In one embodiment, a method comprises providing a neuron comprising one or more neurite, providing an alternating current electric field, and directionally guiding elongation of one or more neurite using the alternating current electric field.

In another embodiment, a method comprises directionally guiding elongation of a neurite using an alternating current electric field.

In another embodiment, a method comprises affecting growth of a neurite with a field produced by two or more electrodes. The center to center spacing between the electrodes is less than or equal to about 200 microns.

In another embodiment, a method comprises affecting growth of a neurite multi-directionally with an electric field. The electric field has a magnitude of greater than or equal to about 100 V/m in the vicinity of the neurite.

In another embodiment, a method comprises providing a neuron comprising a neurite, providing a physical guidance cue, and controlling growth of the neurite using the physical guidance cue. The physical guidance cue can reversibly arrest growth of the neurite.

In another embodiment, a method comprises allowing growth of a neurite in a first orientation and applying a non-mechanically-actuated physical guidance cue to the neurite, thereby affecting the neurite such that growth of the neurite occurs in a second orientation.

In another embodiment, a method comprises providing more than one neuron, wherein each neuron comprises one or more neurite. The method also comprises providing an electric field, controlling a neurite independently of another neurite, and forming a neural network from the more than one neuron.

In one embodiment, a method comprises causing first neurites to overlap a second neurites using a guidance cue.

In another embodiment, a method comprises guiding growth of a neurite such that it overlaps a second neurite.

In one embodiment, a method comprises directionally guiding elongation of first neurites and second neurites within a three-dimensional scaffold to form a neural network between the first and second population of neurites using an electric field.

In another embodiment, a method comprises accelerating neurite elongation within a three-dimensional scaffold using an electric field.

In another set of embodiments, a series of articles are provided. In one embodiment, an article comprises a chamber capable of housing a living cell and promoting cell growth, a channel, and a plurality of electrode pairs. The channel is connected to the chamber and the channel has a height and/or width of less than or equal to about 20 microns. An electrode pair comprises two electrodes with a center to center spacing of less than or equal to about 200 microns. The plurality of electrode pairs intersects the channel.

In another embodiment, an article comprises a first chamber connected to a first channel, a first electrode pair aligned with at least a portion of the first channel, a second chamber connected to a second channel, and a a second electrode pair aligned with at least a portion of the second channel. A portion of the first electrode pair may overlap with at least a portion of the first chamber and a portion of the second electrode pair may overlap with at least a portion of the second chamber. In some instances, the first and second channels intersect at an overlap region having a height of greater than about 10 microns.

In another embodiment, an article comprises a first channel connected to a first chamber and a second chamber and a first electrode pair aligned with at least a portion of the first channel. In some instances, a portion of the first electrode pair overlaps with at least a portion of the first chamber and a center to center spacing between the first electrode pair is less than or equal to about 200 microns.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 21A-G illustrate device for guiding neurites, in accordance with one embodiment of the invention;

DETAILED DESCRIPTION

The present invention generally relates to neural outgrowth of one or more neurons. Systems and methods for altering neurite growth are generally described. In some embodiments, a system (e.g., microfluidic system) may include a neuron comprising a neurite (e.g., axon) and components able to generate a physical guidance cue (e.g., electrokinetic force). The physical guidance cue may be used to alter the growth of the neurite and may be temporally and spatially dynamic, such that neurite growth may be altered in a spatial and/or temporal manner. In some instances, the components may be electrodes and the physical guidance cue may be electrokinetic forces that are produced by an electric field (e.g., alternating current electric field). In some cases, the system may include more than one neuron, each neuron comprising a neurite. In some such cases, one or more physical guidance cues may be used to form unidirectional connections between the neurites. These systems may be particularly well-suited for applications in quantitative studies of neurite growth, neural signaling, and the formation of engineered, oriented neural networks, though these systems may be used in other applications.

Neurite growth in living organisms is directed via guidance cues, whose expression varies both spatially and temporally, to form functional neural connections. Existing systems and methods to study neurite growth and/or form neural connections use static geometries, and are unable to dynamically alter the guidance cues imparted on the neurite. Moreover, many of these systems and methods cannot be readily scaled to form neural networks from a large numbers of neurites across large distances.

It has been discovered, within the context of certain embodiments of the present invention, that spatial and temporal control over neurite growth and the formation of scalable, oriented neural networks can be achieved using dynamic physical guidance cues (e.g., electrokinetic phenomena). Dynamic control of neurite growth opens up a number of applications ranging from developmental biology (e.g., developmental neuroscience) to regenerative devices (e.g., for peripheral nerve injury).

Figure 1A:
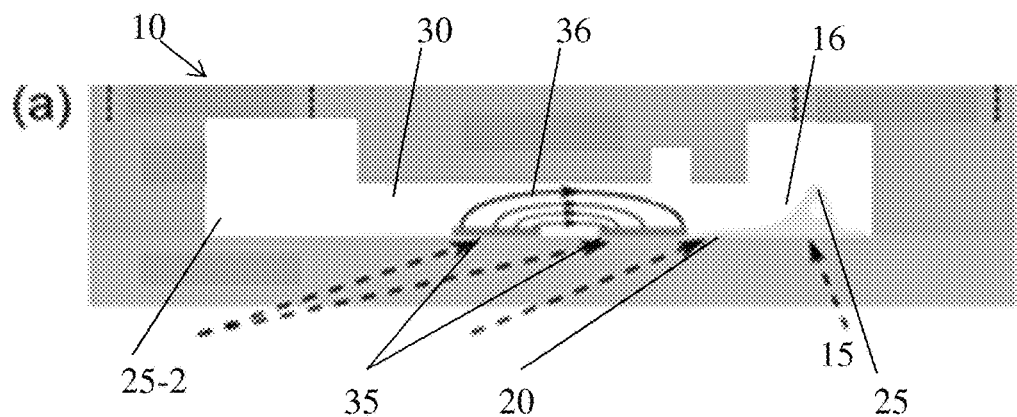
FIGS. 1A-E illustrate certain embodiments of the invention generally directed to altering neurite growth.

An example of a device for altering neurite (e.g., axon, dendrite) growth using a dynamic physical guidance cue is shown in FIG. 1A. As shown illustratively in FIG. 1A, a device 10 may contain a neuron 15, comprising one or more neurites 20, located in a chamber 25. The device may include the chamber 25, which is capable of housing a living cell and promoting cell growth, channels 30, in which neurites can grow, and electrodes 35 that are capable of generating a physical guidance cue. In some embodiments, the chamber and the channels may be configured such that the neuron cell body 16 is confined to the chamber, while one or more neurites may grow into channels 30. In one example, the channels may have a dimension (e.g., height, width, cross-sectional area) that is smaller than a dimension of the neuron cell body, but larger than an average dimension of neurites. A dimension of the channels, in some instances, may also limit the number of neurites that occupy the channel and the directionality of the neurites. For example, the cross-sectional area of a channel may allow a single neurite to occupy the channel. In other instances, the cross-sectional area of a channel may allow a plurality of neurites (e.g., a population of neurites) to occupy the channel. In certain embodiments, the channels may act to limit the directionality of neurites by confining neurite growth to one dimension. For example, as shown on FIGS. 1B-1D, the width of channels 30, which connect chamber 25 to a second chamber 25-2, prevent neurites from changing orientation. Therefore, growing neurites, which enter channels 30, will elongate toward chamber 25-2. In other embodiments, the channels may allow for multi-dimensional growth, such as changes in direction and plane. In some instances, the neurites and the neuron cell body may grow in channels 30.

In some embodiments, one or more of the electrodes 35 may intersect at least a portion of channels 30. In some cases, one or more electrode may intersect all the channels and, in other cases, one or more electrode may not intersect all the channels. In certain embodiments, the orientation (e.g., the intersection angle) of the electrodes with respect to a channel influences how neurite growth is altered in the presence of a physical guidance cue. For instance, in embodiments in which the physical guidance cue is a force, the orientation of the electrodes may determine the direction of the force. In one example, when the electrodes are perpendicular to the channel (i.e., 90° intersection angle), as shown in FIG. 1A, a force parallel to the channel may be produced. It should be understood that the electrodes do not pose a physical barrier to neurite growth and may be used to produce a non-contact (i.e., contactless) physical guidance cue.

In certain embodiments, one or more electrodes may align and overlap with at least a portion of one or more channel. In some cases, the entire length of one or more electrode may align and overlap with a channel and, in other cases, a portion of the length of one or more electrode may not align and/or overlap with a channels. In certain embodiments, the orientation (e.g., parallel alignment and overlap of one or more electrode with a channel) of the electrodes with respect to a channel influences how neurite growth is altered in the presence of a physical guidance cue. For instance, in some embodiments, the orientation of the electrodes may confine neurite growth to a particular region, path, and/or plane.

In some embodiments, an electric field 36 (e.g., alternating current electric field, direct current electric field) is produced between two electrodes (i.e., electrode pair), as shown in FIG. 1A. The electric field may generate one or more physical guidance cues (e.g., electrokinetic phenomena, joule heating) that can alter the growth of a neurite. In certain embodiments, a physical guidance cue may be localized to a particular vicinity (e.g., between electrodes, near the electrodes). For example, the generation of a physical guidance cue may require an electric field above a certain magnitude (e.g., 100V/m). The physical guidance cue might not be produced in areas below the electric field threshold magnitude.

Figure 1B:
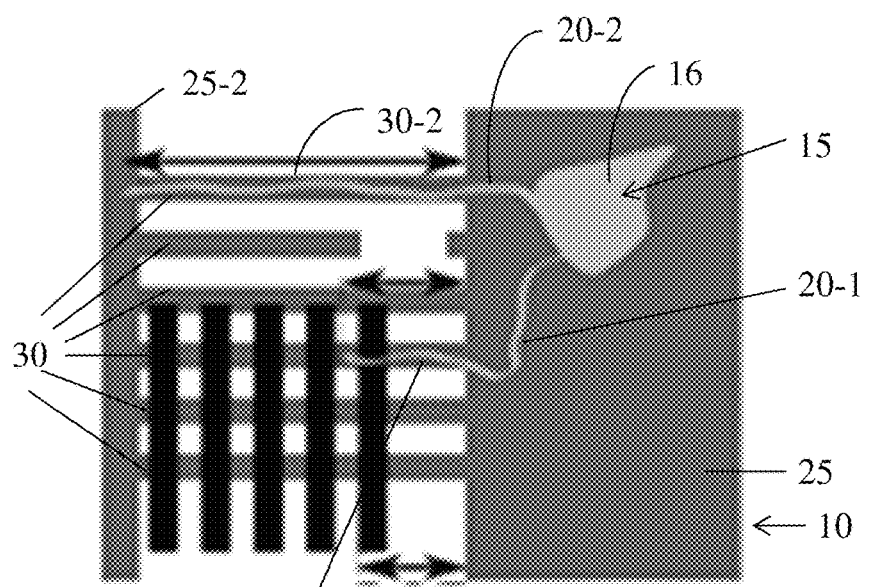
Figure 1C:
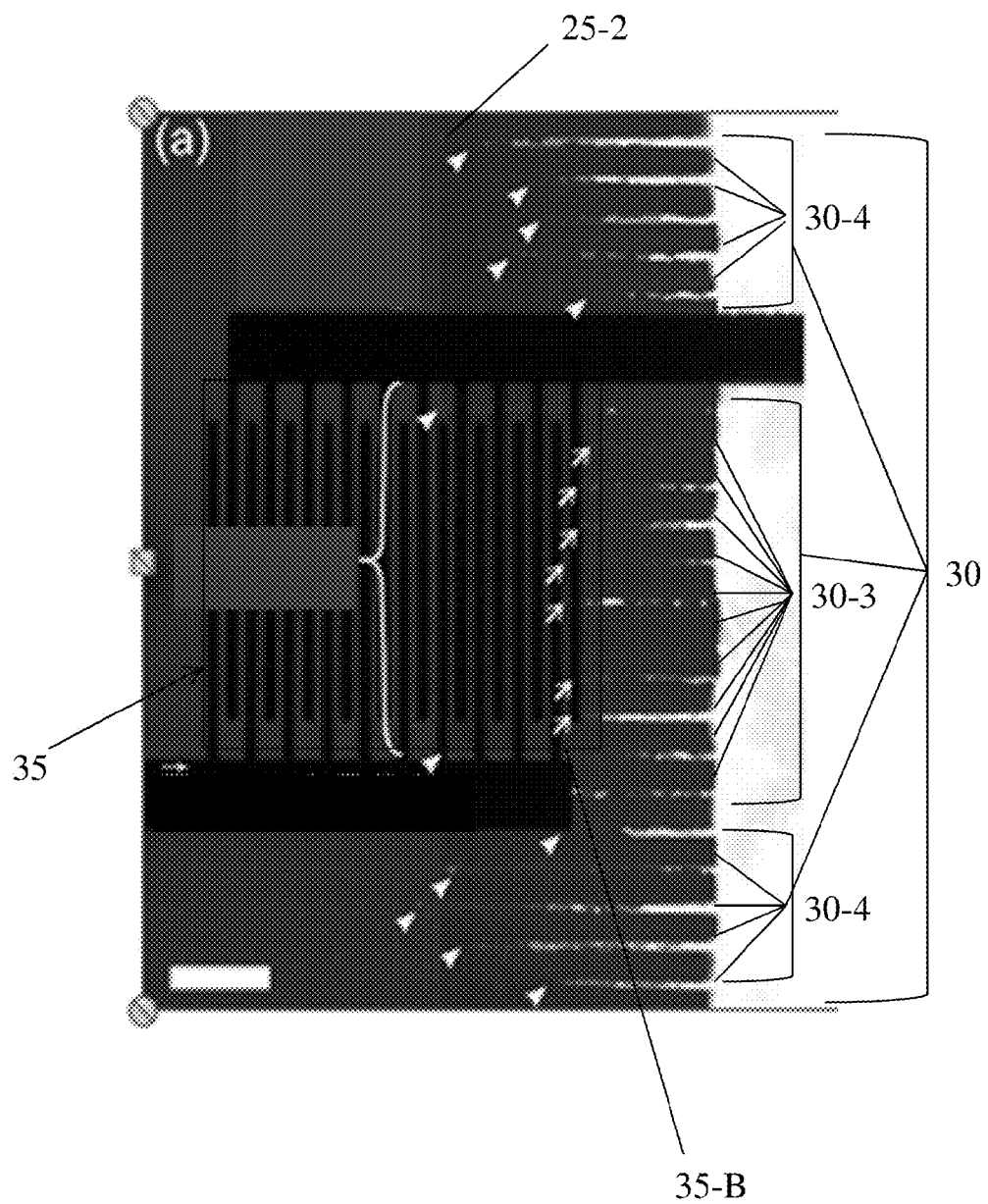
Figure 1D:
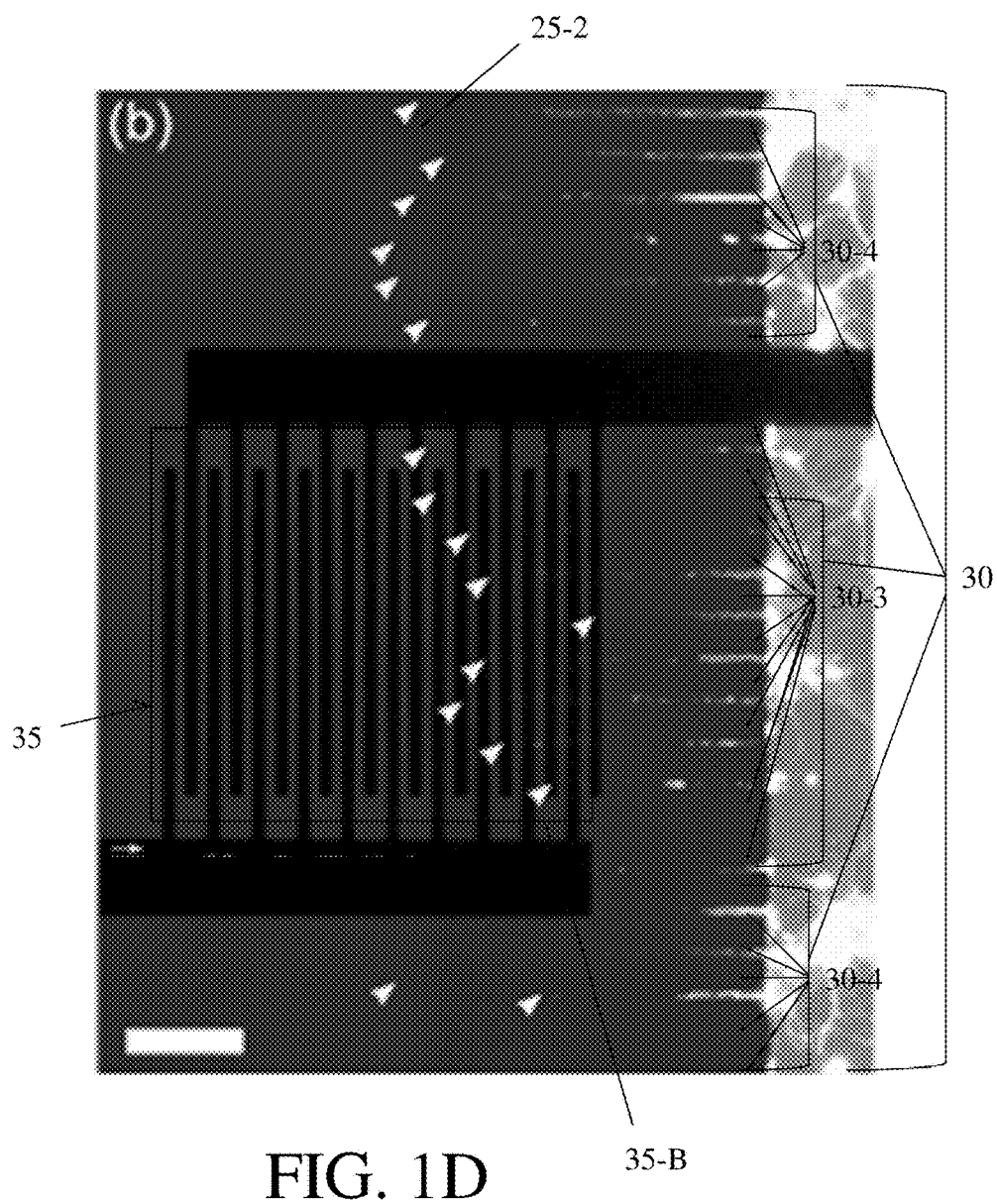

An example of altering neurite growth in device 10 is shown in FIGS. 1B-1D. As illustratively shown in FIG. 1B, device 10 may contain a neuron 15, having a first neurite 20-1 and a second neurite 20-2, located in chamber 25 capable of housing a living cell and promoting cell growth. The electrodes 35 intersect a portion of channels 30. FIG. 1B is a schematic representation of the growth of neurites 20-1 and 20-2 in device 10 after a period of growth is shown. During the period of growth, neurites 20-1 and 20-2 grew into channels 30-1 and 30-2, respectively, and elongated toward chamber 25-2. In some embodiments, a voltage is applied across electrodes 35A and 35B producing a physical guidance cue that prevents elongation of neurite 20-1 past electrode 35B. Neurite 20-2 in the absence of a physical guidance cue may elongate to chamber 25-2, as shown in FIG. 1B.

Figure 1E:
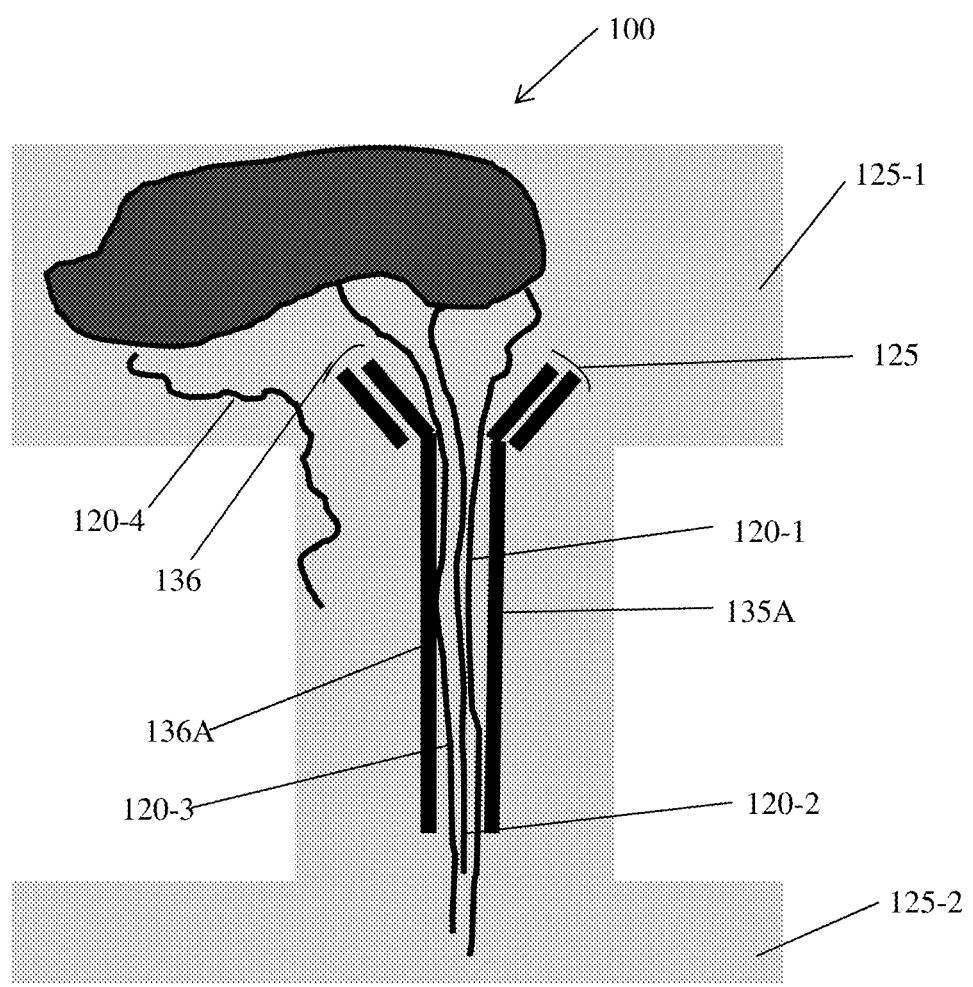

Another example of altering neurite growth is illustrated in FIG. 1E. As shown in FIG. 1E, a device 100 may contain a neuron 115 having several neurites (e.g., 120-1, 120-2, 120-3, 120-4) located in chamber 125-1 capable of housing a living cell and promoting cell growth. In some embodiments, the device may comprise electrodes. In some embodiments, at least a portion of one or more electrode may overlap with the channel. For instance, as illustrated in FIG. 1E, a portion of two pairs of electrodes, electrode pair 135 and electrode pair 136, may overlap the chamber. In certain embodiments, the physical guidance cue produced by the electrodes may direct one or more neurites (e.g., 120-1, 120-2, 120-3) elongating from the neuron into the region between the electrode pair. In some instances, the at least portion of the electrodes may overlap with and align with at least a portion of the channel 130. For instance, as illustrated in FIG. 1E, the electrodes 135A and 136A align with and overlap a portion of channel 130. In some embodiments, the one or more electrodes may be substantially parallel to the walls of the channel. In some instances, a portion of the electrodes may be substantially parallel to the walls of the channel. During the period of growth, neurites 120-1, 120-2, 120-3, and 120-4 grow into channel 130 and elongated toward chamber 125-2. In some embodiments, a voltage is applied to electrodes 135A and 136A producing a physical guidance cue that confines growth (e.g., elongation) within the region between electrodes 135A and 136A and prevents neurites 120-1, 120-2, and 120-3 from growing within the full region defined by channel 130. Neurite 120-4 in the absence of a physical guidance cue may grow in regions outside of the region between electrodes 135A and 136A.

In some embodiments, a neurite confined between electrodes may have enhanced (e.g., accelerated) growth (e.g., elongation) compared to a neurite under essentially identical conditions (culture environment, temperature, pressure, humidity, etc.) that are not confined between electrodes. In some such embodiments, the length of the neurite measured parallel to at least a portion of the electrode pair (e.g., portion that aligns with and overlaps the channel) may be greater than the length of a neurite outside of an electrode pair (i.e., not confined within an electrode pair) but cultured under essentially conditions. Without wishing to be bound by theory, it is believed that neurite growth is enhanced because the forces caused by the physical guidance cue (e.g., electric field) limit the effective probing area of the growth cone of the neurite. The reduction in area reduces the total amount of time spent probing the environment compared to neurites whose effective probing area is not limited. In some embodiments, neurite elongation may be accelerated within three-dimensional scaffold using an electric field. In some such embodiments, the electrodes used to produce the field may not be contained within the scaffold.

In certain embodiments, the alteration in growth of the neurite may be reconfigurable as illustrated in FIGS. 1C-D. FIG. 1C shows an image of device 10 including a plurality of neurons having neurites growing in channels 30. The electrodes 35 intersect channels 30 at channels 30-3 and produce a physical guidance cue in channels 30-3. In some embodiments, neurites growing in channels 30-3 are prevented from elongating past electrode 35B toward chamber 25-2, as indicated by open arrowheads. Neurites growing in channels 30-4 that do not intersect the electrodes can elongate toward chamber 25-2 as indicated by closed arrowheads. In some embodiments, turning off the voltage removes the physical guidance cue, which may reverse the alteration in neurite growth. As shown in FIG. 1D, after the removal of the physical guidance cue, the neurites in channels 30-3 can elongate toward chamber 25-2 as indicated by the closed arrowheads.

As described herein, neurite growth may be altered using a physical guidance cue. Altering neurite growth may involve altering one or more growth characteristics of a neurite. For instance, both neurite length and orientation may be altered. In some instances, substantially all characteristics of neurite growth may be altered. Non-limiting examples of neurite characteristics include growth rates, neurite length, orientation (e.g., direction), location (e.g., plane, dimension), and growth cone characteristics (e.g., actin polarization). Other growth characteristics are also possible. In general any suitable growth characteristic may be altered.

In some embodiments, the terms cue or guidance cue has the ordinary meaning known to one of skill in the art. A cue may refer to a signal (chemical, force, etc.) that can be received by a neuron cell body or neurite and translated by the neuron cell body neurite into instructions relating to one or more growth characteristics. A guidance cue may refer to a cue that after being translated by the neuron cell body or neurite into instructions relating to one or more growth characteristics changes one or more growth characteristics from the normal statistical distribution of that growth characteristic(s) under essentially identical conditions but lacking the cue and allows the growth characteristic to be altered or controlled. In some instances, guiding or affecting neurite growth may involve altering the normal statistical distribution of one or more growth characteristic(s) over an extended period of time (e.g., at least about one hours, at least about 6 hours, at least about 12 hours, at least about 24 hours, at least about 1 day, at least about 2 days, at least about 4 days, at least about a week).

In some embodiments, a physical guidance cue has the ordinary meaning known to one of skill in the art. For instance, in some embodiments, a physical guidance cue is a non-chemical signal, which can be received by a neurite and translated by the neurite into instructions relating to one or more growth characteristics. Non-limiting examples of physical guidance cues include electrokinetic phenomena (e.g., dielectrophoresis, electroosmosis, electrothermal effects), energy (e.g., thermal), mechanical forces (e.g., generated by fluid flow, interactions with structural barriers), non-mechanically actuated forces, optical cues, and combinations thereof. It should be understood that though a physical guidance cue may not involve the direct application of a chemical species to a neurite, a physical guidance cue may produce a chemical species and/or cause a chemical species to alter neurite growth. In some embodiments, a non-mechanically actuated force may refer to a non-contact force which is not produced by or originates from one or more mechanically actuated element (e.g., particle mechanically actuated to spin). In some embodiments, the physical guidance cue may be produced by or originate from one or more elements that do not directly contact the neurite and/or act as a physical barrier to neurite growth.

The manner, in which, a physical guidance cue alters neurite growth may depend on a number of factors, such as the geometric constraints around the neurite (e.g., structural barriers), which growth characteristics are affected, the presence of other guidance cues, the strength of the physical guidance cue, the spatial and/or temporal nature of the physical guidance cue, etc. In embodiments, in which more than one neurite is present, the manner, in which, a physical guidance cue alters neurite growth and/or the result of growth alteration for one neurite may be different from another neurite. In some cases, the manner and result may be substantially the same. Thus, the result of neurite growth alteration may vary according to the embodiment.

For instance, in some embodiments, altering neurite growth may involve affecting growth of the neurite, such that at least one growth characteristic is different from the natural growth characteristics of the neurite. In certain embodiments, altering neurite growth may result in control over one or more growth characteristics (e.g. neurite length, growth direction, growth velocity). In one example, a physical guidance cue may dictate the growth rate of a neurite and may reversibly inhibit or arresting growth, e.g., as illustrated in FIGS. 1A-B. In another example, as illustrated in FIG. 1E, a physical guidance cue may enhance (e.g., accelerate) the growth rate of a neurite. In some embodiments, the influence of the physical guidance cue on growth rate may be quantified by comparing the extension length of a neurites grown in the presence of a physical guidance cue to the extension length of a neurites grown under essentially identical conditions in the absence of a physical guidance cue. For instance, in embodiments in which the physical guidance cue inhibits or arrests growth, the ratio of the extension length of the neurite grown in the presence of a physical guidance cue (e.g., non-contact physical guidance cue) to the extension length of the neurite grown in the absence of a physical guidance cue is less than or equal to about 1:1, less than or equal to about 0.8:1, less than or equal to about 0.6:1, less than or equal to about 0.5:1, less than or equal to about 0.4:1, less than or equal to about 0.2:1, or less than or equal to about 0.1:1.

In embodiments in which the physical guidance cue enhances growth, the ratio of the extension length of the neurite grown in the presence of a physical guidance cue (e.g., non-contact physical guidance cue) to the extension length of the neurite grown in the absence of a physical guidance cue may be greater than or equal to about 1:1, greater than or equal to about 1.2:1, greater than or equal to about 1.3:1, greater than or equal to about 1:5, greater than or equal to about 1.8:1, greater than or equal to about 2:1, greater than or equal to about 3:1, greater than or equal to about 4:1, greater than or equal to about 5:1, greater than or equal to about 6:1, greater than or equal to about 7:1, or greater than or equal to about 8:1. In some embodiments, the ratio may be less than or equal to about 10:1, less than or equal to about 9:1, less than or equal to about 8:1, less than or equal to about 7:1, less than or equal to about 6:1, less than or equal to about 5:1, less than or equal to about 4:1, or less than or equal to about 2:1. All combinations of the above referenced ranges are possible (e.g., greater than or equal to about 1.2:1 and less than or equal to about 10:1, greater than or equal to about 1.5:1 and less than or equal to about 10:1, greater than or equal to about 2:1 and less than or equal to about 10:1). Extension length of neurite may be determined as described in Example 12.

In some embodiments, a physical guidance cue may alter growth by giving the neurite a particular directionality or orientation. For instance, in some embodiments, the physical guidance cue may be an electric field region that repels growth in the electric field region. In some such embodiments, a neurite growing (e.g., elongating) toward the electric field region may change its direction of growth to avoid the electric field region, such that the neurite has a non-zero relative change in growth angle before and after encountering the electric field region. For example, as shown in FIG. 17A, a neurite may have a first growth direction 202A before encountering the electric field region and a second growth direction 202B after encountering the electric field region. The angle formed by the first growth direction and the second growth direction may be non-zero. In some embodiments, the average relative change in growth angle before and after encountering the electric field region of a plurality of neurites may be non-zero. By contrast, in some embodiments, the average relative change in growth angle for a plurality of neurites in the absence of a physical guidance cue (e.g., control region of FIG. 17A) may be zero and/or have a significantly lower a magnitude than neurites that encounter the physical guidance cue.

For instance, in some embodiments, the magnitude of the average relative change in growth angle for a plurality of neurites before and after encountering the physical guidance cue (e.g., alternating current electric field) may be greater than or equal to about 10 degrees, greater than or equal to about 15 degrees, greater than or equal to about 25 degrees, greater than or equal to about 30 degrees, greater than or equal to about 45 degrees, greater than or equal to about 60 degrees, or greater than or equal to about 75 degrees. In some instances, the magnitude of the average relative change in growth angle for a plurality of neurites before and after encountering the physical guidance cue (e.g., alternating current electric field) may be less than or equal to about 90 degrees, less than or equal to about 85 degrees, less than or equal to about 80 degrees, less than or equal to about 75 degrees, less than or equal to about 60 degrees, or less than or equal to about 45 degrees. All combinations of the above references ranges are also possible (e.g., greater than or equal to 30 degrees and less than or equal to about 90 degrees, greater than or equal to 45 degrees and less than or equal to about 90 degrees).

In some embodiments, the magnitude of the average relative change in growth angle may increase significantly above a certain magnitude of the electric field. For example, in some embodiments, the magnitude of the average relative change in growth angle may be greater than or equal to 45 degrees when the magnitude of the electric field is greater than or equal to about 100 V/m in the vicinity of the neurites.

Figure 20:
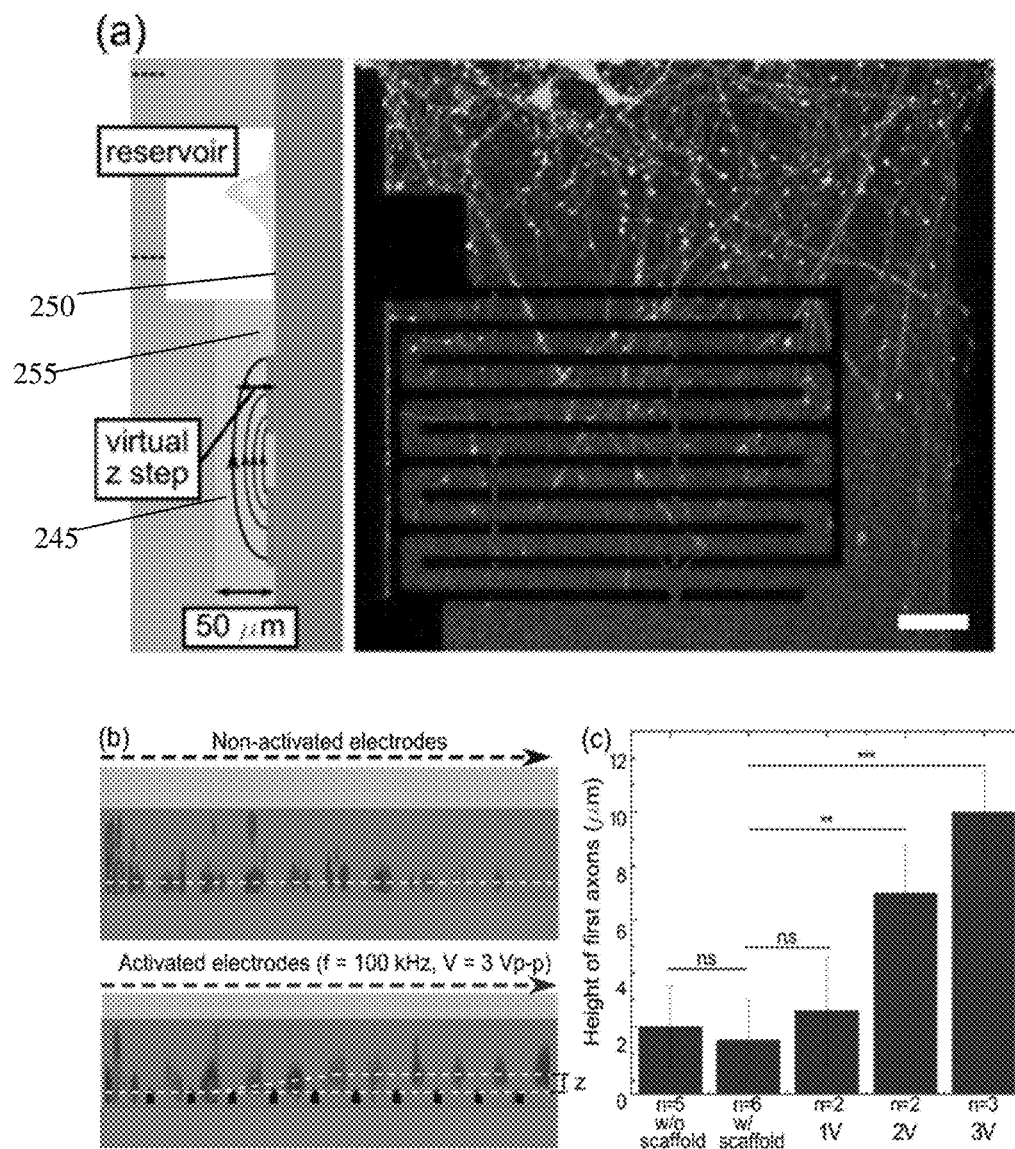
FIGS. 20A-C illustrate certain embodiments of the invention generally directed toward changing the orientation of a neurite.

In some instances, a physical guidance cue may directionally guide neurite elongation along a particular path in one-, two-, or three-dimensional space. In some instances, directionally guiding a neurite involves guiding the neurite growth in a prescribed direction. For example, as illustrated in FIG. 20A, a physical guidance cue 245 (e.g., non-mechanically actuated physical guidance cue) may be applied to a neurite growing in a first orientation 250 on the xy plane and cause the neurite to grow in a second orientation 255, e.g., in the z direction (i.e. xz plane or yz plane).

In certain embodiments, a physical guidance cue may affect the growth of a neurite multi-directionally, such that growth is altered in more than one direction. In some instance, neurite growth may be altered more than one time. In general, neurite growth may be altered any suitable number of times. For instance, a device may comprise a plurality of physical guidance cues that influence neurite growth in the same or different ways. For example, a device for forming a neuronal connection may comprise a physical guidance cue that confines neurites and/or accelerates neurite elongation as well as a physical guidance cue that changes the orientation of neurites from a first orientation (e.g., xy plane) to a second orientation (e.g., yz or xz plane). In some embodiments, multiple alterations in neurite growth may be used to allow a first population of neurites to overlap a second population of neurites without forming a neural connection.

In some embodiments, the physical guidance cue may be continuous. For instance, the cue may continually alter the growth of the neurite throughout the application. It should be understood that continual guidance is not necessarily equivalent to static guidance, as the manner and/or result of growth alteration may change over time and/or space. In certain embodiments, the physical guidance cue may be discontinuous, such that the cue varies across time and/or in space. For example, an alternating current electrical field (e.g., alternating current non-uniform electrical field) may be used to reversibly arrest neurite growth by switching the voltage between an electrode pair on and off. In another example, an array of electrode pairs may be used to dynamically guide elongation by providing local electric fields which vary in time and space.

In some embodiments, one or more physical guidance cue may be produced by an electric field. The electric field may be an alternating current electric field, such as a non-uniform alternating current electric field, or a direct current electric field. In general any type of electric field may be used. However, in certain embodiments (e.g., when the proximity of the electrodes is close, when the voltages are high), a DC electric field may not be used due to the risk of electrolysis and/or the large extent of joule heating, which may be harmful to the neuron and/or the electrodes. In some such embodiments, a non-uniform alternating current electric field can overcome the problems with DC electric fields because the high frequencies can minimize harmful electrochemical reactions and reduce the extent of joule heating. In some embodiment, a non-uniform alternating current electric field may be necessary to produce the desired physical cue, instead of, e.g., a uniform alternating current electric field or a DC electric field.

In general, an electric field may produce a physical guidance cue by a variety of mechanisms. Without being bound by theory, it is believes that electrokinetic phenomena may play an important role in the generation of a physical guidance cue. In certain embodiments, electrokinetic phenomena cause electrokinetic forces to be exerted on the neurite and/or its surrounding environment. The characteristics of these forces (e.g., origin, type, magnitude, direction) may dictate the manner, in which, a physical guidance cue alters neurite growth. For example, a perpendicular electrokinetic force may cause growth arrest whereas a non-perpendicular force may cause the neurite to change its orientation. In certain embodiments, the electrokinetic phenomena and resulting forces may differ for alternating current (AC) electric fields and direct current (DC) electric fields. In other embodiments, the electrokinetic phenomena and resulting forces for AC and DC fields may be substantially the same.

In some embodiments, certain properties of the electric field (e.g., magnitude, frequency) may influence the properties of the physical guidance cue and thereby influence alteration of neurite growth. For example, an AC field with a lower frequency may cause greater inhibition of neurite growth than an AC fields with higher frequency at a given voltage. In certain embodiments, the alternating current electric field with a certain range of frequencies may be used. For instance, in some embodiments, the frequency of the AC electric field may be greater than or equal to about 100 Hz, greater than or equal to about 500 Hz, greater than or equal to about 1,000 Hz, greater than or equal to about 5,000 Hz, greater than or equal to about 10,000 Hz, greater than or equal to about 50,000 Hz, greater than or equal to about 100,000 Hz, or greater than or equal to about 500,000 Hz. In some instances, the frequency of the alternating current electric field may be less than or equal to about 1,000,000 Hz, less than or equal to about 500,000 Hz, less than or equal to about 100,000 Hz, less than or equal to about 50,000 Hz, less than or equal to about 10,000 Hz, less than or equal to about 5,000 Hz, less than or equal to about 1,000 Hz, or less than or equal to about 500 Hz. Combination of the above-referenced ranges are also possible (e.g., greater than or equal to about 100 Hz and less than or equal to about 1,000,000 Hz). Other values are also possible.

In some embodiments, the magnitude of the electric field may influence properties of the physical guidance cue. In one example, a threshold value may exist for the generation of a physical guidance cue, such that a physical guidance cue may not be generated below a certain magnitude. In general, the magnitude of the electric field may be selected as desired. For instance, in some embodiments, magnitude of the electric field may be greater than or equal to about 50 V/m, greater than or equal to about 100 V/m, greater than or equal to about 200 V/m, greater than or equal to about 500 V/m, greater than or equal to about 1,000 V/m, greater than or equal to about 5,000 V/m, greater than or equal to about 10,000 V/m, greater than or equal to about 50,000 V/m, greater than or equal to about 100,000 V/m, or greater than or equal to about 500,000 V/m. In some instance, the magnitude of the electric field may be less than or equal to about 1,000,000 V/m, less than or equal to about 500,000 V/m, less than or equal to about 100,000 V/m, less than or equal to about 50,000 V/m, less than or equal to about 10,000 V/m, less than or equal to about 5,000 V/m, less than or equal to about 1,000 V/m, less than or equal to about 500 V/m, greater than or equal to about 200 V/m. Combination of the above-referenced ranges are also possible (e.g., greater than or equal to about 100 V/m and less than or equal to about 1,000,000 V/m). Other values are also possible.

In certain embodiments, the proximity of the electrodes which produce the electric field may influence properties of the physical guidance cue (e.g., localization to a vicinity; manner, in which, growth is altered). For example, an electrode pair with a small center to center spacing (e.g., 1 micron) may be able to apply an electric field that is localized to the growth cone of a neurite, whereas an electrode pair with a larger center to center (e.g., greater than 200 microns) spacing may not be able to apply a localized electric field. In general, the center to center spacing on the electrodes may be selected to achieve the desired results. For instance, in some embodiments, the center to center spacing between electrodes may be less than 200 microns, less than or equal to about 150 microns, less than or equal to about 125 microns, less than or equal to about 100 microns, less than or equal to about 75 microns, less than or equal to about 50 microns, less than or equal to about 30 microns, less than or equal to about 10 microns, or less than or equal to about 1 micron. In some instances, the center to center spacing between electrodes may be greater than or equal to about 0.1 micron, greater than or equal to about 1 micron, greater than or equal to about 5 microns, greater than or equal to about 15 microns, greater than or equal to about 30 microns, greater than or equal to about 60 microns, greater than or equal to about 100 microns, greater than or equal to about 140 microns, or greater than or equal to about 180 microns. Combination of the above-referenced ranges are also possible (e.g., greater than or equal to about 1 micron and less than or equal to about 100 microns). Other values are also possible.

In certain embodiments, the presence of other guidance cues may influence properties of the physical guidance cue. For instance, in some embodiments, the physical guidance cue may directionally guide a neurite along a path that has a barrier to growth due to another guidance cue (e.g., mechanical guidance cue). In some embodiments, the force of the other guidance cue may be proportional to or greater than the physical guidance cue, such that neurite growth along the path is inhibited or arrested. In certain embodiments, the physical guidance cue may change the orientation of a neurite to a path that has a greater effective probing area than the original orientation. In some such embodiments, neurite growth (e.g., elongation) may be inhibited or slowed relative to neurites growing in the original orientation in the absence of a physical guidance cue. For example, a neurite growing in a first orientation in a three dimension scaffold comprising fibers (e.g., collagen fibers) aligned in the first orientation may provide a track-line mechanical guidance cue that promotes neurite growth. In some such embodiments, neurites may grow slower in the second orientation relative to the first orientation.

Figure 2A:
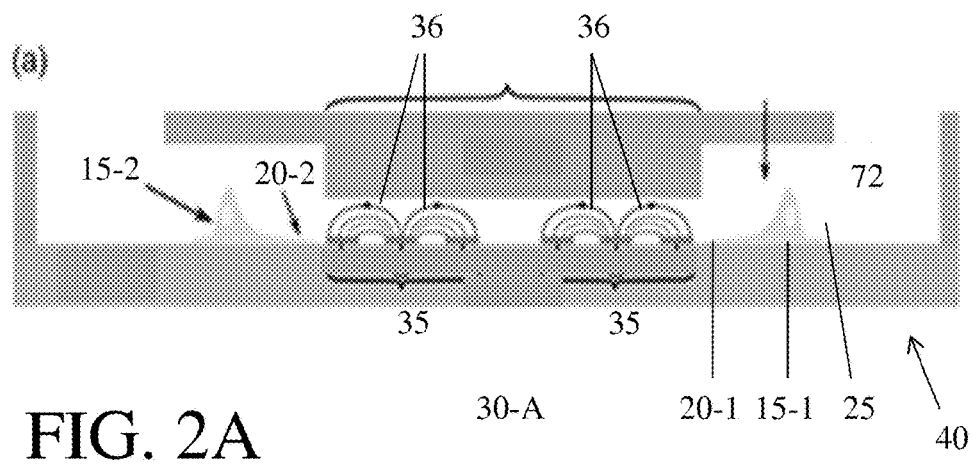
FIGS. 2A-D illustrate certain embodiments of the invention generally directed toward forming neural connections.

As described herein, one or more physical guidance cues may be used to alter the growth of neurites from more than one neuron. In embodiments, in which more than one neuron, each having at least one neurite, is present, reconfigurable physical guidance cues may be used to form directional neural connections, such as axon diodes, neural circuits, and neural networks. An example of a device 40 for forming directional neural connections using a reconfigurable physical guidance cue is shown in FIG. 2A. In some embodiments, device 40 may be similar to device 10. As shown illustratively in FIG. 2A, device, shown in cross-section, 40 may contain a neuron 15, having a first neurite 20-1, located in a chamber 25 and a second neuron 15-2, having a second neurite 20-2, located in chamber 25-2. The device may include a plurality of chambers (e.g., 25 and 25-2), which are capable of housing a living cell and promoting cell growth, at least one channel (e.g., 30A), which connects two chambers and in which neurites from each neuron can grow, and electrodes 35 that are capable of generating a physical guidance cue. The electrodes 35 may be arranged in pairs. For example, three electrodes may be arranged to form two electrode pairs and each electrode pair may produce an electric field 36, which generates one or more physical guidance cues. In certain embodiments, each electrode pair may function as a gate with a lock. The gate may be closed (i.e., locked) when a voltage is applied across the electrodes, and open in the absence of a voltage. In some instances, as illustrated in FIG. 2A, electrode pairs intersect the channel near the chambers. In other instances, the intersection position of the electrodes with the channels may vary, as well as the number of electrode pairs present. For example, two or more electrode pairs may intersect a channel at any point along its length. In general, the position of the electrode pairs may be selected as desired. The chambers and channels may also be configured such that the neuron cell bodies and are confined to the chamber, while neurites may grow into each channel.

Figure 2B:
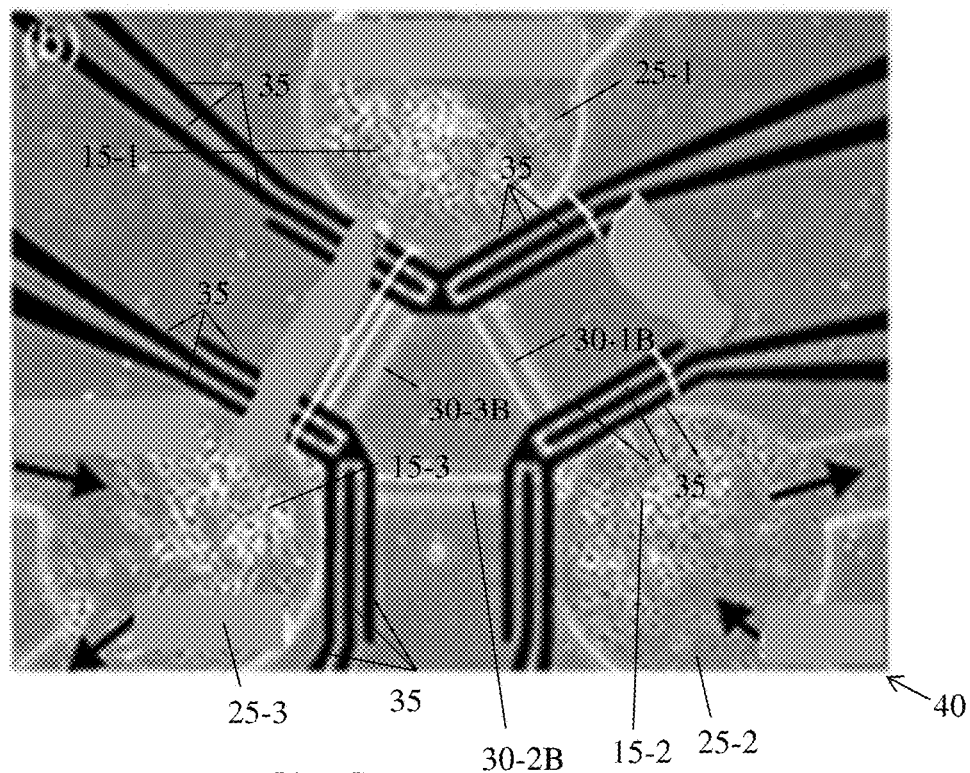
Figure 2C:
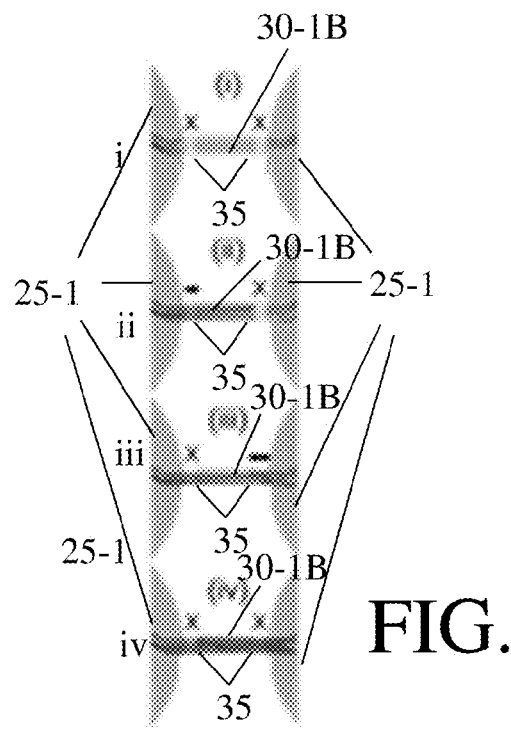

An example of formation of a directional neural connection using one or more reconfigurable physical guidance cues is shown in FIGS. 2B-C. As shown illustratively in FIG. 2B, device, shown in plan view, 40 may contain a first neuron 15-1, a second neuron 15-2, and a third neuron 15-3 housed in a first chamber 25-1, a second chamber 25-2, and a third chamber 25-3, respectively. The device may include a first channel 30-1B, a second channel 30-2B, and a third channel 30-3B, in which neurites may grow, respectively. In some embodiments, as shown in FIG. 2B, the device is configured such that each chamber is connected to another chamber by a single channel, such that each chamber is connected to two channels. In other cases, each chamber may be connected to another chamber by more than one channel. As shown in FIG. 2B, three electrodes (i.e., two gates) may intersect each channels near the chambers.

Figure 2D:
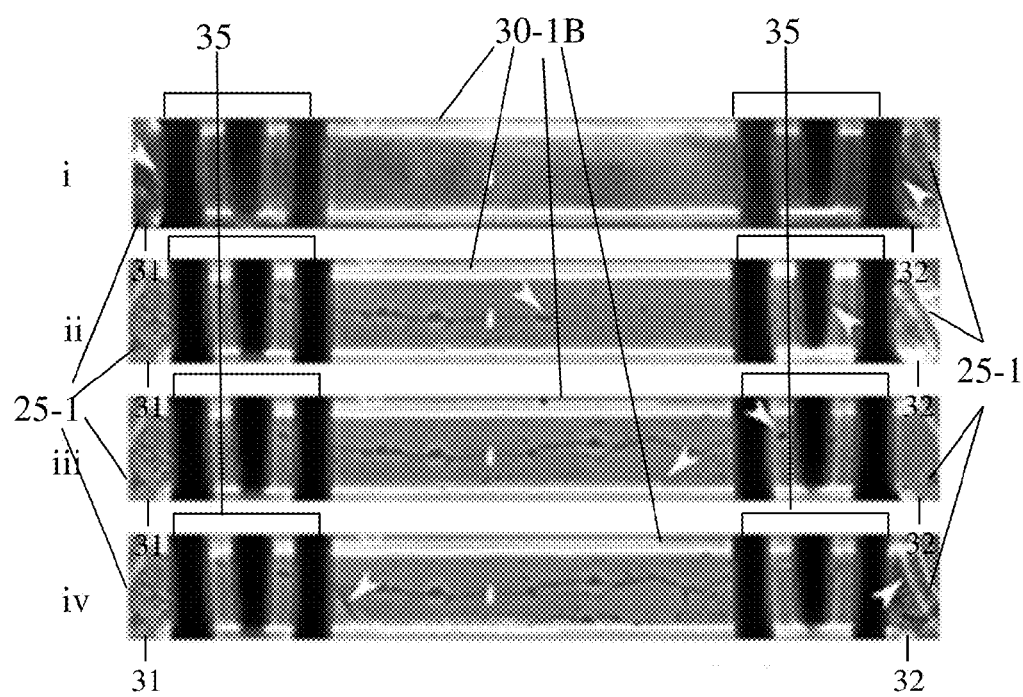

A method for forming a directional neural connection in a channel (e.g., an axon diode) using device 40, according to one set of embodiments, is shown in FIG. 2C-D. FIG. 2C shows the presence, as indicated by the "x", or absence, as indicated by the dash, of an electric field for each image of the axon diode system in FIG. 2D. As shown in FIGS. 2Ci and 2Di, axon diode formation begins when a neurite enters each terminal end, 31 and 32, of a channel (e.g., 30-1B). Two electrode pairs (i.e., three electrodes) are positioned near each terminal end and serve as gates. To form a unidirectional connection, a voltage may be applied to a gate at each terminal end to lock the gate. In some embodiments, the directionality of the neural connection is defined by which gate is opened first (i.e., removal of the voltage). For example, as shown in FIGS. 2Cii and 2Dii, a voltage is applied to electrodes near terminal end 32. In some cases, the electric field generates a physical guidance cue in the vicinity of the electrode pair that reversibly arrests or inhibits neural outgrowth. A voltage is not applied to the electrodes near terminal end 31, such that the neuron may grow through the channel. The growth cone of the neuron is indicated by the white arrow. Once the growth cone of the neurite is past both gates near 31 and approaches the gates near 32, the gates near terminal end 32 is turned opened and gates near terminal end 31 are turned locked as shown in FIGS. 2Ciii and 2Diii. In some embodiments, the gates near terminal end 31 are locked preventing other neurites from growing in the channel. In addition, the gates near terminal end 32 are opened to allow the neurite connect. In certain embodiments, after axon diode formation, all gates are locked to prevent other neurites from entering the channel. In some embodiments, this method of opening and closing gates may be repeated to form additional neural connections.

Figure 3:
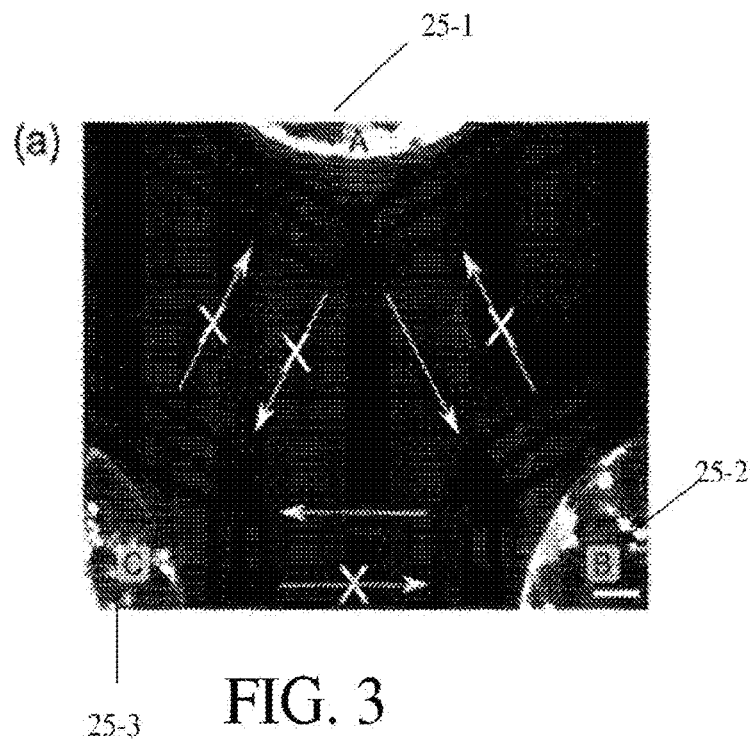
FIG. 3A illustrates a neural network in accordance with one embodiment of the invention.

An example of the formation of a directional neural network using one or more reconfigurable physical guidance cue is shown in FIG. 3. In some embodiments, device 40 may be used to form neural networks. To form neural networks, the gate were opened and closed, as in the example above, such that neural connections were formed between chambers 25-1 and 25-2 and chambers 25-2 and 25-3. A connection was not formed between chambers 25-1 and 25-3, as indicated by the arrow with an "X" in FIG. 3. In certain embodiments, the connections may be uni-directional, as shown in FIG. 3. The direction of the connection is indicated by arrows and the lack of a directional connection in the opposite direction is indicated by the arrow with an "X".

In some embodiments, one or more guidance cues (e.g., physical and contactless guidance cue) may be used to guide neurite growth in two and or three dimensions and form complex neural networks. For instance, in some embodiments, one or more guidance cues may be used to causing a first neurite or population of neurites to overlap a second neurite or population of neurites, e.g., using a guidance cue (e.g., physical and contactless guidance cue). In some such embodiments, the use of one or more guidance cue allows neurites to overlap without forming a neural connection or forming relatively few neural connections in the overlap region. For instance, in some embodiments, the percentage of neurites in the first population that form a connection with a neurite in the second population at the overlap region may be less than or equal to about 10%, less than or equal to about 8%, less than or equal to about 5%, less than or equal to about 3%, less than or equal to about 2%, less than or equal to about 1%, less than or equal to about 0.75%, less than or equal to about 0.5%, less than or equal to about 0.25%, less than or equal to about 0.1%, less than or equal to about 0.05%, less than or equal to about 0.01%, or less than or equal to about 0.001%.

In certain embodiments, the first population of neurites may overlap the second population of neurites within a three-dimensional scaffold. In some such cases, the guidance cue may be a non-contact physical guidance cue (e.g., electric field). In some embodiments, the object used to produce the guidance cue may not be contained within the three-dimensional scaffold. For instance, in embodiments in which the guidance cue is an electric field, the electrodes used to produce the electric field may not be contained within the scaffold. In other embodiments, the electrodes used to produce the electric field may be contained within the scaffold.

Figure 21A:
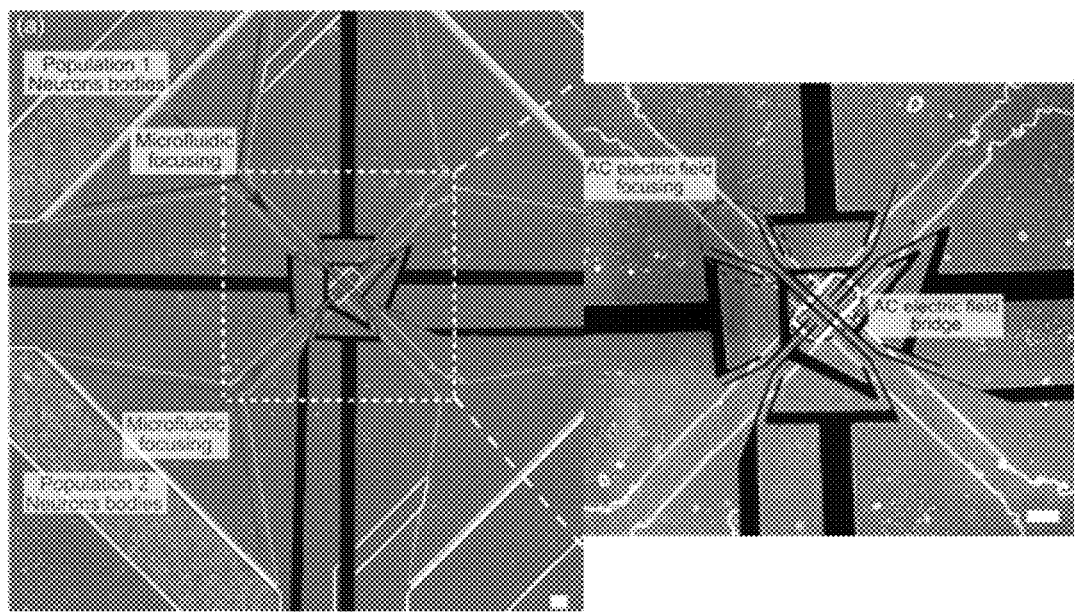
Figure 21F:
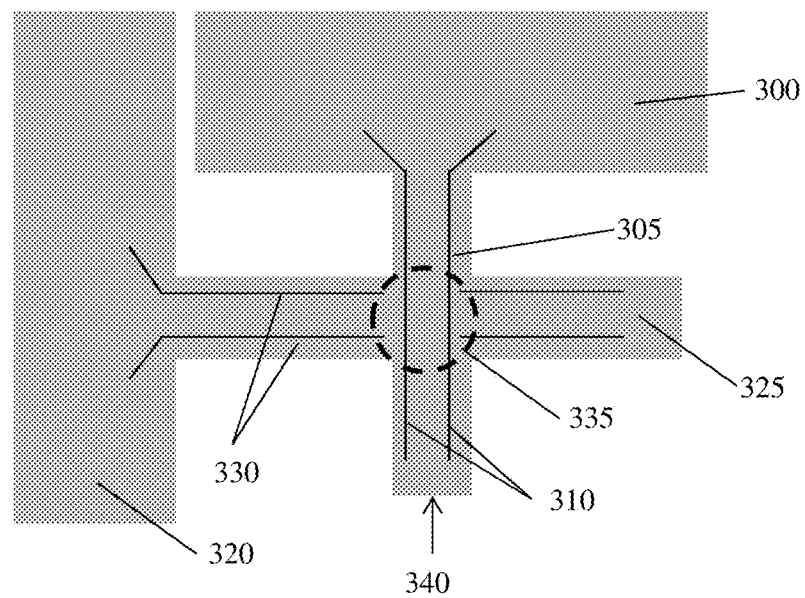

A non-limiting example of a device for forming a region where two or more neurites overlap is shown in FIG. 21F. In some embodiments, the device may contain a first chamber 300 that is adapted and arranged to house one or more living cell and promote cell growth and that is connected to a first channel 305. The device may also contain a first electrode pair 310 aligned with at least a portion of the first channel, such that a portion of the first electrode pair overlaps with at least a portion of the first chamber. In certain cases, at least one electrode (e.g., each of the electrodes) in the first electrode pair may form a pair with another electrode that also overlaps with at least a portion of the first chamber as illustrated in FIG. 1E. The device may also a second chamber 320 that is adapted and arranged to house one or more living cell and promote cell growth and that is connected to a second channel 325. In some instances, the device contains a second electrode pair 330 aligned with at least a portion of the second channel. At least a portion of the second electrode pair may overlap with at least a portion of the second chamber. In certain cases, at least one electrode (e.g., each of the electrodes) in the second electrode pair may form a pair with another electrode that also overlaps with at least a portion of the first chamber as illustrated in FIG. 1E. In some embodiments, the height of the channel in the overlap region may be sufficiently high to allow neurite growth in three dimensions, as described in more detail below. For instances, the first and second channels may intersect at an overlap region having a height of greater than about 20 microns and less than or equal to about 1000 microns (e.g. greater than about 20 microns and less than or equal to about 500 microns, greater than or equal to about 50 microns and less than or equal to about 1000 microns, greater than about 20 microns, greater than or equal to about 50 microns). In some embodiments, at least a portion of the first and the second channels may be filled with a three-dimensional scaffold, as described in more detail below. In some instances the entire first and second channel may be filled with the three-dimensional scaffold.

In some embodiments, as illustrated in FIG. 21F, the second electrode pair may be discontinuous in the portion of the second channel that overlaps with the first channel. In some such cases, the second electrode pair may have a gap 335 that allows the first electrode pair to cross the region where the channels intersect with intersecting or overlapping at least one of the second pair of electrodes.

In certain embodiments, a device may be used to cause neurites to overlap without forming a neural connection. In some embodiments, one or more neurons (e.g., first population of neurons) are seeded in the first chamber and one or more neurons (e.g., second population) are seeded in the second chamber. The channels may be filled with a three-dimensional scaffold, such that neurite elongation within the channel occurs in the scaffold. In some embodiments, the portion of the electrodes that overlap with the first chamber may guide neurites elongating toward the first channel into the region between the electrode pair. In some instances, the neurites that elongate into the within the scaffold region between the electrodes may be inhibited crosses one or more electrode in the electrode pair. Without being bound by theory, it is believed that electric field around the edges of the electrode inhibit and prevent neurites from elongating in the region outside of the electrode pair. In some such cases, the neurites are confined to elongate within the scaffold region between the electrodes and, in some instances, in a direction substantially parallel to one or more electrode. In some embodiments, the first electrode pair serves directionally guide at least a portion of the neurites from the first chamber to the end of the first electrode pair (e.g., location 340). It should be understood the electrodes may not be within the three dimensional scaffold and that the region between the electrodes may refers to the three-dimensional space that is between the electrode but not necessarily direct physically touching the electrodes.

The portion of the electrodes that overlap with the second chamber may also guide neurites elongating toward the second channel into the region between the electrode pair and confine growth of the neurites to the region between the electrodes. In some embodiments, the neurites in the second channel may elongate to the overlap region and encounter the electric field (e.g., alternating current electrical field) from the first electrode pair. The electrical field produced by the first pair of electrodes may inhibit neurite growth in the high electric field regions (e.g., where the magnitude of the electric field from the first electrode is greater than or equal to about 100 V/m). In certain embodiments, the neurites in the second channel may change orientation to circumvent the high electric field region produced by the first pair of electrodes. For instance, the neurites may change the z-axis component of their orientation to circumvent the high electric field as illustrated in FIG. 20A. Without being bound by theory, it is believed that the z-axis change prevents contact between the neurites in the first channel and the neurites in the second channel and therefore prevents the formation of neural connections. In certain embodiments, the portions of the second electrode pair may continue to influence the x-axis and y-axis components of the elongation direction of the neurites over the first electrodes. In some such embodiments, after the neurites elongate past the first electrode pair, the neurites are re-funneled into and/or continue to elongate in the region between the second pair of electrodes.

In some embodiments, one or more guidance cues may be used to directionally guide elongation of a first and a second population of neurites to form a neural network between the first and second population of neurites using a guidance cue (e.g., physical guidance cue). In certain embodiments, one or more guidance cues may be used to directionally guide neurite elongation within a three-dimensional scaffold of the first and second population of neurites to form the neural network. In some such cases, the guidance cue may be a non-contact physical guidance cue (e.g., electric field). In some embodiments, the object used to produce the guidance cue may not be contained within the three-dimensional scaffold. For instance, in embodiments in which the guidance cue is an electric field, the electrodes used to produce the electric field may not be contained within the scaffold. In other embodiments, the electrodes used to produce the electric field may be contained within the scaffold.

Figure 21G:
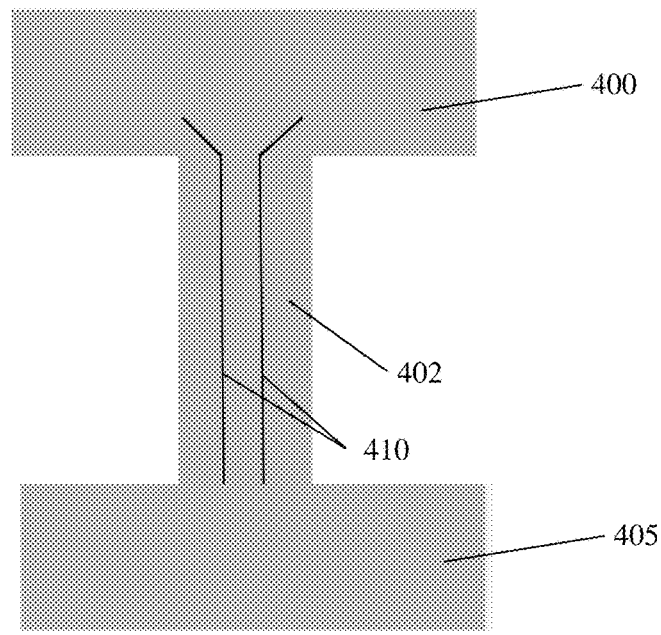

A non-limiting example of a device for forming a region where two or more neurites overlap is shown in FIG. 21G. In some embodiments, the device may contain a channel 402 connected to a first chamber 400 and a second chamber 405 that are adapted and arranged to house one or more living cell and promote cell growth. The device may also comprise a first electrode pair 410 aligned with at least a portion of the first channel. The first electrode pair may overlaps with at least a portion of the first chamber and wherein a center to center spacing between the first electrode pair is less than or equal to about 200 microns (e.g., less than or equal to about 150 microns, less than or equal to about 100 microns, less than or equal to about 50 microns). In certain embodiments, first electrode pair may overlaps with at least a portion of the second chamber. In some embodiments, at least a portion of the first channel may be filled with a three-dimensional scaffold. In some instances the entire first channel may be filled with the three-dimensional scaffold, such that elongation of the neurite occurs within the scaffold. In certain cases, at least one electrode (e.g., each of the electrodes) in the first electrode pair may form a pair with another electrode that also overlaps with at least a portion of the first chamber as illustrated in FIG. 1E.

In certain embodiments, the device may be used to directionally guide elongation of neurites to form a neural network between the neurites using a guidance cue (e.g., alternating current electric field). In some embodiments, one or more neurons (e.g., first population of neurons) are seeded in the first chamber and one or more neurons (e.g., second population) are seeded in the second chamber. The channels may be filled with a three-dimensional scaffold, such that neurite elongation within the channel occurs in the scaffold. In some embodiments, the portion of the electrodes that overlap with the first chamber may guide neurites elongating toward the first channel into the region between the electrode pair. In some embodiments, the one or more neurites elongating from one or more neurons in the second chamber may elongate within the region between the first electrode pair. In embodiments in which a portion of the first electrodes overlaps with the second chamber, the portion of the first electrodes that overlap with the second chamber may also guide neurites elongating toward into the region between the electrode pair and confine growth of the neurites to the region between the electrodes. In some embodiments, the one or more neurites elongating from the first and one or more neurites elongating from the second chambers in the first channel may meet in the first channel and form a neural network.

In general, a neurite from any suitable neuron can be overlapped with or form neural connections with neurite from any other suitable neuron. It should be understood that neurites from different neurons (e.g., different cell bodies, different neuron type, different class of neurons, etc.) or the same neurons (e.g., different cell bodies, different neuron type, different class of neurons, etc.) may be used.

Figure 4:
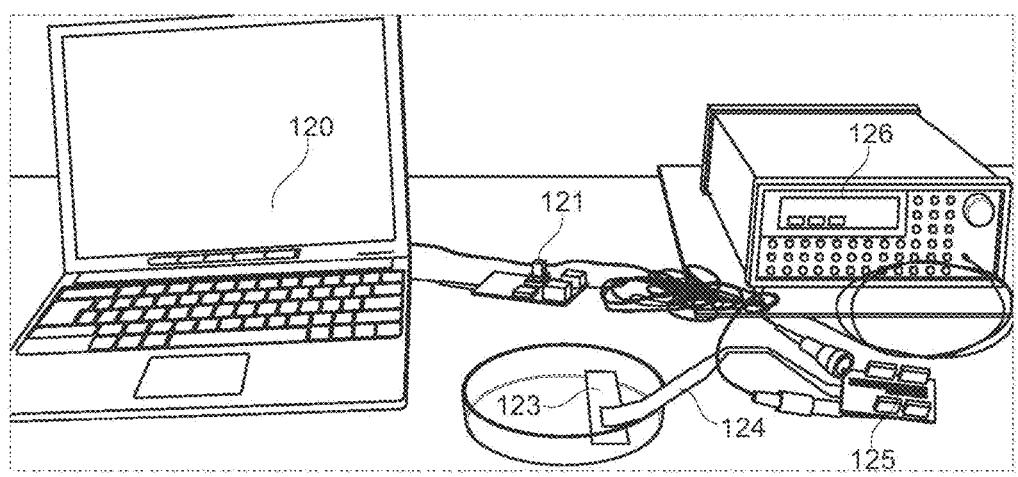
FIG. 4 illustrates an electrical system in accordance with various embodiments of the invention.

As described herein, an electrical signal may be applied to devices able to culture living cells (e.g., neurons). In some embodiments, the devices may need to be placed in an environment conducive to the maintenance and growth of living cell (e.g., in an incubator) and be attached to a system that allows electrical signals to be applied to the device. A system able to provide electrical signals to a device, as described herein, while in an environment conducive for cell maintenance and growth is shown in FIG. 4. In some embodiments, as shown in FIG. 4, an electrical signal may be applied to a device on a chip 123 using a connector 124 that is linked to a circuit-board stack 125, which can generate an electrical signal and reroute and/or maintain an electrical signal to one or more electrodes. In certain embodiments, the stack 125 may be connected to a minicomputer 121, which pilots the entire stack. In some cases, the minicomputer may autonomously control the operations of the stack (e.g., the application and maintenance of electrical signal across electrodes in the device). In some instances, devices, such as web servers, may be installed on the minicomputer so that the parameters (e.g., voltage, frequency) for each electrode can be remotely changed (e.g., via the internet 120, via remote computer connection, etc.) in real time.

As described herein, devices including channels, chambers, and electrodes amongst other components may be used in the alteration of neurite growth and formation of neural connection using physical guidance cues. In some embodiments, the features (e.g., dimension, fabrication materials, arrangement) of the device components may influence the operation of the device. For example, in order to alter neurite growth, the devices may have one or more microscale components (e.g., chambers, channels, electrodes). In certain cases, the device may be a microfluidic device. In general, the feature of the device components may be selected as desired.

In some embodiments, the intersection angle of an electrode with a channel or channel may be greater than or equal to about 0° C., greater than or equal to about 15° C., greater than or equal to about 45° C., greater than or equal to about 90° C., greater than or equal to about 135° C., or greater than or equal to about 150° C. In some instances, the angle may be less than or equal to about 180° C., less than or equal to about 150° C., less than or equal to about 115° C., less than or equal to about 90° C., less than or equal to about 60° C., or less than or equal to about 30° C. Combinations of the above-referenced ranges are also possible (e.g., less than or equal to about 0° C. and less than or equal to about 135° C.). Other values are also possible. In certain embodiments, an electrode may intersect a channel at a different angle than another electrode. Conversely, an electrode may intersect a channel at substantially the same angle as another electrode. In some instances, an electrode may intersect a channel at a different angle than another channel. In other instances, an electrode may intersect a channel at the same angle as another channel.

In some embodiments, the dimensions of the chambers may be selected as desired. It should be understood that a chamber can have any suitable cross-sectional dimension. For instance, in some embodiments, chamber may have a maximum cross-sectional dimension of less than or equal to about 2,000 microns, less than or equal to about 1,000 microns, less than or equal to about 750 microns, less than or equal to about 600 microns, less than or equal to about 500 microns, less than or equal to about 300 microns, less than or equal to about 200 microns, less than or equal to about 100 microns, less than or equal to about 50 microns, less than or equal to about 25 microns, less than or equal to about 10 microns, or less than or equal to about 5 microns. In some instances, a chamber, may have a maximum cross-sectional dimension of greater than or equal to about 0.01 microns, greater than or equal to about 0.1 microns, greater than or equal to about 1 microns, greater than or equal to about 5 microns, greater than or equal to about 10 microns, greater than or equal to about 20 microns, greater than or equal to about 50 microns, greater than or equal to about 100 microns, greater than or equal to about 200 microns, greater than or equal to about 400 microns, greater than or equal to about 600 microns, greater than or equal to about 900 microns, or greater than or equal to about 1,500 microns. Combinations of the above-referenced ranges are also possible (e.g., greater than or equal to about 1 micron and less than or equal to about 1,000 microns). Other values of maximum cross-sectional dimensions are also possible.

In some cases, at least one or at least two cross-sectional dimensions (e.g., a height and a width) of chamber may be less than or equal to about 750 microns, less than or equal to about 500 microns, less than or equal to about 300 microns, less than or equal to about 200 microns, less than or equal to about 100 microns, less than or equal to about 50 microns, less than or equal to about 20 microns, less than or equal to about 10 microns, or less than or equal to about 5 microns. In some instances, at least one or at least two cross-sectional dimensions of chamber may be greater than or equal to about 0.01 microns, greater than or equal to about 0.1 microns, greater than or equal to about 1 micron, greater than or equal to about 5 microns, greater than or equal to about 10 microns, greater than or equal to about 25 microns, greater than or equal to about 50 microns, greater than or equal to about 100 microns, greater than or equal to about 200 microns, greater than or equal to about 400 microns, or greater than or equal to about 600 microns. Combinations of the above-referenced ranges are also possible (e.g., greater than or equal to about 10 μm and less than or equal to about 500 μm). Other values are also possible.

A chamber may have a certain width-to-height ratio. In certain instances, the ratio of the width to height of chamber may be greater than or equal to about 1:1, greater than or equal to about 2:1, greater than or equal to about 5:1, greater than or equal to about 10:1, greater than or equal to about 15:1, greater than or equal to about 20:1, greater than or equal to about 50:1, greater than or equal to about 100:1, greater than or equal to about 200:1, greater than or equal to about 300:1, or greater than or equal to about 400:1. In some instances the width-to-height ratio may be less than or equal to about 500:1, less than or equal to about 400:1, less than or equal to about 300:1, less than or equal to about 200:1, less than or equal to about 100:1, less than or equal to about 50:1, less than or equal to about 20:1, less than or equal to about 15:1, less than or equal to about 10:1, less than or equal to about 5:1, or less than or equal to about 2:1. Combinations of the above-referenced ranges are also possible (e.g., greater than or equal to about 1:1 and less than or equal to about 20:1). Other values are also possible.

A chamber may also have an aspect ratio (length to largest average cross-sectional dimension) of at least 2:1, more typically at least 3:1, 8:1, or 20:1. In some cases, the channels, channel segments, or channel portions have very large aspect ratios, e.g., at least 100:1, 500:1 or 1000:1.

In some embodiments, a chamber may have a length of greater than or equal to about 1 mm, greater than or equal to about 5 mm, greater than or equal to about 10 mm, greater than or equal to about 20 mm, greater than or equal to about 40 mm, greater than or equal to about 60 mm, or greater than or equal to about 80 mm. In some instances, the length may be less than or equal to about 100 mm, less than or equal to about 90 mm, less than or equal to about 70 mm, less than or equal to about 50 mm, less than or equal to about 30 mm, or less than or equal to about 10 mm. Combinations of the above-referenced ranges are also possible (e.g., greater than or equal to about 1 mm and less than or equal to about 100 mm). Other values of length are also possible.

In some embodiments, the dimensions of the channel may be selected as desired. In some embodiments, the height of the channel may influence the orientation of a growing neuron in the presence or absence of an electric field. For instance, the height of the channel may cause neurite growth to be confined to a two-dimensional or three-dimensional plane. In one example, the height of the channel may be relatively small (e.g., less than or equal to about 10 microns, less than or equal to about 5 microns), such that the growth cone is spatially confined and cannot grow in the three-dimensions and is restricted, e.g., along the z direction. In some instances, the height of the of the channel may be relatively large (e.g., greater than or equal to about 50 microns, greater than or equal to about 100 microns, greater than or equal to about 200 microns, greater than or equal to about 300 microns, greater than or equal to about 1000 microns), such that the growth cone is not spatially confined and can grow in the three-dimensions.

It should be understood that a channel can have any suitable cross-sectional dimension. For instance, in some embodiments, channel may have a maximum cross-sectional dimension of less than or equal to about 1 cm, less than or equal to about 5000 microns, less than or equal to about 2000 microns, less than or equal to about 1000 microns, less than or equal to about 500 microns, less than or equal to about 300 microns, less than or equal to about 200 microns, less than or equal to about 100 microns, less than or equal to about 50 microns, less than or equal to about 25 microns, less than or equal to about 10 microns, less than or equal to about 5 microns, less than or equal to about 2 microns, or less than or equal to about 1 microns. In some instances, a channel, may have a maximum cross-sectional dimension of greater than or equal to about 0.1 microns, greater than or equal to about 1 microns, greater than or equal to about 5 microns, greater than or equal to about 10 microns, greater than or equal to about 25 microns, greater than or equal to about 50 microns, greater than or equal to about 100 microns, greater than or equal to about 200 microns, greater than or equal to about 300 microns, greater than or equal to about 500 microns, greater than or equal to about 1000 microns, greater than or equal to about 2000 microns, or greater than or equal to about 5000 microns. Combinations of the above-referenced ranges are also possible (e.g., greater than or equal to about 1 micron and less than or equal to about 2000 microns). Other values of maximum cross-sectional dimensions are also possible.

In some cases, at least one or at least two cross-sectional dimensions (e.g., height, a height and a width) of channel may be less than or equal to about 2000 microns, less than or equal to about 1000 microns, less than or equal to about 500 microns, less than or equal to about 300 microns, less than or equal to about 200 microns, less than or equal to about 100 microns, less than or equal to about 50 microns, less than or equal to about 30 microns, less than or equal to about 20 microns, less than or equal to about 10 microns, less than or equal to about 5 microns, less than or equal to about 2 microns, or less than or equal to about 1 micron. In some instances, at least one or at least two cross-sectional dimensions of channel may be greater than or equal to about 0.01 microns, greater than or equal to about 0.1 microns, greater than or equal to about 1 micron, greater than or equal to about 5 microns, greater than or equal to about 10 microns, greater than or equal to about 25 microns, greater than or equal to about 50 microns, greater than or equal to about 75 microns, greater than or equal to about 125 microns, greater than or equal to about 200 microns, greater than or equal to about 300 microns, greater than or equal to about 500 microns, or greater than or equal to about 1000 microns. Combinations of the above-referenced ranges are also possible (e.g., greater than or equal to about 0.1 microns and less than or equal to about 10 microns, greater than or equal to about 1 micron and less than or equal to about 2000 microns). Other values are also possible.

A channel may have a certain width-to-height ratio. In certain instances, the ratio of the width to height of channel may be greater than or equal to about 1:1, greater than or equal to about 1.6:1, greater than or equal to about 3:1, greater than or equal to about 5:1, greater than or equal to about 10:1, greater than or equal to about 15:1, or greater than or equal to about 20:1. In some instances the width-to-height ratio may be less than or equal to about 30:1, less than or equal to about 20:1, less than or equal to about 15:1, less than or equal to about 10:1, less than or equal to about 5:1, or less than or equal to about 2:1. Combinations of the above-referenced ranges are also possible (e.g., greater than or equal to about 1:1 and less than or equal to about 20:1). Other values are also possible.

A channel may also have an aspect ratio (length to largest average cross-sectional dimension) of at least 50:1, more typically at least 75:1, 90:1, or 150:1. In some cases, a channel may have a very large aspect ratios, e.g., at least 200:1, 500:1, 1, 000:1, or 10, 000:1.

In some embodiments, a channel may have a length of greater than or equal to about 50 microns, greater than or equal to about 100 microns, greater than or equal to about 200 microns, greater than or equal to about 400 microns, greater than or equal to about 600 microns, or greater than or equal to about 800 mm. In some instances, the length may be less than or equal to about 1,000 microns, less than or equal to about 750 microns, less than or equal to about 450 microns, less than or equal to about 250 microns, less than or equal to about 150 microns, or less than or equal to about 75 microns. Combinations of the above-referenced ranges are also possible (e.g., greater than or equal to about 100 microns and less than or equal to about 750 microns). Other values of length are also possible.

In some embodiments, at least a portion of a channel may be filled with a three dimensional scaffold. The three-dimensional scaffold may be capable of housing a living cell or portion of a living cell and promoting cell growth and development (e.g., neurite growth). In some embodiments, the three-dimensional scaffold may facilitate neurite growth in multiple dimensions (e.g., in three-dimensions). In general the scaffold may be formed from any suitable material capable of housing a living cell or portion of a living cell and promoting cell growth and development. Those of ordinary skill in the art would be aware of suitable scaffold material. Non-limiting examples of suitable scaffold material include collagen, laminin, polysaccharides, polypeptides, gel matrix, extracellular complexes (e.g., matrigel), matrix proteins (e.g., fibronectin, gelatin), hydrogels, elastin, tenascin, proteoglycans, glycosaminoglycans, growth factors, and combinations thereof.

In some embodiments, at least a portion of one surface of the channel may be functionalized with a molecule. In some embodiments, the molecule may alter the growth of the neuron and/or neurite and/or alter the attachment of the neuron and/or neurite to the portion of the surface. In some instances, the molecule may enhance (e.g., accelerate) cell body or neurite growth and/or attachment. In other instances, the molecule may reduce cell body or neurite growth and/or attachment. In certain cases, the molecule may be a chemical guidance cue. Those of ordinary skill of the art would be knowledge of suitable molecules based on the description provided herein.

In some embodiments, the neuron or living cell may be selected from the group consisting of hippocampus neurons, dorsal root ganglion, retinal ganglion neurons, Golgi I neurons, Golgi II neurons, basket cells, betz cells, lugaro cells, medium spiny neurons, purkinje cells, renshaw cells, unipolar brush cells, granule cells, anterior horn cells, motoneurons, spindle cells, pseudounipolar neurons, multipolar neurons, interneurons, motor neurons, sensory neurons, stellate cells, and combinations thereof. In general any suitable neuron may be used.

The following reference is incorporated herein by reference in its entirety for all purposes: U.S. Provisional Patent Application Ser. No. 61/752,183, filed Jan. 14, 2013, and entitled "Electrokinetic Confinement of Neurite Growth for Dynamically Configurable Neural Networks.

The following examples are intended to illustrate certain embodiments of the present invention, but do not exemplify the full scope of the invention.

EXAMPLE 1

This example describes the use of alternating current (AC) electric fields to dynamically control axonal growth in cultured rat hippocampal neurons. It was found that the application of modest voltages at frequencies on the order of 10^5 Hz could cause developing axons to be stopped adjacent to the electrodes while axons away from the electric fields exhibit uninhibited growth. By switching electrodes on or off, axon passage across the electrodes could be reversibly inhibit or permit.

Figure 5A:
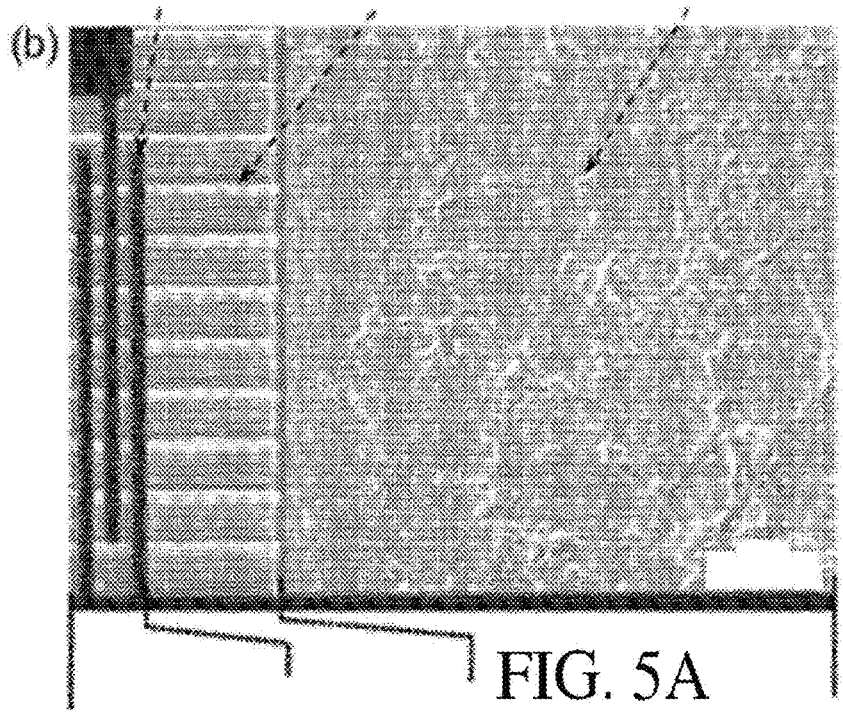
FIGS. 5A-B illustrate devices for altering neurite growth in accordance with certain embodiments of the invention.
Figure 5B:
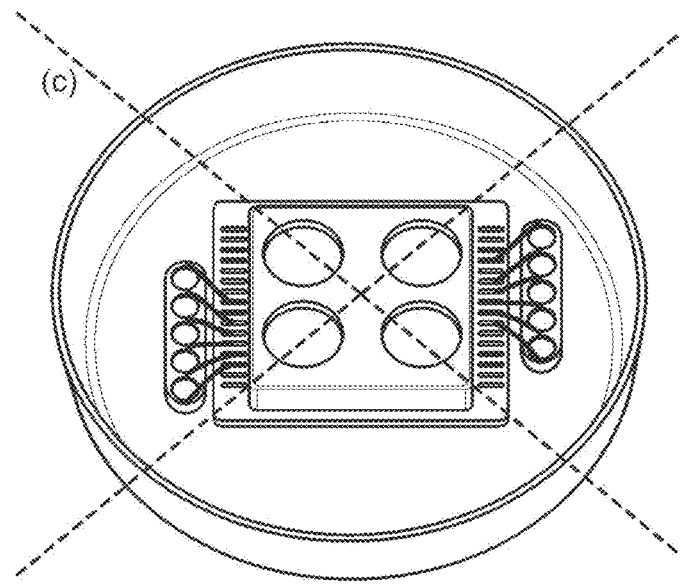

To determine if AC electrokinetic forces could affect axonal growth, a microfluidic platform, as shown in FIGS. 1A and 5A-B, based on an axon isolation device, which is composed of two wide microfluidic chambers, in one of which neurons are cultured, was developed. The two chambers were connected by an array of parallel microchannels that constrain axonal outgrowth to one dimension. To allow the application of alternating current electric fields within the microchannels, the microfluidic platform was bonded to glass that had been pre-patterned with interdigitated gold electrodes (15 μm width spaced by 15 μm). By bonding the glass and PDMS such that the electrodes run perpendicular to the microchannels, AC electrokinetic forces can be applied that act parallel to the channel to block the one-dimensional axon growth.

Upon adding neurons to the culture chamber, extensive neurite outgrowth occurred by 4 days in vitro (DIV), with many neurites entering the microchannels (FIG. 5A). FIG. 1A shows an illustrated cross section of the device of the Microfluidic neuronal electrokinetic platform. FIG. 5A is an image of neurons growing in the device at four days in vitro. The scale bar in the figure is 50 microns. FIG. 5B is a photograph showing the 4-well fluidic interface and the electric interface. The scale bar is 1 cm.

Next an AC signals was applied to the electrodes and axon growth was monitored. In microchannels that were not crossed with electrodes, axons grew through the length of the microchannel (FIGS. 1C-D). However, axons in microchannels with electrodes stopped growing at the electrodes (FIG. 1C) when the field was applied. Once the field was turned off, axons resumed their growth through the microchannel (FIG. 1D), indicating that they remained viable. To quantify the effect that AC fields have on axonal growth, both the frequency and the voltage amplitude of the AC signal were varied after application for 7 days in vitro. The frequencies were limited to the range of 100 kHz-1 MHz and voltages to a range of 0-3 $V_{p-p}$ to avoid significant temperature rise ($\Delta T \sim \sigma V^2/k$, where σ is the medium electrical conductivity and k its thermal conductivity, here $\Delta T \sim 7°$ C. in cell culture media at maximum voltage) or electrolysis in the high-conductivity hippocampal culture medium (measured at $\sigma_m = 0.98 \pm 0.08$ S/m). Both the frequency and voltage of the AC signal had a significant effect on the axon length, with lower frequencies causing greater inhibition of axon outgrowth (FIG. 6) at a given voltage.

FIG. 1C is a fluorescent false-colored image of axonal growth in microchannels with perpendicular interdigitated electrodes at 4 days in vitro. Neurons were infected with tubulin-GFP baculovirus for live-cell visualization purposes. Closed arrowheads denote an axon in a control channel without electrodes that grows through the microchannel. Open arrowheads denote an axon in a microchannel with electrodes that is stopped at the electrode edge. The frequency was 100 kHz and the voltage was 2 V.

Figure 6:
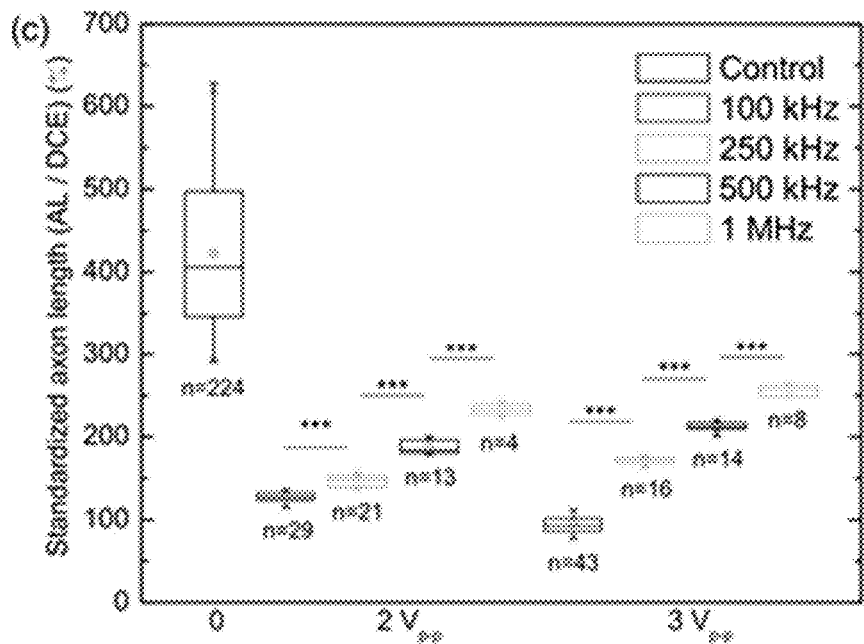
FIG. 6 illustrates neurite growth in accordance with various embodiments of the invention.

The scale bar is 150 microns. FIG. 1D is a fluorescent false-colored image of axonal growth at 6 days in vitro after application of the electric field for 4 day in vitro. Closed arrowhead denotes the end of an axon. FIG. 6 is a graph of standardized axon length versus voltage after 7 days culture in the chip with voltage ON. (***: p<0.001). In the figure, n refers to the number of axons measured over two independent replicate experiments.

Figure 7:
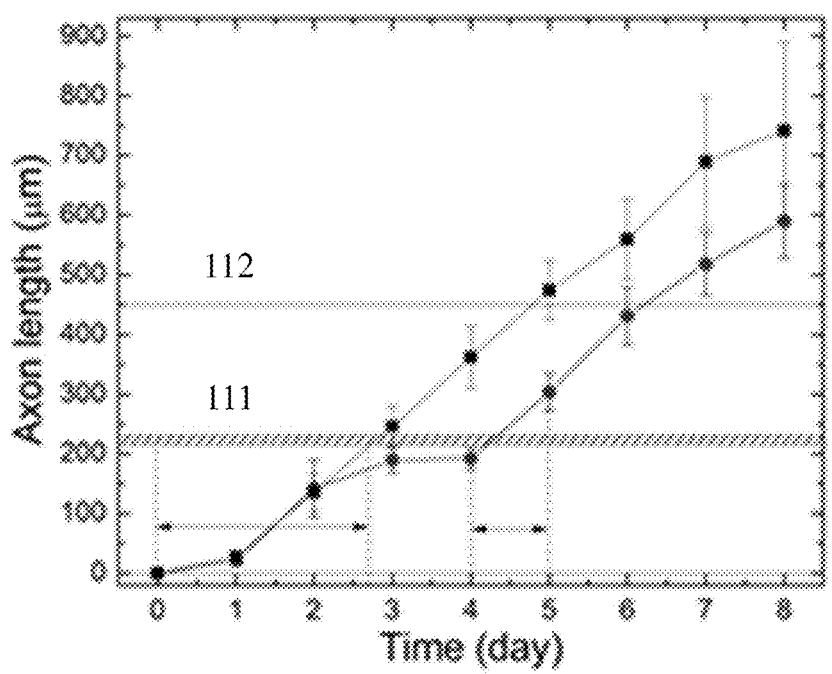
FIG. 7 illustrate neurite growth in accordance with one embodiments of the invention.

FIG. 7 shows the length of axons over time in the platform for a control experiment (no field application) and for axons blocked by the AC electrokinetic effect. The distances to the first electrode and to the end of the channel are highlighted. Axons coming from the main body compartment reach the first electrode in ca. 3 days whereas axon elongation after releasing axons from AC blocking takes less than 1 day. The results strongly suggest that observed axon elongation between 4 days in vitro and 6 days in vitro results from blocked axon elongation and not new dendrites growing from the cell body compartment.

Figure 8A:
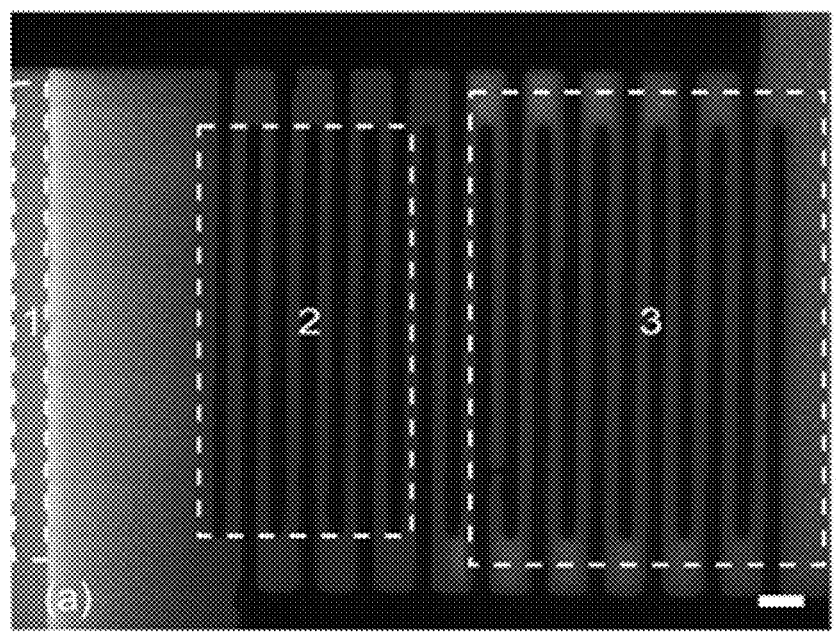
FIGS. 8A-B illustrate features of device components in accordance with one embodiment of the invention.
Figure 8B:
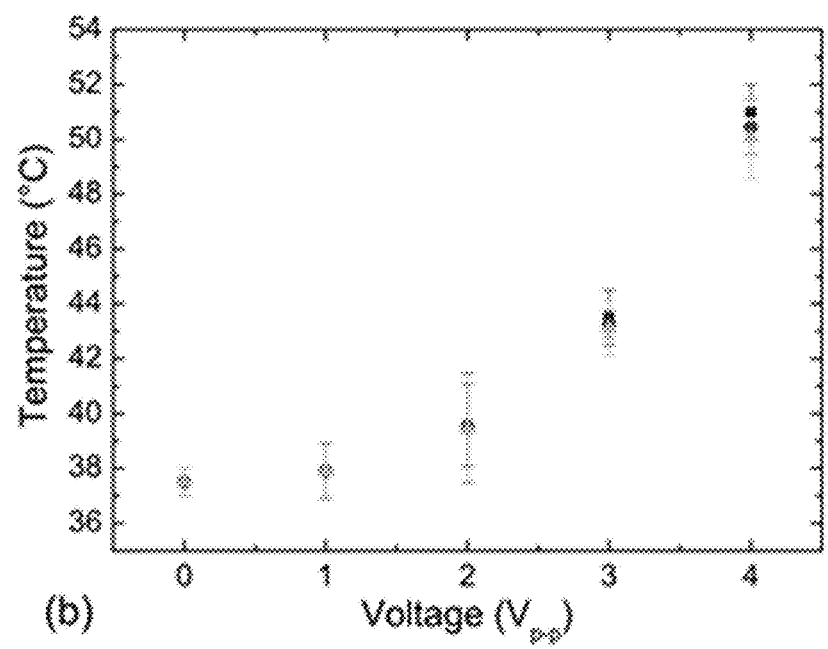

FIG. 8 shows the measurement of temperature around the electrodes using Rhodamine B, a fluorophore with temperature-dependent fluorescence intensity (at a concentration of 1 mM in culture medium). FIG. 8A is a false-color image of Rhodamine B around the electrodes. The color represents the spatial distribution of the temperature. Rhodamine B fluorescence intensity decreases with increasing temperature, so the dark-colored areas indicate a higher temperature compared to the orange ones. Hence, the electrode-free microfluidic chamber (area 1) is orange (cooler) whereas the microchannel with electrodes (area 3) is red (warmer). The highest temperature area can be seen where the electrodes are bonded to the PDMS (area 2), and more specifically in the grooves and closed to the electrodes (left-hand side of area 2), where the axons are found not be growing anymore at voltages >3.5 Vp-p. Scale bar indicates 50 microns. FIG. 8B is a plot of the extracted temperatures. Each point consisted in applying the voltage for 5 seconds at a given frequency and taking an image (500 ms exposure time, fixed camera gain) with TRITC filter set of three different interdigitated electrodes, each on a temperature-controlled stage set to 37.5° C. For each image, fluorescent intensities from an area of 240×480 microns (area 2) were averaged spatially and across the three electrodes, and compared to a calibration curve. Calibration was performed using a hotplate to determine the temperature dependence of the Rhodamine B fluorescence intensity, obtaining a measured slope consistent with ones observed in literature (−1.3%/° C.). The measured temperature is independent of frequency and increases supralinearly with voltage, which would be expected for Joule heating.

EXAMPLE 2

This example describes modeling of the electrokinetic effect on the growth cone of the neurite. Without being bound by theory, the models suggest that dielectrophoresis is the causative AC electrokinetic effect that results in a physical guidance cue.

The mechanism of the electrokinetic effect could be discerned by determining which types of AC electrokinetic phenomena were consistent with the results in FIG. 1D. The different AC electrokinetic forces acting on the growth cone were modelled.

The growth cone was ellipsoidally shaped near a glass surface, connected to an axon that is 10 times smaller to its width, and a large fraction of it is comprised of actin filaments that coordinate its growth. The growth cone was modelled as a core-shell oblate object composed of three shells (FIG. 9): (1)—an actin layer (width a=2 μm, height b=200 nm), (2)—a cytoplasm layer (homogenous height $d_{cyt}$=300 nm) and (3)—the cell membrane (homogenous height $d_{mem}$=10 nm). The characteristic lengths of this objects were $a_1$=b+$d_{mem}$ and $a_2$=$a_3$=a+$d_{cyto}$+$d_{mem}$. This polarizable object was exposed to 3 forces: AC electroosmosis (ACEO) and electrothermal effect (ETE), that are electro-hydrodynamical forces acting on pure fluid (i.e., in the absence of particles) and dielectrophoresis (DEP) that is acts on the growth cone itself.

ACEO refers to the flow generated near the electrodes surfaces when AC signals are applied. It is a frequency-dependent flow that is maximal at the frequency at which the product of the tangential electric field and the induced double-layer charge reaches a maximum. Following the traditional method to model co-planar electrodes ACEO, the time-average ACEO velocity ($\langle u_{ACEO} \rangle$) on the electrode is given by $$\langle u_{ACEO} \rangle = \frac{1}{8} \frac{\epsilon_m V_0^2}{\sigma_m r} \frac{\Omega_{ACEO}^2}{(1+\Omega_{ACEO}^2)^2} \quad (1)$$

with $$\Omega_{ACEO} = \frac{\pi}{2} \frac{r}{\lambda_d} \frac{\epsilon_m}{\sigma_m} \omega$$

where $\Omega_{ACEO}$ is the non-dimensional frequency, $\epsilon_m$ is the permittivity of the media, $\sigma_m$ is the media conductivity, $V_0$ is the potential applied on the electrodes, r is the polar coordinate where the force is evaluated (here r is set to the half-length of the growth cone), $\lambda_d$ the Debye length of the electrolyte/electrode interface and ω the frequency of the AC signal.

Second, an electrothermal flow can be induced when an electric field is applied in the media and causes Joule heating. For non-uniform fields (as is the case here), there will be spatial variation in heat generation, which leads to spatial gradients in the local permittivity and conductivity, which are acted upon by the electric field to induce a bulk fluid flow. The time-averaged velocity $\langle u_{ETE} \rangle$ is $$\langle u_{ETE} \rangle = \frac{\ln\left(2\frac{a_1}{a_2}\right) - 1}{2\pi^4 k \eta_m a_1} \frac{\epsilon_m \sigma_m V_0^4}{r^3} \left(1 - \frac{2\theta}{\pi}\right) \Pi(\omega) \quad (2)$$

with $$\Pi(\omega) = \frac{\alpha - \beta}{1 + (\omega \tau_m)^2} - \frac{\alpha}{2}$$

where $\eta_m$ is the media viscosity, k is the media thermal conductivity, (r, θ) is the polar coordinate where the force is evaluated, $\tau_m$ the media relaxation time given as $\tau_m$=$\epsilon_m/\sigma_m$, α=−0.4% K$^{-1}$ and β=2% K$^{-1}$. The factor Π does not vary over the range of frequencies we apply for our medium conductivity and has a constant value of −0.022.

The ACED and ETE velocities sum to give a global net EHD velocity $\langle u_{EHD} \rangle$ that is converted to a force $\langle F_{EHD} \rangle$ acting on the growth cone via the ellipsoidal friction factor at steady state regime.

$$\langle F_{EHD} \rangle = f \cdot \langle u_{EHD} \rangle = f \cdot (\langle u_{ACEO} \rangle + \langle u_{EYE} \rangle) \quad (3)$$

where $$f = \frac{4\pi \eta_m a_1}{\ln\left(2\frac{a_1}{a_2}\right) - 1}$$

The third force is the DEP force. Using the same approach as Castellarnau, for an oblate spheroid in a co-planar electrode configuration, we extrapolate the n-th order of the DEP force acting on the growth cone is given as $$\langle F_{DEP} \rangle = \frac{32}{3} a_1 a_2 a_3 \epsilon_m \frac{V_0^2}{d^3} e^{-\frac{\pi r}{d}} Re[CMF(\omega)] \quad (4)$$

With $$Re[CMF(\omega)] = \sum_{i=1}^{3} \frac{1}{3} \frac{\epsilon_p^* - \epsilon_m^*}{n\epsilon_m^* + A_i(n+1)(\epsilon_p^* - \epsilon_m^*)}$$

where d is the distance between the electrodes (in our setup d=15 μm), $A_i$ is a component of the depolarization factor along any one of the three axes of the ellipsoid, $\epsilon_p^*$ and $\epsilon_m^*$ are the complex permittivities of the inner and of the outer compartment of the i layer, respectively and n the order of the multipole. The Clausius-Mossotti factor (CMF) captures the frequency dependence of the force and is represented for a wide range of frequency and for several media conductivity on FIG. 10. The dielectric properties of each layer were extracted from literature for actin, neuron cytoplasm and membrane. Since the field strength varies greatly over the growth cone dimensions, higher order moments of the Clausius-Mossotti factor (FIG. 10B) as introduced by Jones and Washizu (1994) up to n=4 were considered. We find that the contribution to the overall DEP force of these higher-order multipoles is much smaller (~10$^5$ times smaller) than that of the classical dipole contribution. These higher-order forces, as our results and literature have shown, repel the object and so add constructively to the DEP force, and thus are consistent with our findings that the DEP force is larger than the EHD forces at our operating conditions. Moreover, this model does not take into account deviations in the DEP force due to proximity of the growth cone with the glass surface. However, Lynch et al. measured the DEP force of red blood cells attached to a glass surface and found that the forces were in good agreement with the classical core-shell isolated-particle model. Therefore it can be assumed the same behavior for growth cones in our system.

Figure 10B:
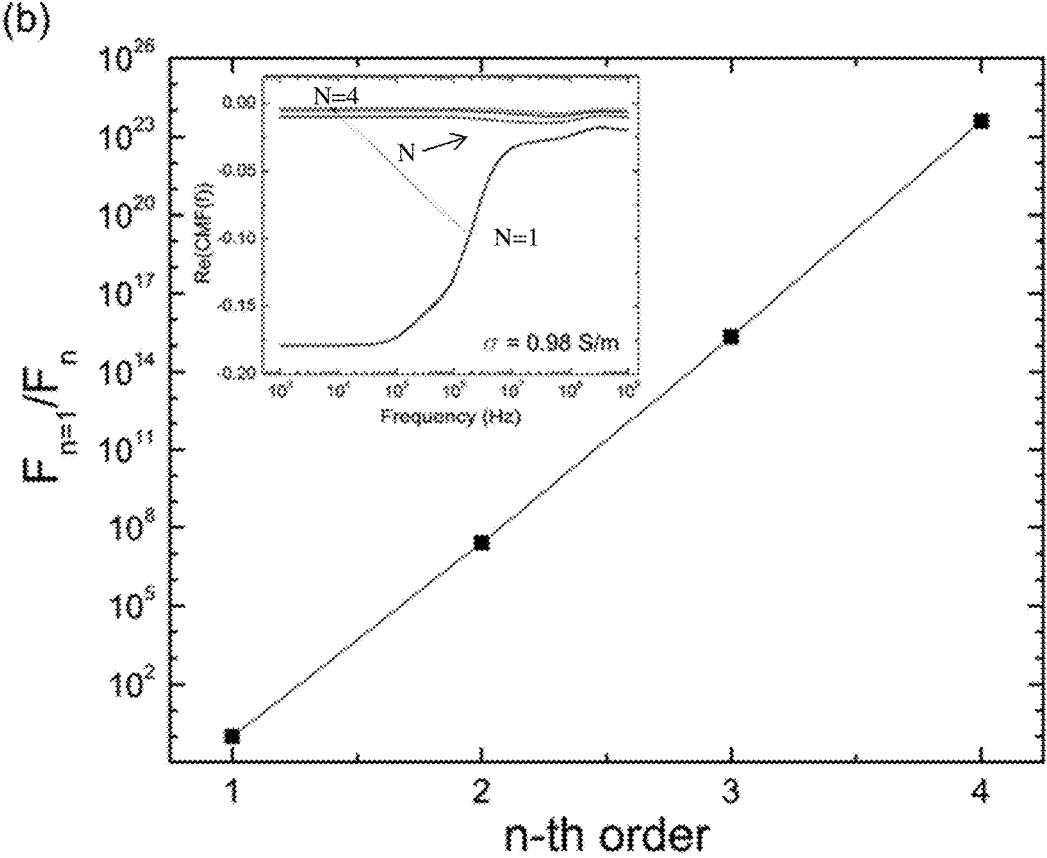
Figure 11A:
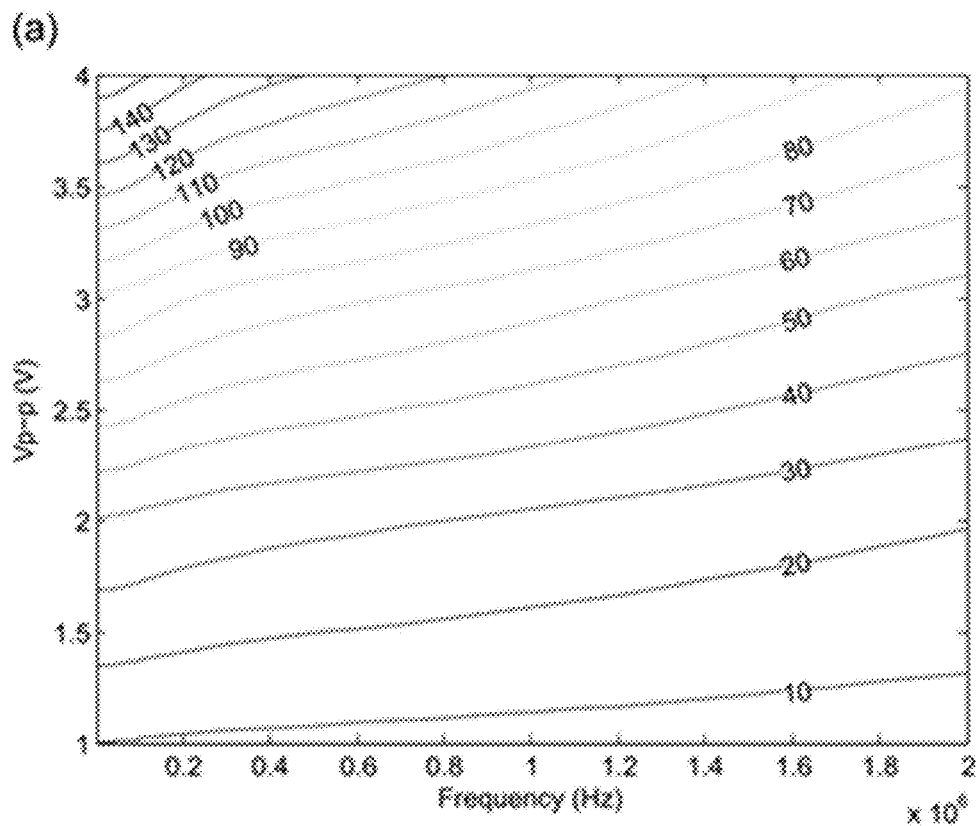
FIGS. 11A-B illustrate features of a model in accordance with one embodiment of the invention.
Figure 11B:
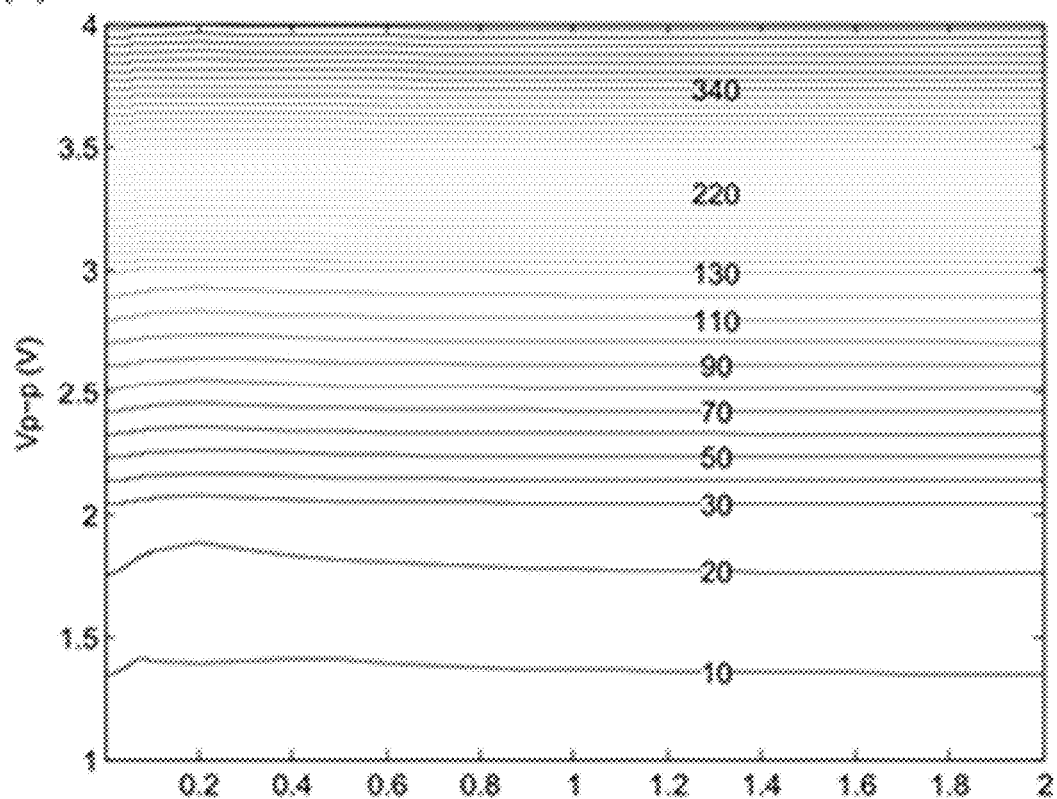

Since all forces are frequency and voltage dependent, the relative magnitude of induced EHD and DEP forces was plotted across a range of frequencies and voltage amplitudes (FIG. 10B) and the absolute values of those forces are plotted on FIG. 11. DEP forces and EDH flow both act cooperatively to repulse the growth cone from the electrodes. The resulting model provides robust information about trends and order of magnitudes of the forces exerted on the growth cone. The EHD Force has an almost-constant response across the 200 kHz-1 MHz frequency range, whereas the DEP force magnitude is strongly frequency dependent (FIG. 3SB). We find that the DEP force is larger than EHD forces at low voltages (<2.70 $V_{p-p}$) where heating is minimal. In terms of frequency, EHD becomes more significant at frequencies above ~250 kHz because the magnitude of the CMF of the growth cone (and thus the DEP force) decreases at f>100 kHz.

Examining the axon blockage data (FIG. 1D), it was found that lower frequencies (f<250 kHz) resulted in the smallest axon lengths, and is where the DEP/EHD ratio is largest (FIG. 3b). Similarly, the model shows a decrease in the magnitude of the DEP force at higher frequencies (f>250 kHz), while experimentally increasing axon lengths was observed—and thus smaller electrokinetic effect—when raising frequencies. Moreover, the model shows that the DEP/EHD ratio decreases with increasing voltage at a given frequency, while the experiments show increasing axon length with increasing voltage at all frequencies except 100 kHz. Interestingly, this lowest frequency may correspond to the peak in the DEP/EHD versus frequency plot (FIG. 9B), where the DEP force is stronger than EHD over a large voltage range. Thus, the trends in the quantitative axonal length data (FIG. 1D) are most consistent with a mechanism whereby the developing axon is acted upon by a DEP force. With the model and the values of the parameters, it was found that the maximum DEP force that is exerted on the growth is ~66 pN (FIG. 11), which is in the same order of magnitude of the pulling force exerted by the growth cone of spinal commissural neuron axons in vitro, and the force exerted by Netrin-1 to cause growth cone attraction.

It should be understand that this AC electrokinetic model is a non-limiting hypothesis, but provides insight into the potential process that drives inhibition of axonal growth from high-strength AC electric fields. Alternative mechanisms could act intracellularly, such as through field-induced actin polarization, and are an intriguing avenue for future research.

Figure 9A:
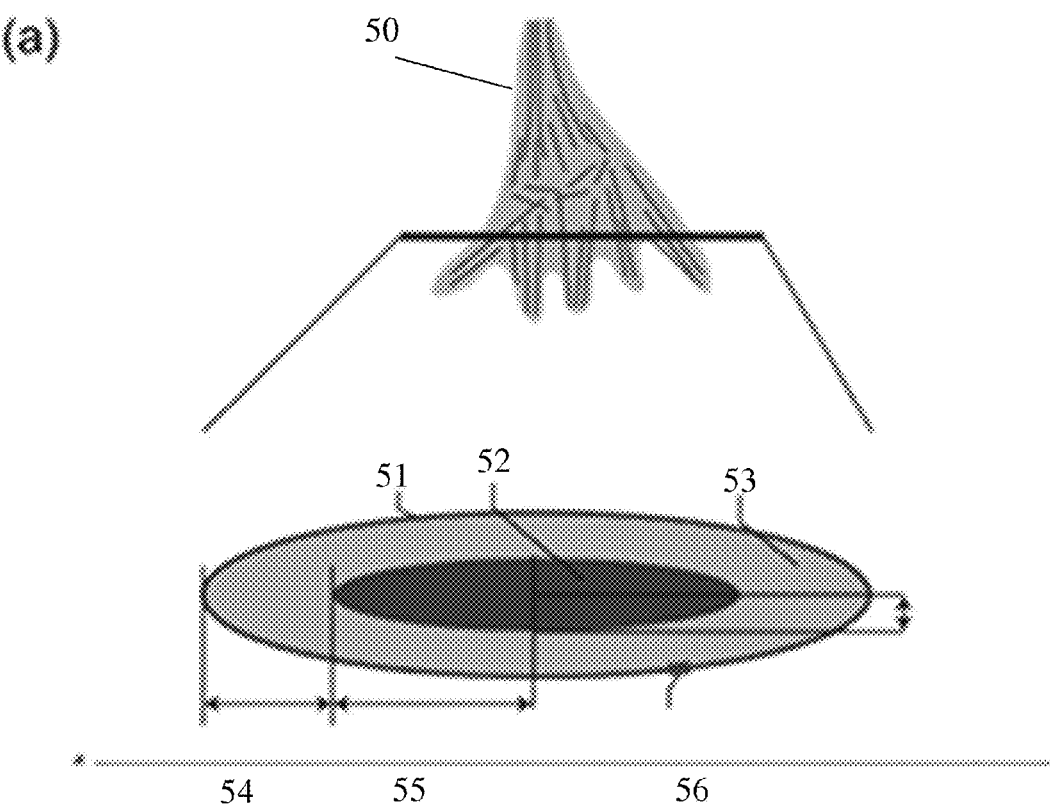
FIGS. 9A-B illustrate features of a model in accordance with one embodiment of the invention.
Figure 9B:
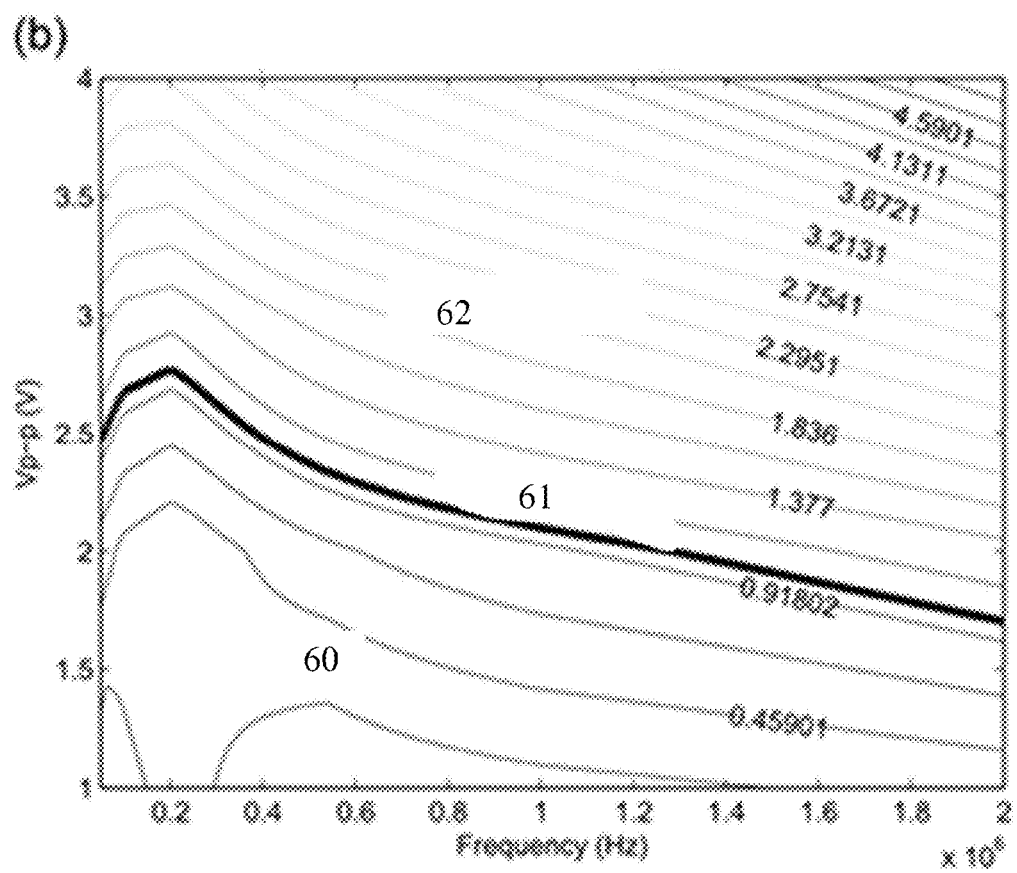

FIG. 9A is a schematic of the growth cone model used in our analysis. FIG. 9B is a modelled ratio between DEP and EHD forces on the growth cone.

Figure 10A:
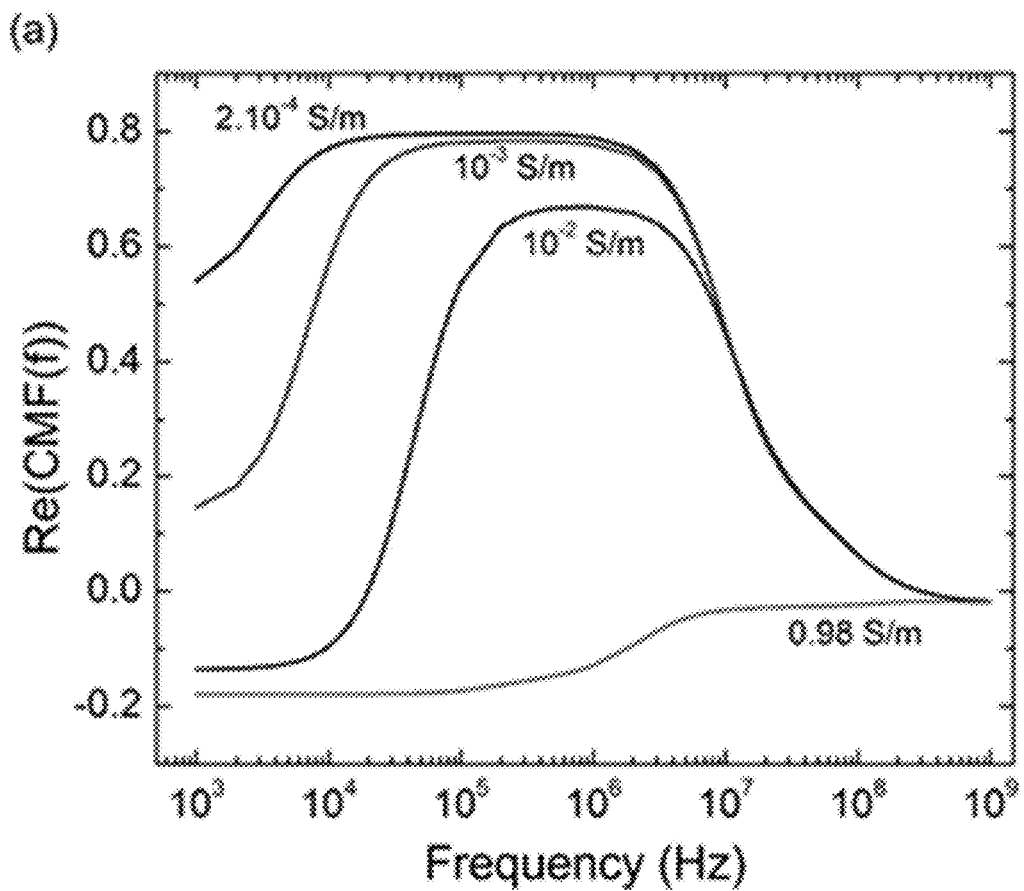
FIG. 10A-B illustrate features of a model in accordance with one embodiment of the invention.

FIG. 10 is show simulated Clausius-Mossotti factor of the growth cone model. FIG. 10A shows first-order (dipole) model for several media conductivities and FIG. 10B shows the ratio between first-order DEP force and the n-th-order force for increasing numbers of multipoles at neuronal media conductivity. The inset plot represents a detailed view of the n-th order multipole of the CMF of the growth cone. The higher orders of the DEP forces are several orders-of-magnitude smaller than the first-order force.

FIG. 11 shows Simulated values of the dielectrophoretic (FDEP) and electrohydrodynamic (FEHD) forces across the range of frequencies and voltages used in the study. The EHD force has an almost-constant response across frequency, whereas the DEP force magnitude is strongly frequency dependent in the 200 kHz-1 MHz range, which is consistent with the trends observed experimentally.

EXAMPLE 3

This example describes use of the dynamic control over axon elongation of the present invention to create an axon-diode via an axon-lock system that consists of a pair of electrode 'gates' that either permit or prevent axons from passing through.

Figure 12:
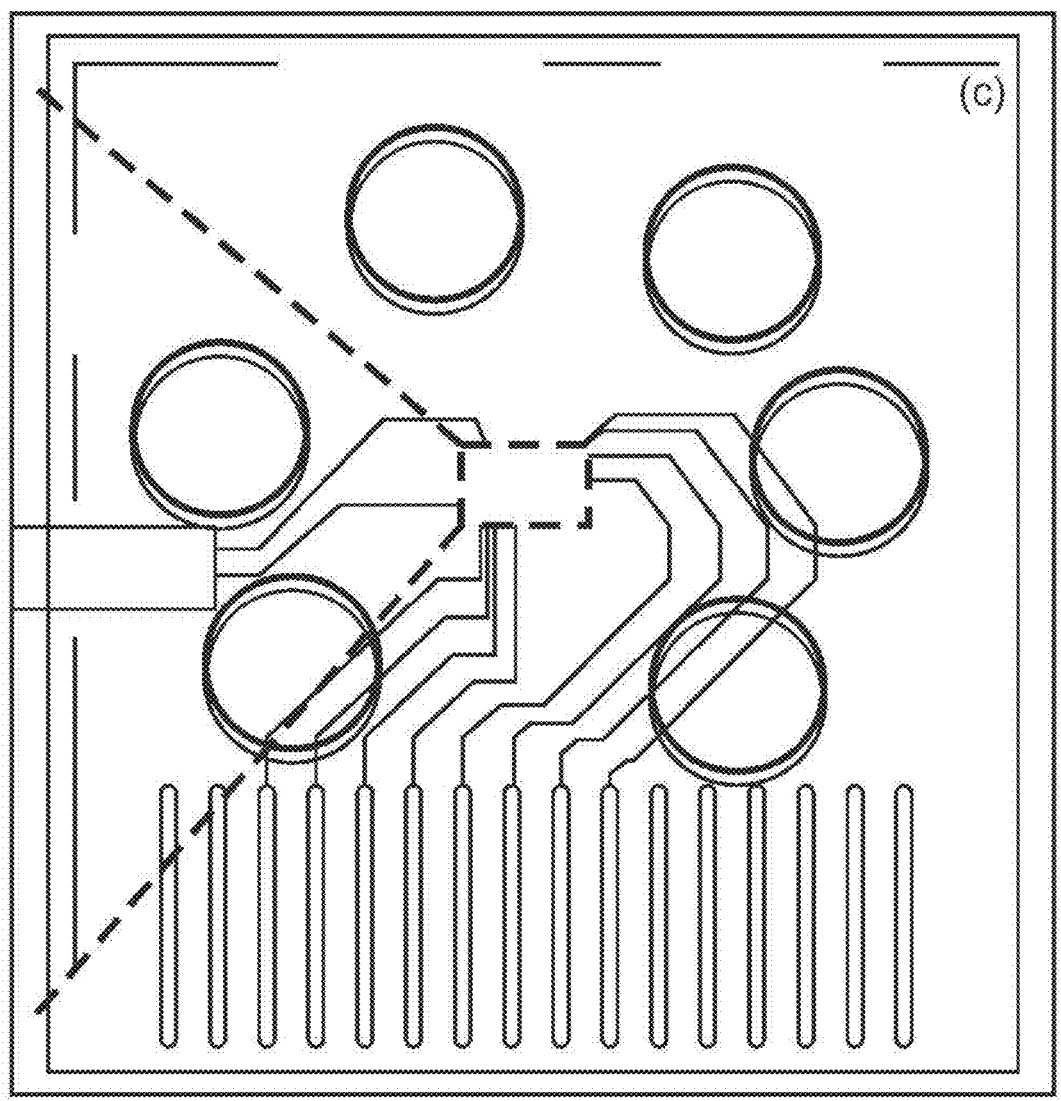
FIG. 12 illustrates a device for forming neural connections in accordance with various embodiments of the invention.

The dynamic nature of electrokinetic axon blocking was exploited to form unidirectional growth of axons, and thus form an axon diode. The axon diode used two sets of electrodes that acted like gates in a lock to allow axons from only one side to grow across (FIG. 2A). The device was a three-microchamber chip, arranged as an equilateral triangle, with each microchamber having its own inlet and outlet reservoirs (FIG. 2B) that interface with 6 wells for solution transfer (FIG. 12). Each microchamber was connected to the other one through microchannels in which only the axons can grow (height ~3 microns). Each microchannel has two axon 'gates' formed by placing two sets of electrodes (ground-AC-ground), at each end of the microchannel (FIG. 2B). To create an axon diode, the gates that connect each pair of microchambers were opened and closed in a dynamic manner. When its AC voltage was turned off, the gate was open and the axons were free to grow beyond the electrodes. When the AC signal was turned on, the gate was closed and the axons could not proceed across the gate. The parameters of the AC signal applied to close a gate were set to f=100 kHz and V=3 V p-p, as these were found to be effective at blocking neurite outgrowth (FIG. 1D).

Figure 13:
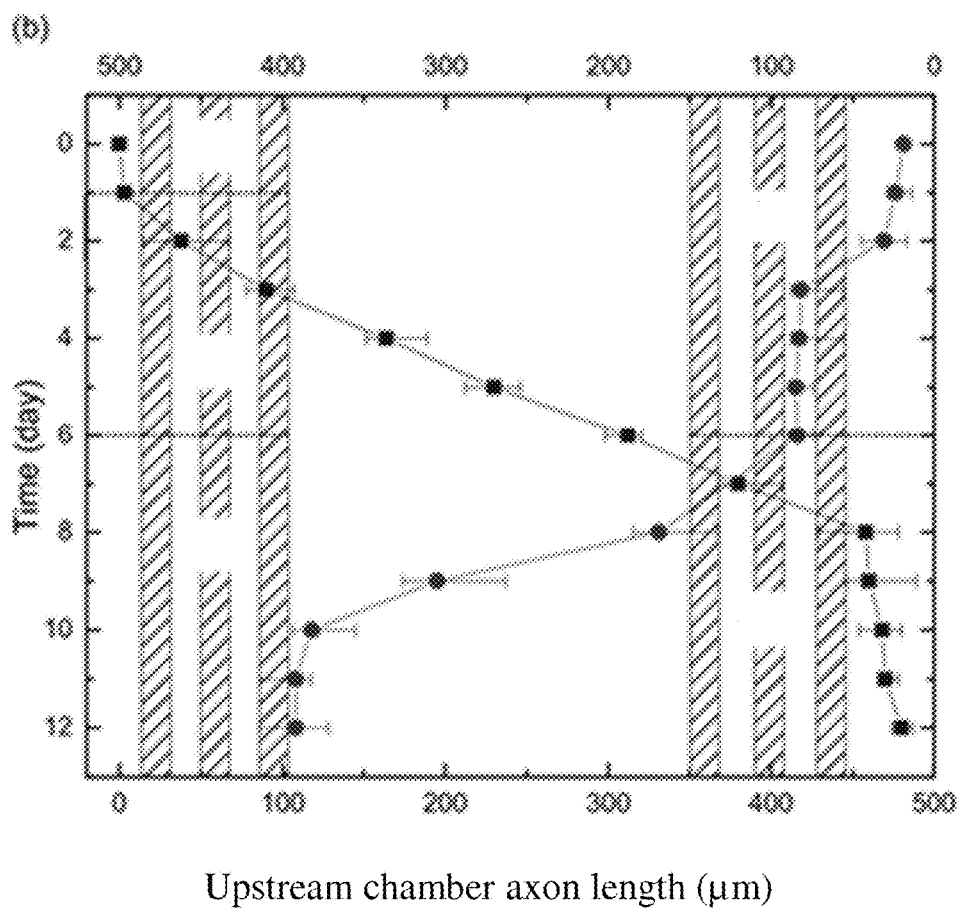
FIG. 13 illustrates the growth of neurites in accordance with certain embodiments of the invention.

We demonstrated the diode functionality by first plating neurons in each of the three microchambers with the gates initially closed (the AC voltage is applied) (FIG. 2Ci). After 24 hours, one of the two gates in a microchannel was opened (the AC voltage was switched off), allowing axons from one microchamber, termed the 'upstream' microchamber, to extend axons into the microchannel (FIGS. 2Ci-ii), while axons in the opposite "downstream" microchamber, remain blocked by the closed gate. The directionality of the neuronal connection was defined by which gate is opened first, with axons passing only from upstream to downstream microchambers. Once axons have extended beyond the open gate, the state of the two gates was reversed: the initially open gate was closed and the previously closed gate was opened (FIG. 2C-11$i$). In doing so, upstream axons in the microchannel would extend beyond the second gate and establish connections with the downstream neuron population. Since the first gate was now closed, axons from the downstream microchamber were unable to migrate to the upstream microchamber and would be trapped in the microchannels or remain in the downstream microchamber. Finally, both gates were closed to prevent any further axons from migrating through the microchannel (FIG. 2C iv). The lengths of axons (n=12) from upstream to downstream microchambers were measured during this process (FIG. 13). It can be seen that the axon did not pass across the activated electrodes as long as the field was turned on. Moreover, the growth cone did not turn back from the activated electrodes (standard deviation of the growth cone medium position diminished with time). When the gate opened, the axon growth process continued at a rate of 42±7 microns/day which is significantly slower (relative error of 41%) compared with the observed growth rate in the middle of the channel (72±10 microns/day). This could be explained by the time for the growth cone to explore the surface that was previously inaccessible because of the electric field. Finally, the downstream axon stayed in front of the upstream gate without passing through once that gate is turned on. This specific spatio-temporal application of the electrokinetic axon blockage is called the "axon-lock system".

FIG. 2C shows a side-view schematic of axon diode and FIGS. 2B and 12 are Images of axon diode chip showing three microchambers and electrodes.

FIG. 2C shows a schematic (left) and phase images (right) of the axon-lock system where growth cones are pinpointed by an oriented white arrow. The middle of the channel is highlighted by a white spot. The Roman numerals describe the following: (i) both gates closed, such that no axons enter microchannel; (ii) left gate opened, and a single axon enters from the left; (iii) left gate closed and right gate opened; (iv) both gates are closed after the first axon passes completely beyond the gate. FIG. 13 is a graph of the measured lengths of axons migrating from the upstream microchamber (blue) and the downstream microchamber (red) along with the activation timing of the left and right gates.

EXAMPLE 4

This example describes the development of a neural circuit consisting of three populations of neurons, separated by three axon-locks to demonstrate the assembly of a functional, engineered neural network. Action potential recordings demonstrated that the AC electrokinetic effect did not harm axons, and $Ca^{2+}$ imaging demonstrated the unidirectional nature of the synaptic connections.

Using the axon-lock system, construction of functional axon diodes was demonstrated. Axon diodes have been developed and used in vitro to mimic the directionality of neuronal path guidance in vivo. Directionality is critical for regenerating axons to create proper connections after peripheral nerve injury and during development. Few in vitro systems are capable of creating directional connections. AC electrokinetic effects have the advantage of reconfigurability because the electric field can be turned on and off at will. Thus, the capacity to dynamically lock or release the growth of a developing axon has exciting potential for the creation of neuronal networks. In particular, selective growth of axons in neural guidance conduits could improve routing of axons to their targets and prevent mis-sprouting of axons and inappropriate innervation.

To generate neural networks using multiple axon diodes, electrode gates were dynamically opened and closed to direct axons such that chamber 'A' was connected in one direction with chamber 'I', and chamber 'B' was connected in one direction with chamber 'C', whereas chamber 'C' was not connected in either direction to chamber 'A'(FIG. 6A).

We first examined the functionality of axons that passed through an active gate to verify that the AC electric field does not damage the axons' ability to generate and propagate action potentials (APs). To make action potential measurements, we re-purposed the gate electrodes as stimulating and recording electrodes to monitor AP propagation in axons that passed through the diode. The first set of electrodes was used as stimulating electrodes and the second set as recording electrodes.

Figure 14A:
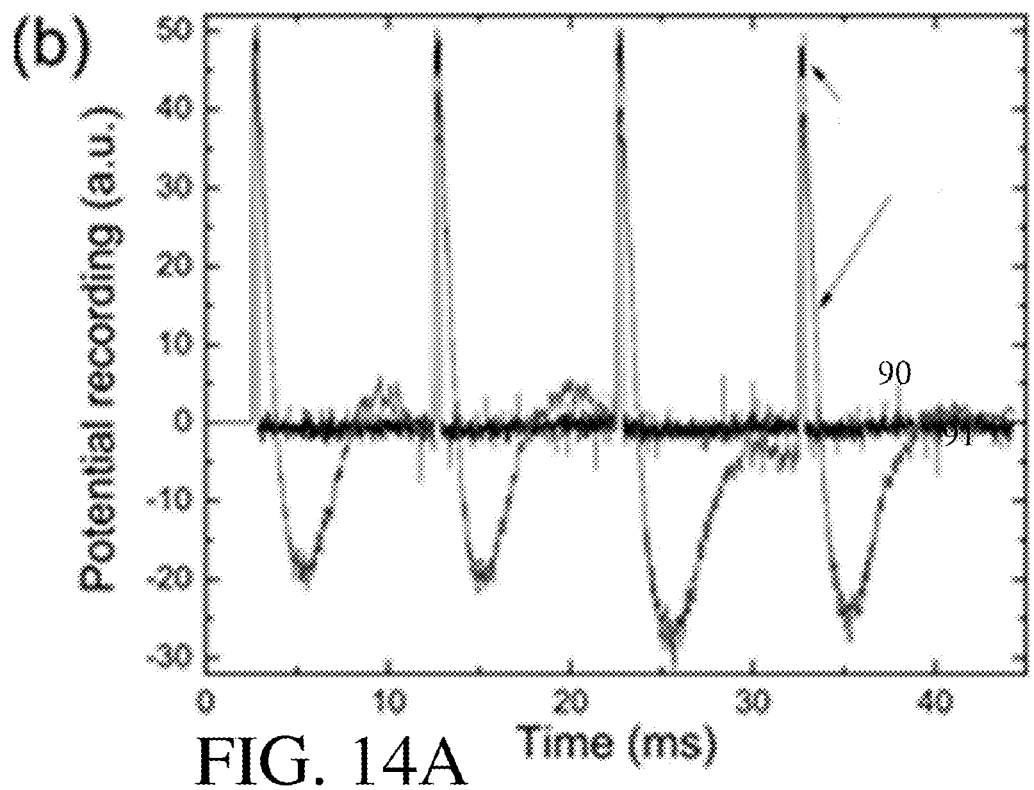
FIGS. 14A-B illustrate action potential recordings and fluorescent images in accordance with one embodiment of the invention.

FIG. 14A shows action potential readings from a set of axons that had passed through one of the axon-locks. When each stimulating pulse was applied, an AP was recorded further along an axon that passed through the entire diode, establishing that the axon-lock system does not interfere with AP generation or propagation.

Figure 14B:
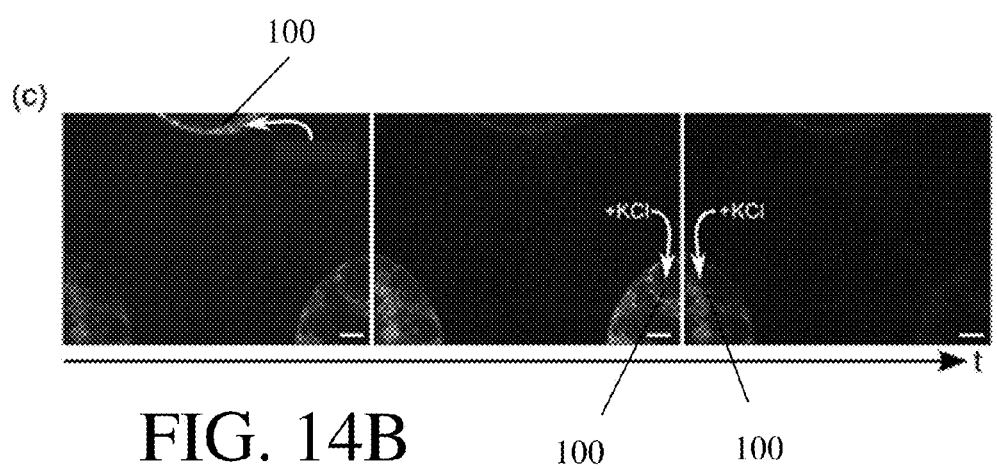

Whether the synapses of the directional network were active was then determined. Oregon Green BAPTA 1 was used as a stain to visualize $Ca^{++}$ fluxes elicited when action potentials were induced with KCl addition. KCl stimulation was confined to a single microchamber by selectively pressurizing the other outer reservoirs (FIG. 15). When KCl was added to chamber 'A', depolarization was observed in all three chambers (FIG. 14B, left), whereas addition of KCl to chamber 'B' only elicited $Ca^{++}$ oscillations in chambers 'B' and 'C' (FIG. 14B, middle), and addition of KCl to chamber 'C' only induced oscillations in chamber 'C' (FIG. 14B, right). These results demonstrate that chamber 'A' was connected to chamber 'B' and to chamber 'C' (FIG. 14B, left), and further that functional synapses were able to transfer signals from neurons originating in chamber 'A' to those in chamber 'C', via chamber B. Additionally, the observation that stimulating chamber 'B' induces $Ca^{++}$ oscillations in chamber 'C' (FIG. 14B, middle) but stimulating chamber 'C' does not induce $Ca^{++}$ oscillations in chamber 'B' (FIG. 14B, right) demonstrates that the two chambers are directionally connected by the axon diode. Overall, these results demonstrate the ability to create directionally connected networks of hippocampal neurons in our axon-lock system.

Figure 15A:
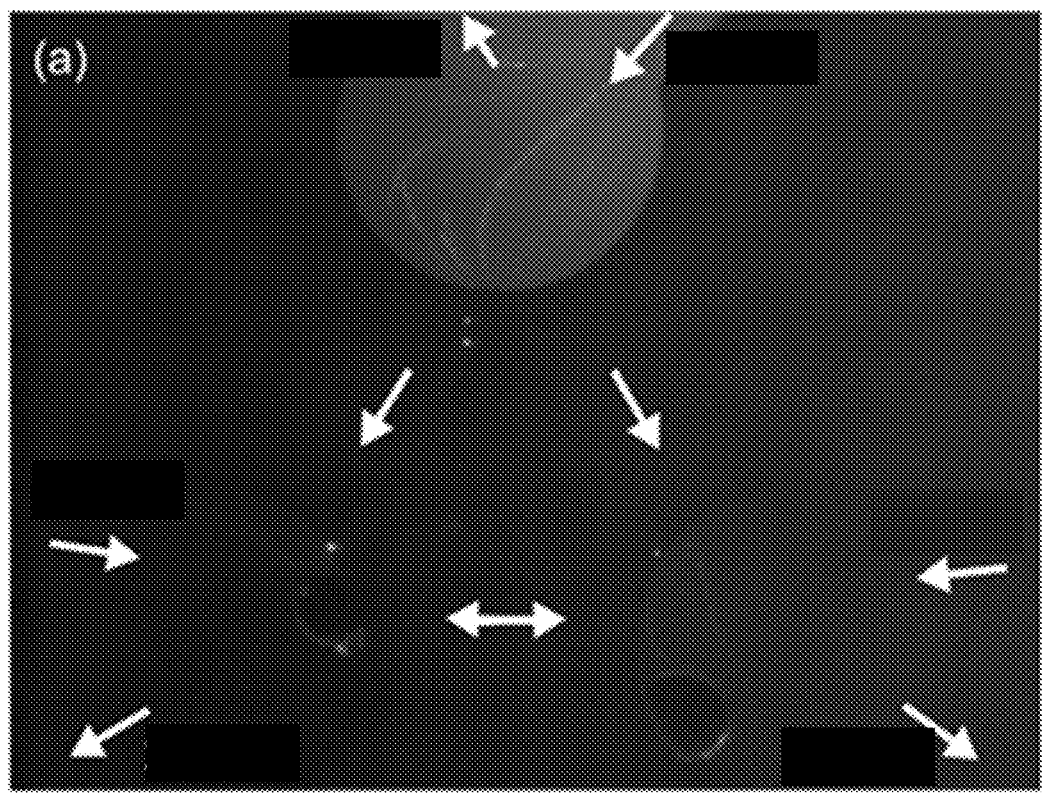
FIGS. 15A-B illustrate features of a device component in accordance with certain embodiments of the invention.
Figure 15B:
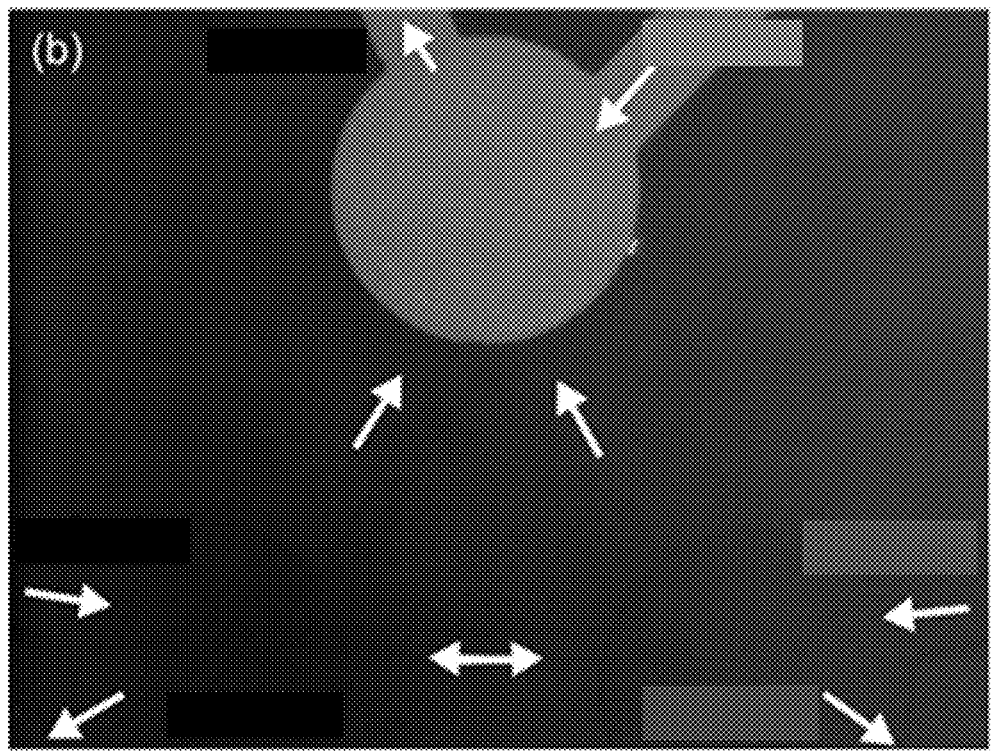

FIG. 3 is a fluorescent false-colored image of a 12 days in vitro neuronal network configured by the axon-lock system. The plain arrows represent the direction of the diode. FIG. 14A shows the action potential recording, showing the stimulation signal (black) and the downstream recorded signals (colored). FIG. 14A is a false-colored fluorescent images of Oregon Green BAPTA 1-stained neurons when stimulating each sub-population of neurons in turn (denoted by +KCl). Scale bar is 50 microns FIG. 15 shows compartmentalization of flow by using differential hydrostatic pressure. The pressures are induced by the volume of liquid placed in the inlet and outlet reservoirs connected to each microchamber. Therefore it is possible, by placing the right liquid volume, to direct flow from one microchamber to the other and hence to contain the local application of a chemical to one population of neuron only. FIGS. 15A-B are fluorescent images of the three microchambers when the flow is not confined and when the flow is confined, respectively. The arrows indicate the direction of the flux and the volumes the amount of liquid inserted in the in/outlets. The flow was visualized by injecting 10 micromolar fluorescein and 1 micromolar fluorescent polystyrene beads in one reservoir.

EXAMPLE 5

This example describes materials and methods used in experimentation.
Microfabrication of Electrokinetic Devices and Preparation for Neuron Plating.

The microfluidic chip was fabricated on a 150-mm glass wafer. Following a standard photolithography step, a 10/100 nm Ti/Au bi-layer was e-beam deposited and a lift-off in acetone revealed the electrodes. The wafer was then die-sawed to obtain individual chips. The microchannels comprise two types of components: high channels (100 µm) for cell injection and shallow channels (3 µm in height) for axon growth. They were molded from a SU-8 (Microchem) master that was fabricated with a two-step lithography process with thin (SU-8 2005) thick (SU8-2050) resists. Microchannels were then molded with degassed and cured PDMS (9:1 mass ratio with curing agent, Sylgard 184, Dow Corning). Plastic masters were then used as future molds for the final PDMS replicates. The microgrooves were manually aligned under a binocular after air plasma exposure (2 minutes) and immersion in methanol (5 minutes). The assembled chip was cured at 100° C. for 30 minutes.

Two different microfluidic chips were constructed in this way. The first (FIG. 1) was a two-compartment chip made of rectangular microchannels (length: 4000 µm; width: 500 µm; height: 100 µm) separated by arrays of microgrooves (length: 450 µm; width: 5 µm; height: 3 µm). The second chip (FIG. 4) was a three-compartment chip made of 5-mm punched inlet and outlet reservoirs connected to three microchambers (diameter: 500 µm, height: 100 µm) placed in an equilateral triangle. Each reservoir was connected to the other through microchannels (length: 450 µm; width: 50 µm; height: 3 µm). The microchannels were coated with 0.1 mg/mL poly-1-lysine (Sigma Aldrich) for 24 hours in an incubator. The channels were then rinsed 3 times with deionized (DI) water and coated with 20 ug/mL laminin (Sigma Aldrich) for 2 hours. The channels were washed again 3 times with DI water and washed and filled 3 times with Neurobasal-B27 containing 2 mM glutamine and 100 U/ml penicillin/streptomycin (hippocampal culture medium). The microfluidic chips were placed in an incubator until use.

Dissection and Cell Culture.

All animal work was approved by the MIT Committee of Animal Care and Division of Comparative Medicine, and abided by institutional, state, and federal guidelines for animal welfare. Hippocampi were harvested from E18 Sprague Dawley rats (Charles River Laboratories,), and digested in ice-cold Hank's balanced salt solution (HBSS), buffered with 10 mM HEPES, pH 7.3. The tissue was digested by a 30 min incubation in 2 ml of HEPES buffered HBSS containing 20 U/ml of papain (Worthington Biochem.), 1 mM EDTA and 1 mM L-cysteine. Next, the tissue was rinsed three times with 8 ml of hippocampal culture medium. The cells were gently triturated in 1 ml of hippocampal culture medium, counted with a hemocytometer, and flowed into the device. The cells were maintained at 37° C., 5% $CO_2$.

Neuron Seeding in Device.

Before seeding, the reservoir of the microfluidic chip was emptied without removing the media from the microchannel. For each inlet reservoir, 4 µL of high density (>8 $10^6$ cells/mL) dissociated neuron solution was placed near the entrance of the microchannel. The chip was returned to the incubator for 5 minutes in order to let the neurons adhere on the coated glass and the seeding process was repeated 3 times to achieve a high cell density. At the end, the input and output reservoir were quickly filled with hippocampal culture medium and chips were returned to incubator.

Neuron Transfection.

24 hours after plating, neurons were transfected with a tubulin-GFP baculovirus (Tubulin-GFP Bacmam 2.0 virus, Life Technologies) in a ratio 2 uL of virus for $10^4$ cells, as indicated by the distributor. Cells were then imaged in fluorescence after 16 hours of incubation.

Image Acquisition.

Images were acquired with an Axiovert 200M (Zeiss) fitted with a cooled CCD camera LaVision ImagerQE (LaVision) and an automated stage Ludl MAC 5000 (Ludl). The microscope was controlled with Metamorph software (Molecular Devices) and images were analysed using ImageJ and Matlab (The Mathworks) software.

In Vitro Platform to Apply AC Electric Signals Inside the Incubator.

AC signals were applied to the microelectrodes via a custom platform that was placed inside the incubator. The microfluidic chips were aligned and inserted into a Zero Insertion Force (ZIF) connector that was linked to an Arduino homemade printed-circuit-board stack. The Zero Insertion Force connector acts as a mechanical and electrical holder for the chip. The stack was composed of 3 boards, a master Arduino board, a direct digital synthesis (DDS)-generated AC signal board, and a routing board. The DDS board (based on the DDS-60 Daughtercard, Midnight Design Solution) was able to generate an AC signal in the range of 0-60 MHz and 0-10 Vp-p. The routing board (using an ADG333ABR switch, Analog Devices and 74HC595 shift registers, Texas Instruments) was able to reroute and maintain the AC signal to one or more electrodes. A Raspberry Pi minicomputer, which was connected to the Arduino by USB, piloted the entire stack. A web server was installed on the Rasberry Pi so that the frequency and the voltage for each electrode could be remotely changed via a web browser in real time. The electrical signals are selectively send to each electrode via a home-made arduino board composed of electrical switch and shift registers. The commands to close switches are sent to the arduino by a Rasberry Pi on which a web-server is constantly running. Both arduino boards and ZIF connectors are finally situated in the incubator.

Axon Length Measurements.

All the grooves were photographed under epifluorescence and the length of the axon was measured with Matlab. The imaging algorithm consists of first enhancing contrast and brightness, then binarizing the image (threshold value manually optimized for each image), then applying a Hough transformation and finally measuring the gap between the channel edge and the end of the axon. For each voltage and frequency, we defined the standardized axon length as the ratio of the distance between the observed axon length (AL on FIG. 6) and the distance between the edge of the channel and the first electrode (DCE on FIG. 6). For the axon-lock system, the axon lengths were measured with the same algorithm than previously. When the growth cone was hidden by the electrodes, the position was assumed to be the middle of the electrode itself with an error of the electrode width.

Neuronal Network Stimulation.

The neurons were stained with Oregon green BAPTA1 (Life Technologies) for 1 hour and washed with medium. To stimulate only one sub-population, 20 uL of a 90 mM KCl solution was injected in the inlet of one microchamber only. The reservoirs of the other population of the neurons were filled with 50 uL of medium each, thus creating a pressure differential between chambers to prevent KCl from flowing out of the injected microchamber. The details of this fluidic flow compartmentalization are given in supplementary information.

Action Potential Recording.

Action potentials were recorded through the microelectrodes themselves in the axon-lock triangle chip. Microelectrodes from the same microchannel were connected as stimulation and as recording electrodes via the ZIF module. A pulse generator (TTi) was linked to a current converter (Isolator-10, Axon Instruments) then to the stimulation electrodes. The recording electrodes were linked to a lock-in amplifier ($\times 10^4$ gain, ISO-80, World Precision Instruments) and to a PC oscilloscope (PicoScope, PC oscilloscope software). The signals were then exported into Matlab and temporally synchronized.

Statistical Analysis.

For axon stoppage analysis, differences were addressed by an unpaired Student's t-test from two independent experiments in which each experimental condition was performed in duplicate. For all analysis: *p-value <0.05; p-value <0.01; *p-value <0.001.

EXAMPLE 6

This example describes the selective patterning of three dimensional collagen matrix (e.g., collagen scaffold) in a microfluidic device containing electrodes (e.g., electro-microfluidic chip).

Figure 16:
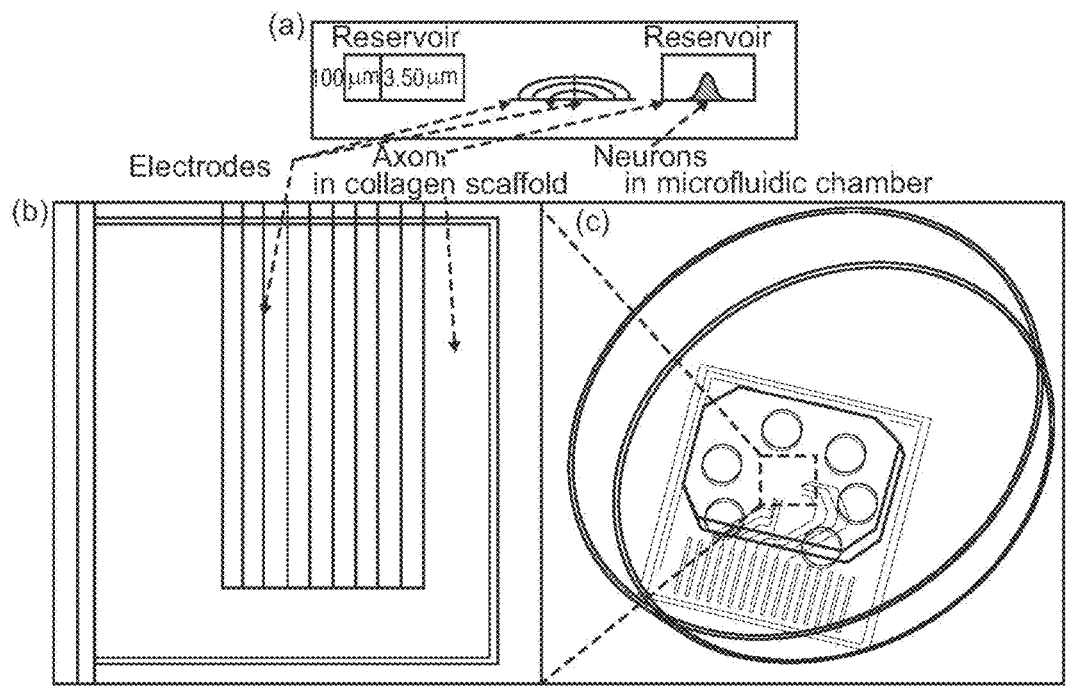
FIGS. 16A-C illustrate devices for altering neurite growth in accordance with certain embodiments of the invention.

Collagen was selectively patterned inside microfluidic channels and/or other microfluidic structures without the need for extra patterning channels or additional equipment. Depending on the height of the microfluidic channel, the method was based on capillary flow balancing to perfuse defined areas of the microfluidic chip with collagen. Briefly, collagen was flowed inside the entire microfluidic chip and removed in certain microchannels using only acrylic acid (AA) due to flow balancing in the chip. AA is known to disrupt the stabilizing hydrogen bonds between collagen fibrils, resulting in solubilisation of the collagen scaffold. Details of this protocol are further described in Example 11. FIG. 16 shows an illustration of the cross-section of the microfluidic chip and a picture of the microfluidic chip itself. FIG. 16A is a schematic of the compartmentalized electro-microfluidic chip that comprises neuronal bodies in a chamber and axons that can grow into collagen scaffolds of varying heights. FIG. 16A is a bright field X10 picture of developing axons in a 5 micron height collagen scaffold without any field after 6 days in vitro (DIV). Axons showed an oriented growth from the cell body compartment within the collagen scaffold. FIG. 16C is a photograph of the microfluidic chip within a petri dish. The electrical connections are visible on the lower part of the chip.

EXAMPLE 7

This example describes the use of AC electric fields to guide axon growth in collagen scaffolds within microgrooves having a height of 5 microns. The topography of the electrodes did not influence axon growth. However, application of an alternating current at 3 Vpp and 150 kHz repelled axon growth in the high electric field region and caused axons to change direction and grow in the low electric field region.

Microfluidic chips, such as those shown in FIG. 16, were used with co-planar electrodes and neurons growing on functionalized surface to address the hypothesis that AC electrokinetics forces can direct axon growth in three dimensions in collagen scaffolds by combining the microchannel geometrical constraints and the electric field distribution. To address this hypothesis, the development of rat E-18 hippocampus neurons were observed in the electro-microfluidic chip as described above in Examples 5 and 6 with varying grooves heights and electrode geometries. When the microgroove height (h) was 5 μm, axon growth was limited to a single plane because of spatial confinement of the growth cone. 24 hours after seeding of the neurons in the cell reservoir, axons started to extend into the microchannel towards the electrodes. At this point, the electric field was activated by applying alternating currents at 3 Vpp and 150 kHz. In the control chip, the field remained deactivated. Cells were imaged every 24 hours to monitor the growth and viability.

Figure 17:
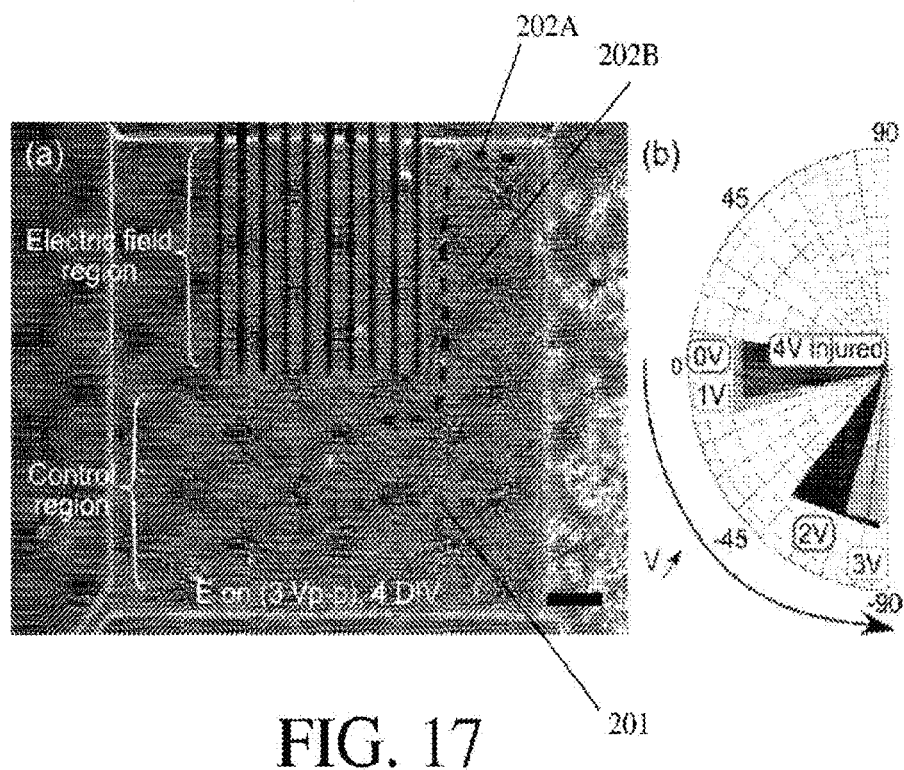
FIGS. 17A-B illustrate certain embodiments of the invention generally directed toward changing the orientation of a neurite.

Within four days in vitro (4 DIV), axons in the control chip filled the complete microchannel (600 μm×600 μm) as shown in FIG. 17. No difference in growth speed could be observed between axons growing over deactivated electrodes or axons growing in the control region (arrow 201), showing that the topography of the electrodes (h=200 nm) did not influence the growth. Individual cells migrated from the cell reservoir into the microchannel. Because of the height limitation these were most likely glial cells that squeezed into the narrow opening following guidance clues from developing axons.

In the control region of the activated chip (arrow 201), axons showed approximately the same growth speed and density as in the deactivated chip (see FIG. 17A). In contrast however, the electric field region was nearly free from axon growth. Axons indeed turned in front of the first electrode and followed the field lines until reaching regions of lower field strength (arrow 202). The distance between the electrodes and the parallel axons was approximately 5-10 μm.

FIG. 17B shows the change in growth direction evaluated as function of the applied voltage. For each condition, the electric field region of three different samples with one channel each were analyzed with each tested channel containing a minimum of 50 dendrites. The angular distribution shown in the figure represents the relative change of the growth angle before and after the encounter with the electric field. The black lines are the median angle for each voltage. With deactivated electrodes (0 V), neurites grew parallel to the channel (median=0°) and had only minor changes in growth direction that occurred equally to both sides (±10°). A similar deviation of growth direction could be found for an activated field with 1 Vpp. However, the median angle was slightly shifted into the negative (−2.5°), meaning away from the electrodes. DEP forces at this voltage are minimal and the observed change is presumably not connected to AC electrokinetics. Application of 2 Vpp led to turns of nearly −70° in average with a range from −50° to −85°. 3 Vpp resulted in the largest turns of up to −90° and parallel growth to the electrodes as was observed in FIG. 17A. In the range from 2-3 Vpp, the model described in Example 2 estimates a maximum DEP force of 66 pN acting on the growth cone. This force was in the same order of magnitude as the traction forces that cause growth cone turning in the body. Therefore, DEP was the likely cause of the change in growth direction. Finally, 4 Vpp at the electrodes resulted in injury of the neurites and no angular deviation could be determined (line at 0°). These findings were consistent with the cell viability tests at different voltages described in Example 13.

In some cases, individual axons breached into the electric field region from the side. This might be the result of an inhomogeneous electric field and consequently reduced DEP at the edges of the interdigitated electrode array. In some experiments, breaches of individual axons growing directly next to the channel wall were observed. It is possible that strong mechanical cues like the channel wall exceed the DEP effect and allow axons to grow into the electric field region. For 5 μm height, the presence or absence of scaffold in the channel resulted in the same behavior. The growth cone largely interacted with the functionalized surfaces instead of interacting with the scaffold. Therefore, for small channel heights the scaffold filled channel can be regarded equal to a high channel filled with media.

EXAMPLE 8

This example describes the use of AC electric fields to enhance axon growth velocity in collagen scaffolds. This example demonstrates chemical and contact-free promotion of axonal growth.

Figure 18:
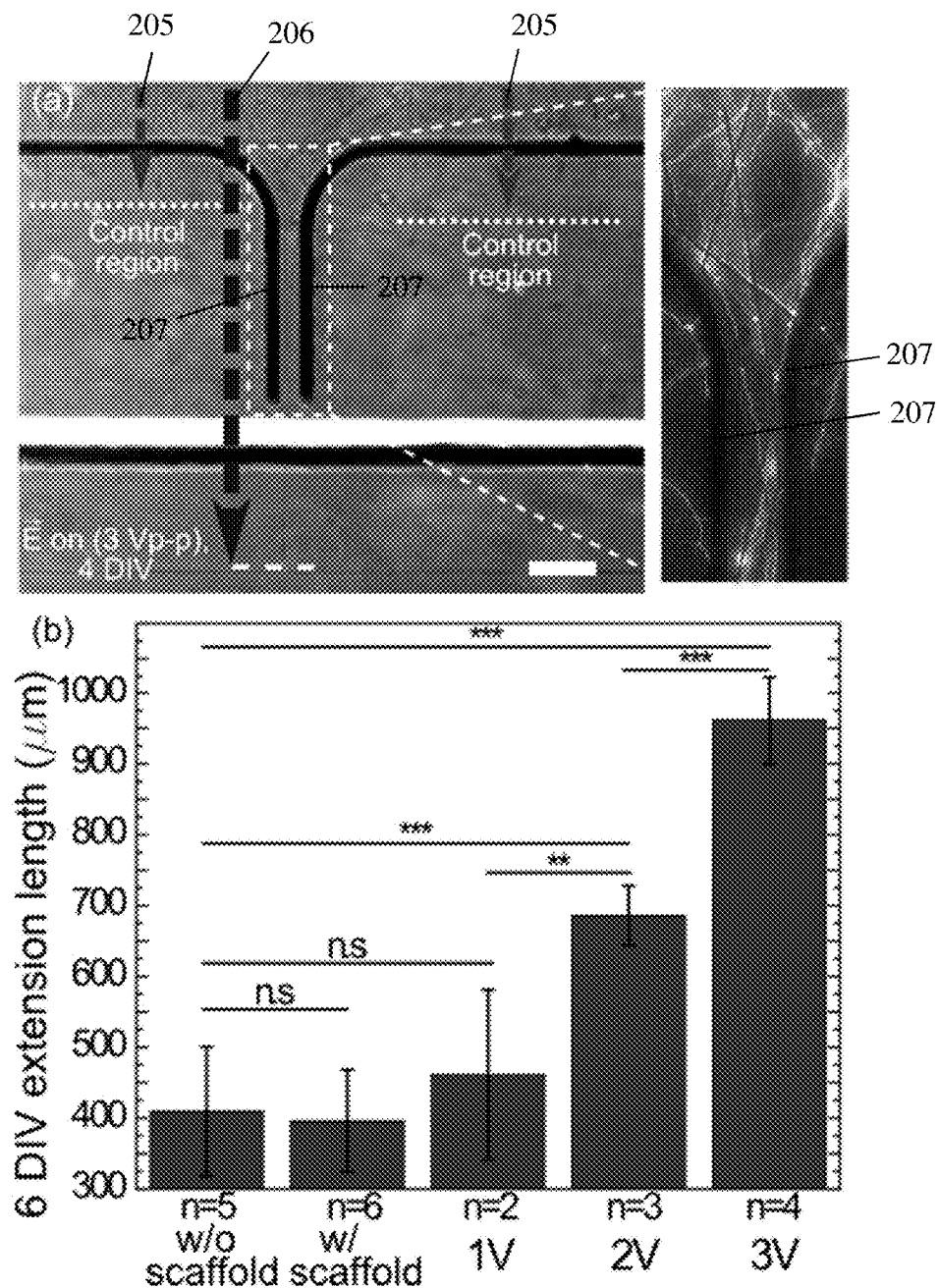
FIGS. 18A-B illustrate certain embodiments of the invention generally directed toward directing neurite growth in a certain region and accelerating neurite elongation.

A funnel shape electrode was used to investigate the influence of electrokinetic confinement of axons within the vicinity of the signal and grounded electrodes as shown in FIG. 18A. The white dashed lines mark the growth cones of developing axons in the control region (arrow 205) and in the funnel region (blue arrow). Axons were tracked (arrow 205) in FIG. 18A to demonstrate the funnelling effect. FIG. 18A is an image of axonal development in a 5 micron thick collagen filled microchannel with electrodes in a funnel-like design (4 DIV, 100 kHz, 3 Vp-p). Axons that were between the funnel electrodes (arrow 206) grew faster than axons above unactivated electrodes (control, arrow 205). The inset shows funneling of axons within the curved part of the electrodes 207 with tracking of individual axons that highlights funnel effect. Further, an increase in growth speed compared to unconfined axons was observed. To quantify the effect, the lengths of developing axons were measured. FIG. 18B shows the extension length in the funnel region after 6 DIV for different applied voltages and a control chip (no electrodes). FIG. 18B is a graph of neurite extension lengths after 6 DIV under the same field. Confining axons within the funnel significantly enhanced their growth speed for 2-3 V as compared to axons on 2D surfaces (glass) or in 5 mm-thick gels above unactivated electrodes (0 V). (*, $p<0.001$; , $p<0.01$). No significant difference was observed between the control, deactivated electrodes, and 1 Vpp ($l_{1v}$=450 μm). An increase of the voltage to 2 Vpp led to a significant rise in extension length to $l_{2v}$=680 μm. In an even stronger field with 3 Vpp, the extension length ($l_{3v}$=960 μm.) was more than doubled compared to the control. Besides the spatial confinement of axons, an increase in growth speed was observed. It is hypothesized that the growth cone needed less time for probing of the environment because AC electrokinetic forces limited the effective probing area to a 1-D line

EXAMPLE 9

This example describes the use of AC fields to slow down axon growth in collagen scaffolds within microgrooves having a height of 10 microns. A combination of electrical forces and mechanical forces were used to slow down axon growth.

The grooves height was increased to h=10 μm and neurons were seeded in the microfluidic chip. 24 hours after seeding of the neurons in the cell reservoir, axons started to extend into the microchannel towards the electrodes. At this point, the electric field was activated and different potentials between 1 Vpp and 3 Vpp were applied at a constant frequency of 150 kHz. Control chips with no electrodes or deactivated electrodes were used.

Figure 19:
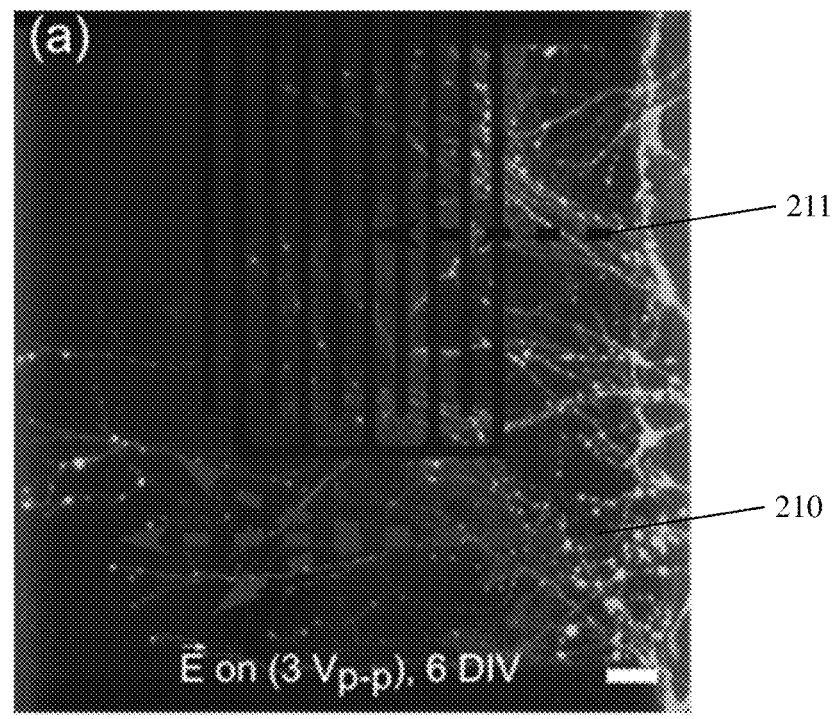
FIGS. 19A-B illustrate certain embodiments of the invention generally directed toward slowing neurite elongation.
Figure 19:
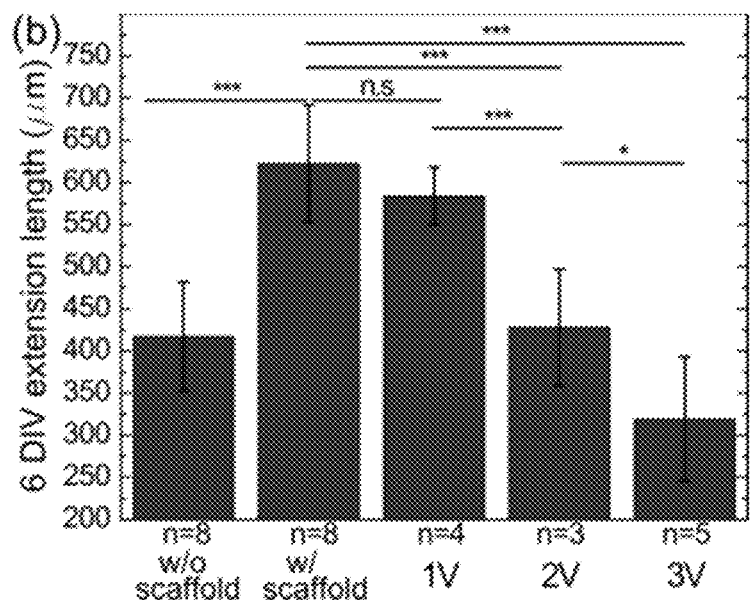

Fluorescent images were obtained after 6 DIV by fluorescence imaging as shown on FIG. 19.

The presence of a scaffold enhanced the growth speed by roughly 30% over functionalized surfaces. Applying 1 Vpp at 150 kHz to the electrodes had no significant effect on the outgrowth. However, 2 Vpp and 3 Vpp significantly reduced the length of the axons by 32% and 48% respectively. A potential explanation for growth promotion was the alignment of collagen fibers parallel to the growth direction as a result of the scaffold filling protocol. Aligned collagen fibers provided a track-like mechanical guidance clue that promoted axon growth, likely because of reduction in time spent deciding which path/cue to take.

The simulation based on the presented model predicted a DEP force of only 10 pN for 1 Vpp at 150 kHz. Hence, the exerted force on the growth cone was easily surpassed by other guidance clues like substrate stiffness. This can explain why no influence on extension length was observed at low voltages. In contrast, higher voltages (2-3 Vpp) induced a significant decrease in extension length. A possible explanation would be a spatial confinement of the growth cone that would have been pushed up and away from the electrodes towards the channel top resulting in a competition between the physical confinement of the microchannel and the repelling effect of the electric field, resulting in a decrease of the extension length.

FIG. 19A is an image of axonal development in a 10 mm-thick collagen-filled microchannel after 6 DIV (100 kHz, 3 Vp-p). Axons growing above the electrodes (arrow 211) are shorter than those away from the electrodes (arrow 210). FIG. 19B is a graph of neurite extension lengths after 6 DIV under the same field for various field strengths. Axonal growth in collagen decreases with increasing voltage, and can be slower than growth on 2D surfaces (glass). (*, $p<0.001$; , $p<0.01$; *, $p<0.1$).

EXAMPLE 10

This example describes the use of AC fields to push up axon growth in the depth of collagen scaffolds having a height of 50 microns, such that axon extension occurred in multiple dimensions (e.g., xy plane, yz plane, xz plane).

To emulate a three dimensional growing environment, the microgrooves height was increased to 50 μm filled with collagen scaffold. It was hypothesized that axons growing in such a scaffold would be deflected in the depth as the electric field extends in the collagen. About 24 hours after seeding of the neurons in the cell reservoir, neurites started to extend into the scaffold filled microchannel towards the electrodes. At this point, the electric field was activated and different potentials between 1 Vpp and 3 Vpp were applied at a constant frequency of 150 kHz. Control chips with no electrodes or deactivated electrodes were used.

FIG. 20A shows a schematic and a confocal image of axons growing in a 50 μm high, collagen-filled channel after 6 DIV and activated electrodes (3 Vpp, 150 kHz). The confocal image shows the side view of fluorescent axons traversing the scaffold filled microchannel along the red line in FIG. 20A. With no exposure to the field (top), most of the axons grew close to the glass bottom of the channel. Axons that grew over the activated electrodes (bottom) were deflected in the z direction. Axons deflection was observed and quantified within the scaffolds with a confocal microscope. FIG. 20B shows the output from the image processing and side view reconstruction of 3D images produced by the confocal microscopy. The side-view confocal image shows the axons traversing the channel along the dashed line in FIG. 20A for unactivated (top) and activated (bottom) electrodes. Without electric field, axons were statistically distributed along the height of the channel. With applied field, axons growing close to the electrodes performed a z-step (solid line). The lowest height of axons in the field region was represented by the horizontal dashed line. FIG. 20C shows the average height of the first axons for the controls and different voltages from 1 Vpp to 3 Vpp (*, $p<0.001$; , $p<0.01$). The control was performed with either a channel without electrodes or with deactivated field. No significant difference in height was observed between growth in channels without electrodes, with deactivated electrodes, or with 1 Vpp at 150 kHz. For applied voltages between 2-3 Vpp, there was a significant rise of axons growing close to the electrodes in the z-direction. For 2 Vpp, the lowest axons rose to an average height of 7±1.5 µm for 3 Vpp to 10±2 µm over the electrodes.

It was also noticeable that rise of axons took place much quicker than the fall after the electric field region. Also there were less axons growing close to the channel bottom after passing the field. It appeared that axons were repelled quickly upwards by electrokinetic forces and statistically oriented themselves again after passing the high field region. Electrokinetic forces acted upwards and away from the edge of the electrode, causing the axon to perform a 'step' over the high electric field region.

EXAMPLE 11

This example describes a method of using an AC field to cause a first and second population of neurites to overlap within a three-dimensional matrix without forming a neural connection between neurites in the first and second population.

To illustrate how these unit operations described in Examples 6-10 could be used for various applications, a method to create tunable axonal crossings was developed. The stopping, funnel, and pushing functionalities described in the above Examples were combined to create a axon crossing. The chip design is shown in FIG. 21A and consisted of:

1—Two individual populations of neurons compartmentalized and fluidly isolated that were fluorescently stained;
2—Microfluidic focusing grooves that focused the axons beams towards the active part of the chip;
3—Funnel shape electrodes, one pair for each groove; and
4—The overlap region.

The active zone or overlap region was a combination of guiding and pushing electrodes and a local 50 micron high microgroove in which the axons can be pushed up. In the device, collagen was selectively injected in the grooves and removed from the microchannels where cell bodies were seeded. To boost axonal growth in the channel direction, it was found that maintaining a hydrostatic pressure (HP) difference between the neurons compartments (left side on FIG. 21A) and the ones with no neurons (right side) increased axon growth by at least 30% (it took 8 to 9 days for axons to connect with the other compartment without HP versus 5 to 6 days with HP). FIG. 21A is a stitched transmission picture (magnification of ×20) of the axon bridge device. Two fluidly isolated neuron population were plated and individually stained in microchannels. Compartmentalized grooves allowed axons to develop and focus towards the bridge region that is enhanced in the inset. It was composed of funnel electrodes that focused the axons beam before the actual contactless overlap region. The scale bar indicates 100 microns.

Without any field or HP, axons growth was clearly isotropic with a preference towards maintaining initial direction (fluorescence quantification showed a growth rate of 78±12% in the same direction of the initial channel) as shown in FIG. 21B. FIG. 21B shows a fluorescent stitched picture (magnification ×20) of the overlap region without any field or hydrostatic pressure from the microchannels. The scale bar indicates 100 microns. Axons growth was directed towards external grooves and located in all adjacent grooves. In this case, neurites from both populations overlapped at the overlap region, but the neurites formed neural connection and also projected in all channels. On the contrary, when both the field was activated and HP maintained as shown in FIG. 21C, the overlap region clearly focused the beams of axons, allowed them to overlap without forming neural connections, sprouting in the other channels, and increased their growth within the same direction. FIG. 21C shows a fluorescent stitched picture (magnification x20) of the bridge region with the field activated and hydrostatic pressure. The scale bar indicates 100 microns. A high degree of fasciculation of the axons was observed at the exit of the overlap region. The adjacency matrixes of each situation (1 and 2 respectively) are given by $C_1$ and $C_2$.

$$C_1 = \begin{bmatrix} 0 & 1 & 1 & 1 \\ 0 & 0 & 0 & 0 \\ 1 & 1 & 0 & 1 \\ 0 & 0 & 0 & 0 \end{bmatrix}$$

$$C_2 = \begin{bmatrix} 0 & 0 & 0 & 1 \\ 0 & 0 & 0 & 0 \\ 0 & 1 & 0 & 0 \\ 0 & 0 & 0 & 0 \end{bmatrix}$$

Alternatively, a neural connections can be made using two facing populations. Two populations of facing neurons were bi-directionally connected in the axon bridge device as shown in FIGS. 7D-E. To construct the neural connection, the field was activated (150 kHz and 4 Vpp) and the HP was maintained low in the output perpendicular reservoirs. The adjacency matrixes of each situation (1 and 2 respectively) are given by $C_1$ and $C_2$.

$$C_1 = \begin{bmatrix} 0 & 0 & 0 & 1 \\ 0 & 0 & 0 & 0 \\ 0 & 0 & 0 & 0 \\ 1 & 0 & 0 & 0 \end{bmatrix}$$

$$C_2 = \begin{bmatrix} 0 & 0 & 0 & 0 \\ 0 & 0 & 1 & 0 \\ 0 & 1 & 0 & 0 \\ 0 & 0 & 0 & 0 \end{bmatrix}$$

EXAMPLE 12

This example describes materials and methods used in Example 6-13.

Microfabrication of Electrokinetic Devices.

The microfluidic chip was fabricated on standard microscope glass slides (25×75×1.1 mm, Sigma). A 10/100 nm Ti/Au bi-layer was deposited on a standard microscope slide (25×75×1.1 mm, Sigma) using e-beam deposition. The layer was then structured using standard lithography and wet-etched for 4 min in 250 mL $H_2O$+200 mL HCl+100 mL $HNO_2$. Subsequently, a second wet-etch of 10 min in HCL: Water (2:1) was performed to remove remaining titanium.

The microchannels comprised two types of components: high channels (100 microns) for cell injection and shallow channels (5-50 microns in height) for axon growth. They were molded from a SU-8 (Microchem) master that was fabricated with a two-step lithography process with thin (SU-8 2007) and thick (SU8-2050) resists.

Microchannels were then molded with degassed and cured PDMS (9:1 mass ratio with curing agent, Sylgard 184, Dow Corning). The microgrooves where manually aligned under a binocular after air plasma exposure (2 minutes) and immersion in methanol (5 minutes). The assembled chip was cured at 100° C. for 30 minutes. After the initial mold, a plastic master was fabricated for further replication of the device. The PDMS molds were then manually aligned to the electrodes using a stereo microscope (M80, Leica) and bonded on the glass substrate after 2 minutes exposure to air plasma. The assembled chip was cured at 80° C. for 30 min.

Several microfluidic chips were constructed in this way. To evaluate the effect of AC fields on axonal growth in collagen scaffolds, two-compartment chips were made of rectangular microchannels (length: 4000 microns; width: 500 microns; height: 100 microns) separated by arrays of planes (length: 600 microns; width: 600 microns; height: 5 to 50 microns). The axon bridge chip was a four compartments chip made of 5-mm punched inlet and outlet reservoirs connected to four inner reservoirs (length: 1000 microns, height: 100 microns) placed in an square. Each reservoir was connected to the other through microchannels (length: 500 microns; width: 50 microns; height: 5 microns).

Surface Treatment and Coating.

To clean the glass substrates (with electrodes), the glass substrates were boiled for 1 h in 7× detergent (MP Biomedicals), rinsed for 10 s in DI water, cleaned with Aceton, Isopropanol and DI-water and finally baked for 2 h at 200 C in an oven. After baking, the substrate was plasma-cleaned and bonded to the PDMS microfluidics. Channels were filled with Poly-D-Lysine (0.1 mg/ml, Sigma) and incubated at 37° C. for at least 20 hours. To remove loose PDL, channels were washed twice with DI water without emptying the main channel. Subsequently, the channels were filled with Laminin (20 μg/ml, Sigma) and incubated at 37° C. for 2 hours. Laminin was aspirated and the channels washed 3 times with Plating Media (DMEM+10% FBS+1% PS+1% L-Glutamin) from one side to the other. A chip functionalized in this fashion was stored for a maximum of 2 hours prior to cell seeding at 37° C. The hippocampal culture medium was neurobasal-B27 containing 2 mM glutamine and 100 U/ml penicillin/streptomycin.

Selective Patterning of Collagen Scaffolds.

Collagen (10 mg/ml, Gibco) was mixed on ice with a buffer solution (250 mM HEPES in 2×PBS, pH 7.4 with 2M NaOH) for 1 min. The ratio of collagen to buffer depended on the desired final collagen concentration but was close to 1:1. Before pipetting into the chip, the collagen solution was incubated 10-30 min on ice to control the fiber thickness.

Figure 22:
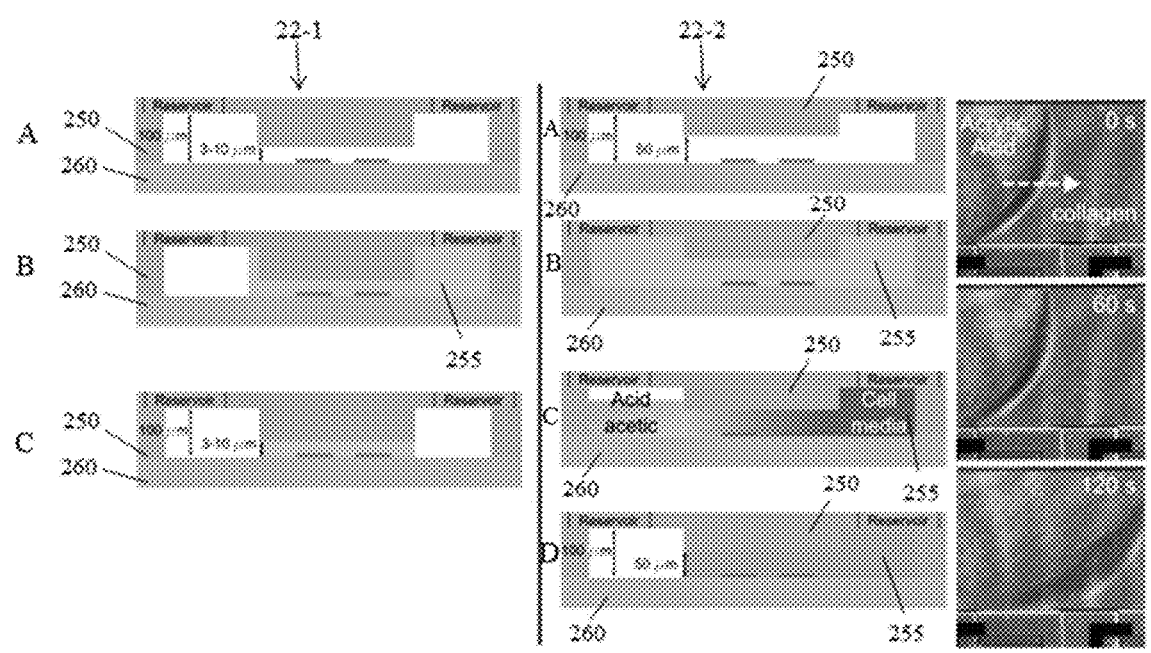
FIGS. 22A-D illustrate methods of filling a channel with a scaffold, in accordance with certain embodiments of the invention.

First, the bonded chip was functionalized with poly-d-lysine and laminin to allow adhesion of the neuron soma in the cell reservoir. Second, the complete microfluidic channel was filled with collagen type I solution through the scaffold inlet and incubated at 37° C. until complete gelation. Then acetic acid (0.2 M, pH 3.5) was pipetted into the cell reservoir to destabilize the collagen. To prevent acid from etching into the microfluidic channel, a hydrostatic pressure was applied by pipetting cell media into the inlet. After 30 min etching at 37° C., the destabilized scaffold was carefully aspirated through the cell outlet. To remove acid and residues, the channel was flushed three times with buffered cell media. FIG. 22 shows an illustration of the protocol used for capillary filling 22-1 and microfluidic patterning 22-2. FIG. 22A shows the electro-microfluidic chip with media reservoirs (dashed lines), cell and scaffold reservoir (100 μm) and microchannel (50 μm). FIG. 22B illustrates the electro-microfluidic chip after filling and complete gelation of the structure with collagen. FIG. 22C illustrates the electro-microfluidic chip after the acid etches the cell reservoir while the microchannels are protected by application of a hydrostatic pressure from the scaffold filled reservoir. FIG. 22D illustrates the electro-microfluidic chip after the destabilized scaffold was aspirated and excessive acid and remainders are removed with buffer solution. FIG. 22E are time-lapse images of the process and from the time, an etch rate of 500 μm/min can be derived. As a result, scaffold remains only in the electrode channel and in the media reservoir while the cell reservoir is empty and ready for the seeding of cells.

Dissection and Cell Culture.

All animal work was approved and abided by institutional, state, and federal guidelines for animal welfare. Hippocampi were harvested from E18 Sprague Dawley rats (Charles River Laboratories,), and digested in ice-cold Hank's balanced salt solution (HBSS), buffered with 10 mM HEPES, pH 7.3. The tissue was digested by a 30 min incubation in 2 ml of HEPES buffered HBSS containing 20 U/ml of papain (Worthington Biochem.), 1 mM EDTA and 1 mM L-cysteine. Next, the tissue was rinsed three times with 8 ml of hippocampal culture medium. The cells were gently triturated in 1 ml of hippocampal culture medium, counted with a hemocytometer, and plated at a density of 35,000 cells/mm$^2$. The cells were maintained at 37° C., 5% $CO_2$. The cell medium was renewed for 50% every 3 days. To maintain hydrostatic pressure, the reservoirs of the neurons compartment were systematically filled with media every day and the others were emptied without drying the reservoir surface.

Neuron Seeding in Device.

Before seeding, the reservoir of the microfluidic chip was emptied without removing the media from the microchannel. For each inlet/outlet reservoirs, 6 μL of plating media was placed in the outlet and immediately after, 4 μL of high density (>8 10$^6$ cells/mL) harvested neuron solution was placed at the inlet reservoir. The chip was returned to the incubator for 5 minutes in order to let the neurons adhere on the coated glass and the seeding process was repeated 3 times. At the end, the input and output reservoir were quickly filled with hippocampal culture medium and chips were returned to incubator and plugged into the in-vitro platform to apply AC fields that was described in Example 5.

Neuron Transfection.

For each fluorescent lentivirus, either tdTomato or EGFP was cloned after the CMV promoter and before a Woodchuck Hepatitis Posttranscriptional Regulatory Element (WPRE) in a lentiviral transfer plasmid and amplified in Stbl3 cells. To produce the viruses, 3 million HEK293FT cells (Life Technologies) at low passage (less than 10) were seeded the day before transfection in a T-225 flask in DMEM supplemented with 10% FBS (Hyclone). Cells were transfected in OptiMEM using 100 ul of Lipofectamine 2000 and 200 ul of Plus reagent (Life Technologies) with 20 ug of the transfer plasmid (either tdTomato or EGFP), 15 ug of psPAX2, and 10 ug of pVSVg (Addgene). After 6 hours, the media was removed and replaced with DMEM supplemented with 10% FBS and 1% BSA. After 60 hours, the supernatant was removed and centrifuged at 3000 rpm for 10 minutes at 4° C. This supernatant was filtered through a 0.45 um low protein binding filter (Millipore). To achieve 300× concentration of viral particles, the filtered lentivirus was ultracentrifuged (Sorvall) at 24,000 rpm for 2 hours at 4° C. and then resuspended overnight at 4° C. in D10 supplemented with 1% BSA. Aliquots were stored at −80° C. until neuron transduction.

Image Acquisition.

Images were acquired with an Axiovert 200M (Zeiss) fitted with a cooled CCD camera LaVision ImagerQE (LaVision) and an automated stage Ludl MAC 5000 (Ludl). The microscope was controlled with Metamorph software (Molecular Devices) and images were analysed using ImageJ and Matlab (The Mathworks) software. Sets of images were stitched together with ImageJ plugin for Fiji.

Image Analysis to Quantify the Number of Neurons.

Neurons body were counted on stitched images with ImageJ plugin MOSAIC.

Image Analysis to Quantify Deviation Angle, Growth Velocities and Axon Height of Neuritis.

The quantification of neurite alignment and length was performed as follow: images of three samples containing one channel with collagen scaffold were analyzed for each condition and quantified using Matlab (MathWorks). One sample contained a minimum of 50 dendrites. A threshold value of the reflection intensity was defined to isolate neurite from background. By fitting an ellipse to the major axis of each dendrite, the angle of the neurite to the main channel direction was determined. The orientation of dendrites parallel to the alignment direction corresponded to an angle of 0°. The angular distribution of neurite was determined based on the relative frequency of orientation angles (classified into bins of 180 angles) and by a fit to a Gaussian full width at half maximum (FWHM). Deviation of the initial trajectory was defined such as the angle at the evaluation point along the neurite has more than 10% change compared to the one 50 microns (5 times the growth cone diameter) before. Deviation was then recorded to be the relative difference between those to angles. The length of each neurite was measured from its origin at the beginning of the microchannel filled with collagen to its end. Changes in direction along its course were taken into account by tracing along the entire length of each extension. Extensions that were solitary and clearly isolated were measured only to exclude the possibility of mix-up with other extensions. Growth speed was then evaluated by a dividing the relative measured length by the time-lapse between those measurement. Axon height in 3-D was determined by post-processing of fluorescent confocal image stacks in Matlab. The script contained a Gaussian filter to reduce noise and to determine the centre of the axon. The plot contains the detected centres in the individual slices of the channel.

Statistical Analysis.

For axon stoppage analysis, differences were addressed by an unpaired Student's t-test from two independent experiments in which each experimental condition was performed in duplicate. For all analyses: *p-value <0.05; p-value <0.01; *p-value <0.001.

EXAMPLE 13

This example describes cell viability at high strength AC electric fields and a method of confining developing axons within electrodes.

Cell Viability at High Strength AC Electric Fields.

Exposing neurons to high strength (E>105 V/m) AC electric field may result in harming the development of axons. To address this issue, cell and neurite appearance were monitored every 24 h during the experiments with bright field microscopy. Additionally, cell survival after exposure to different voltages was investigated with calcein AM (Invitrogen) staining. Calcein AM becomes fluorescent in live cells through an enzymatic reaction.

Figure 23:
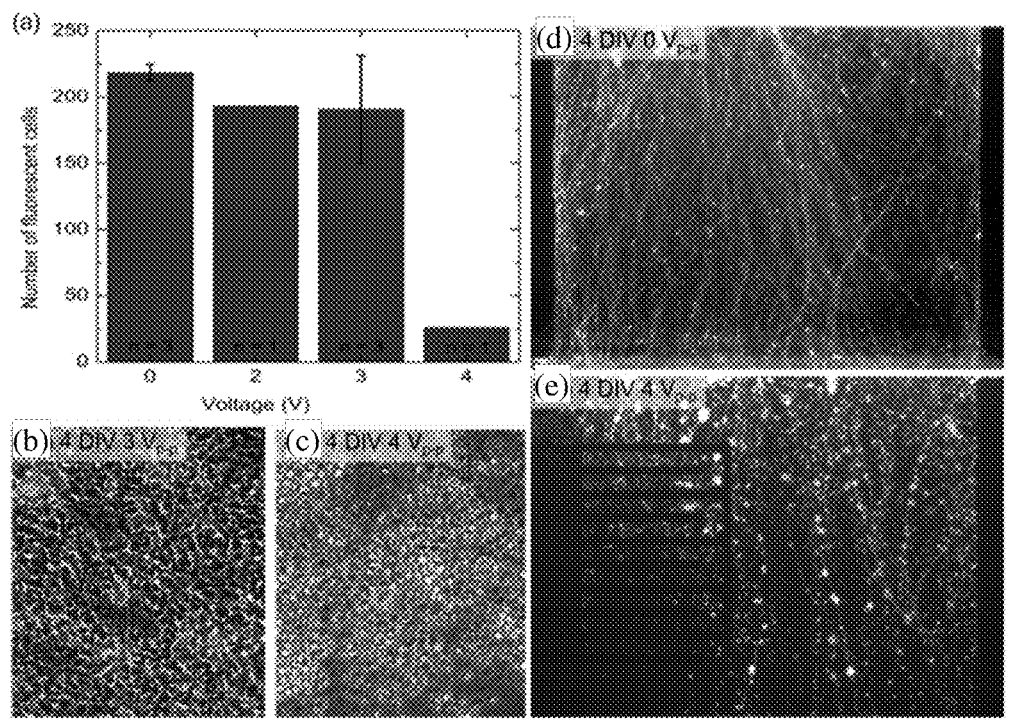
FIGS. 23A-E illustrate a graph of cell viability for various voltages and images of cells at various voltages, in accordance with one embodiment of the invention.

FIG. 23A shows the number of viable (fluorescent) cells after four days exposure to 0-4 Vpp. No significant difference was observed between the control, 2 Vpp and 3 Vpp. Only a fraction of the cells survived 4 Vpp. FIG. 23A is a graph of the average number of viable cells at different voltages. FIG. 23B shows viable cell culture at 3 Vpp. FIG. 23C shows round, whitish neurons with little interconnections at 4 Vpp. FIG. 23D shows healthy neurites in a control channel. FIG. 23E shows round and irregular neurites at 4 Vpp. Bright field images of the cell reservoirs showed a healthy cell culture (FIG. 23B) at 3 Vpp compared to a unhealthy culture (whitish and rounded cells, little interconnections) at 4 Vpp (FIG. 23C). The same observations can be made for the axons in the microchannel. Compared to viable axons from a control channel (FIG. 23D), axons growing next to electrodes with 4 Vpp applied potential were less in number and showed round and irregular growth.

According to the model described in Example 2, electrohydrodynamic effects including heating of the media became more relevant for voltages greater than 3 Vpp.

This was consistent with the observations of the cell viability experiments. In some experiments however, cell bodies agglomerated after several days. This was presumably attributed to degradation or deficient deposition of cell adhesion molecules (PDL and Laminin) and not connected to electric field effects. It was concluded that the impact of AC electrokinetics on cell viability was minimal for moderate voltages where no excessive heating of media takes place. Confining developing axons within electrodes.

Figure 24:
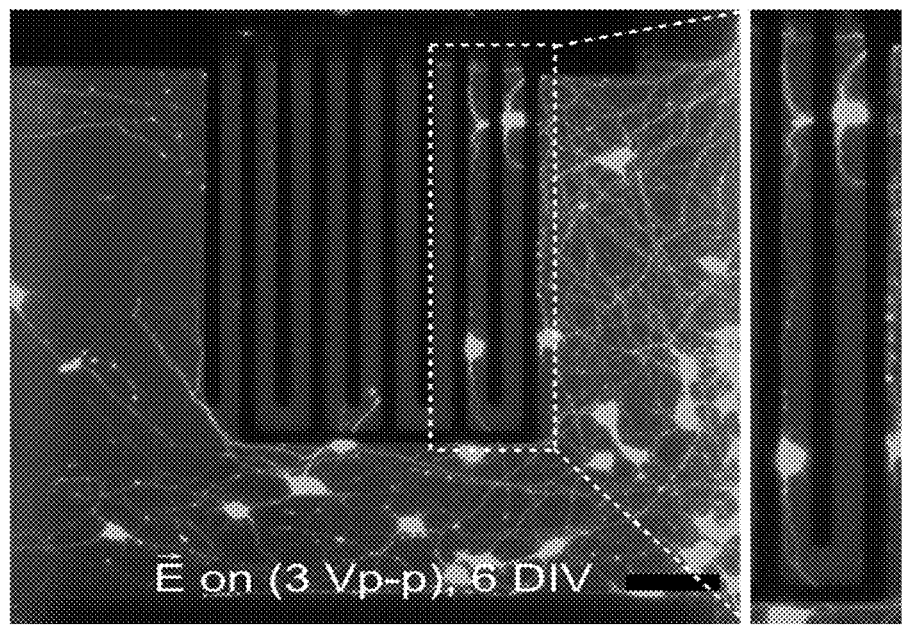
FIG. 24 illustrates neurite growth in a region between electrode pairs, according to certain embodiments of the invention.

When neurons were plated between the electrodes themselves, the axons develops in the vicinity of the electric field, being confined between the edges of the electrodes as shown on FIG. 24.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/ or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or " "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising
providing a first chamber containing one or more first neurites:
providing a second chamber containing one or more second neurites, wherein the first and second chamber are connected by a first channel:
providing an alternating current electric field in the first channel, with the electric field being aligned with at least a portion of the first channel: and
switching on and off the alternating current electric field over time for directionally guiding elongation of neurites inside the first channel by repelling neurite growth in the alternating current electric field region until at least one neurite of the first chamber overlaps at least one neurite of the second chamber.

2. A method according to claim 1, comprising directionally guiding elongation of a first population of neurites and a second population of neurites to form a neural network between the first and second population of neurites.

3. A method as in claim 2, wherein the magnitude of the electric field is greater than or equal to about 100 V/m.

4. A method as in claim 2, wherein the frequency of the electric field is greater than or equal to about 100 Hz.

5. A method as in claim 2, wherein the electric field is non-uniform.

6. A method as in claim 2, wherein said populations of neurites are within a three-dimensional scaffold.

7. A method as in claim 6, wherein the scaffold is a gel matrix.

8. A method as in claim 1, wherein the overlap occurs within a three-dimensional scaffold.

9. A method as in claim 8, wherein the scaffold is a gel matrix.

10. A method as in claim 1, wherein the neurite is an axon.

11. A method as in claim 1, wherein the second neurite originates from a different neuron than the first neurite.

12. A method as in claim 1, wherein the alternating current electric field is switched on and off for a duration and over time to cause the first neurite to overlap with the second neurite without forming a neural connection.

13. A method as in claim 1, wherein at least one neurite originates from a neuron selected from the group consisting of hippocampus neurons, dorsal root ganglion neurons, and retinal ganglion neurons.

* * * * *